United States Patent
Gelvin et al.

(10) Patent No.: US 10,150,969 B2
(45) Date of Patent: Dec. 11, 2018

(54) METHODS AND COMPOSITIONS TO REGULATE PLANT TRANSFORMATION SUSCEPTIBILITY

(71) Applicant: PURDUE RESEARCH FOUNDATION, West Lafayette, IN (US)

(72) Inventors: Stanton B. Gelvin, West Lafayette, IN (US); Nagesh Sardesai, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 205 days.

(21) Appl. No.: 15/004,227

(22) Filed: Jan. 22, 2016

(65) Prior Publication Data

US 2016/0215294 A1    Jul. 28, 2016

Related U.S. Application Data

(62) Division of application No. 13/884,480, filed as application No. PCT/US2011/059944 on Nov. 9, 2011, now abandoned.

(60) Provisional application No. 61/552,127, filed on Oct. 27, 2011, provisional application No. 61/412,684, filed on Nov. 11, 2010.

(51) Int. Cl.
*C12N 15/82* (2006.01)
*C07K 14/415* (2006.01)

(52) U.S. Cl.
CPC ........ *C12N 15/8205* (2013.01); *C07K 14/415* (2013.01); *C12N 15/8261* (2013.01); *C12N 15/8282* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 8,273,954 B1 | 9/2012 | Rogers et al. | |
| 2008/0280010 A1* | 11/2008 | Davies | C07K 14/415 426/601 |
| 2009/0144847 A1 | 6/2009 | Shaikh et al. | |

FOREIGN PATENT DOCUMENTS

| WO | WO 01/20012 | 3/2001 |
|---|---|---|
| WO | WO 2005/028656 | 3/2005 |

OTHER PUBLICATIONS

Friedberg (Automated protein function prediction—the genomic challenge. Brief. Bioinformatics. 7: 225-242, 2006).*
Gelvin (Plant Proteins Involved in Agrobacterium-Mediated Genetic Transformation. Annu. Rev. Phytopathol. 2010. 48:45-68, published online on Mar. 25, 2010).*
Gelvin (Agrobacterium in the Genomics Age. Plant Physiology, vol. 150, pp. 1665-1676, 2009).*
Zhan et al (The pTiC58 tzs gene promotes high-efficiency root induction by agropine strain 1855 of Agrobaeterium rhizogenes. Plant Molecular Biology 14: 785-792, 1990).*
International rice genome sequencing project (The map-based sequence of the rice genome. Nature 436:793-800, 2005).*
Gelvin, "Plant Proteins Involved in Agrobacterium-Mediated Genetic Transformation," *Annu. Rev. Plytopathol*, 48(1):45-68 (2010).
Gelvin, "Agrobacterium in the Genomics Age," *Plant Physiology*, 150:1665-1676 (2009).
Guo et al., "Protein tolerance to random amino acid change," *Proc. Natl. Acad. Sci. USA*, 101: 9205-9210 (2004).
Hill et al., "Functional analysis of conserved histidines in ADP-glucose pyrophosphorylase from *Escherichia coli,*" *Biochem. Biophys. Res. Comm.*, 244:573-577 (1998).
Sardesai et al., Characterization of Arabidopsis mutants that are hyper-susceptible to Agrobacterium-mediated transformation (hat mutants), *28th Annual Crown Gall Conference*, p. 34, Abstract (2007).
Zhai et al., "A single-repeat R3-MYB transcription factor MYBC1 negatively regulates freezing tolerance in Arabidopsis," *Biochemical and Biophysical Research Communications*, 394(4):1018-1023 (2010).
Search Report and Written Opinion issued in Int'l App. No. PCT/US2011/059944 (2012).

* cited by examiner

*Primary Examiner* — Medina A Ibrahim
*Assistant Examiner* — Wayne Zhong
(74) *Attorney, Agent, or Firm* — Barnes & Thornburg LLP; Alice O. Martin

(57) ABSTRACT

A genetic screen for *Arabidopsis* mutants displaying a hyper-susceptible to *Agrobacterium* transformation (hat) phenotype was performed. The gene disrupted in the hat3 mutant encodes a putative myb-family transcription factor (MTF) that negatively regulates susceptibility to *Agrobacterium*-mediated transformation. Over-expression of an integrin-like protein results in plants that are hyper-susceptible to transformation. Manipulation of MTF, members of this protein family, and members of the integrin domain-like protein family for example At14a allows improved control of *Agrobacterium* transformation, including in crops.

2 Claims, 33 Drawing Sheets
Specification includes a Sequence Listing.

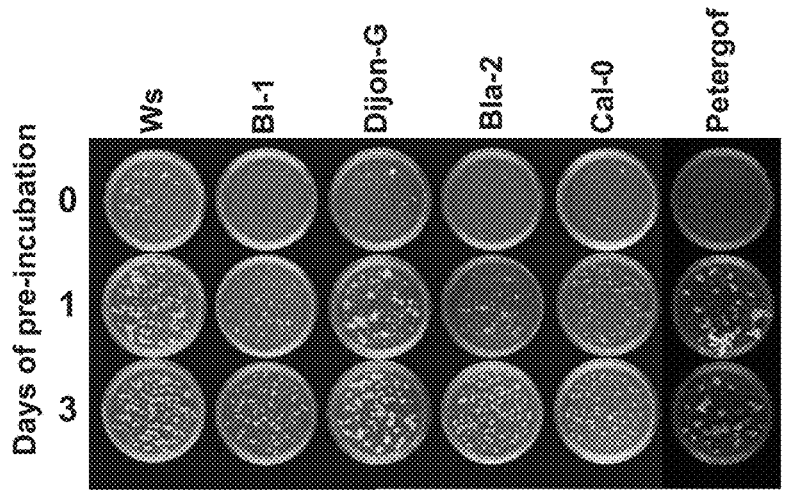
FIG. 2A
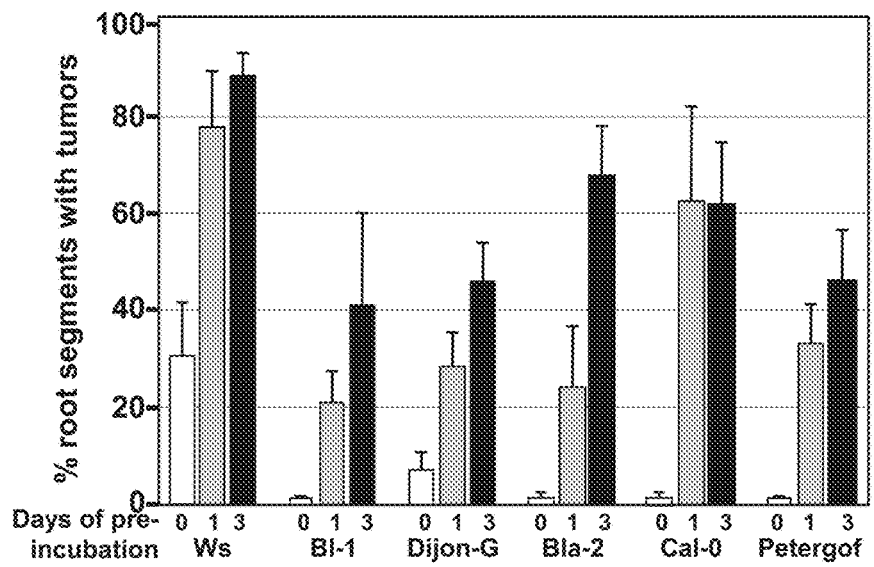
FIG. 2B
| | % GUS-positive root segments | | | | |
|---|---|---|---|---|---|
| | Bl-1 | Bla-2 | Cal-0 | Dijon-G | Petergof |
| No hormone pre-culture | 1.0 ± 0.4 | 1.2 ± 0.3 | 4.7 ± 1.2 | 5.4 ± 2.1 | 0.6 ± 0.6 |
| Hormone pre-culture | 8.2 ± 4.7 | 27.6 ± 10.0 | 32.1 ± 9.0 | 35.2 ± 20.0 | 41.3 ± 1.3 |
FIG. 2C

FIG. 16

Arabidopsis MTF sequences:

>At2g40970 (Myb transcription factor) cDNA (747 bp):

ATGAGAGAAGATAATCCAAATTGGTTCCTTAGATGGGAAGAAGAGCTTCCATCTCCAGAA
GAACTCATCCCTATCTCTCAAACCTTAATCACTCCTCATCTAGCTCTCGCTTTCCAAATC
GGAAGTCCTAATCATCATCTCGGATCAAAGAGAACCACCGCGATTTATCACCAGAAGCTT
CAATCCTCCACCACTCCAACAACTCCAACTCCAACTCCTCCACCGATGATGATGAATTCT
GATTTCGGCGGTGGCGATTCCACGGATCTTGGTTCAGGATCAATAGGAGGAGAGCCAGCA
AGAACGTTGAAACGGCCGCGTCTAGTGTGGACGCCTCAGCTACACAAACGTTTCGTGGAT
GCGGTTGGACACTTAGGGATCAAAAACGCAGTTCCAAAGACTATAATGCAGCTTATGAGC
GTTGAAGGATTGACTAGAGAGAACGTTGCGAGTCATCTTCAGAAATATCGTCTTTACCTT
AGGAGAATGCAAGGCGGGAACGGTAACGGAATCACTGGAGGACACGTCATCGTCTCTGAT
TCGGCTACTGATCGGCTATTTGCTAGCTCACCGGTTCCAGCTCATTTCTTGAGCCCGGAT
TACTTGATGCCGCCATTAGAGCATTCGTATATGGGGAAACATGTGATTACGCAGCAAAAC
CAAGTGGTTCGTAATCTGAGGTATGAAGATTCGGAATATGGTCATGGTAGTATGAAGATG
CTTAAGCTCTTCCCTGCCGGAAATTAA

>At2g40970 (Myb transcription factor) protein (248 aa):

MREDNPNWFLRWEEELPSPEELIPISQTLITPHLALAFQIGSPNHHLGSKRTTAIYHQKL
QSSTTPTTPTPTPPPMMMNSDFGGGDSTDLGSGSIGGEPARTLKRPRLVWTPQLHKRFVD
AVGHLGIKNAVPKTIMQLMSVEGLTRENVASHLQKYRLYLRRMQGGNGNGITGGHVIVSD
SATDRLFASSPVPAHFLSPDYLMPPLEHSYMGKHVITQQNQVVRNLRYEDSEYGHGSMKM
LKLFPAGN

FIG. 22A

Rice MTF ortholog sequences:

TGGTTTGGTGGGAAGAAGAATTGGTGCGTGTGTGTGTGAGGATGAGGGAGGAGGAGGA
ACCGAGCTGGTTCGCGCGGTGGGAGGAGCAGCTGCCGGCGCCGGACGAGCTGATGCCGCT
GTCGCAGTCGCTCATCACGCCCGATCTCGCGGTGGCCTTCGACATCCCGACGCATGGGGG
TGGTGGTGGTGGTGGGGTGGGCGGGGGTGTTGTCGGGGGTGATGGGGTGGGAGGTGGAGG
TGGTGGTGGTGGTGGTGGCGGTGGCGTGGGGGCAGGGGAGATGAACGGCGGGGCGTC
GTCGGCGGCCGGGTCGAGCGGCGGCGGCGGCGGCGGGGGAGGTGGCGACGAGCCGGCGCG
GACGCTCAAGAGGCCCCGGCTCGTGTGGACGCCGCAGCTGCACAAGCGGTTCGTCGACGC
GGTGGCGCACCTCGGCATCAAGAACGCCGTCCCCAAGACGATAATGCAGCTGATGAGCGT
CGATGGCCTCACGCGCGAGAACGTTGCGTCGCACCTCCAGAAGTACCGCCTCTACCTCAA
GCGCATGCAGGGGGTCGGCAACGGCGGCGGCGGCGGAGGAGGGGGCGGCGCCGGCGCCGG
CGGGAGCCACTCCTCCGGCTCCGGCACGGACGCCGCCACGGAGCACCTCTTCGCCACCGG
GCCGGTCCCCTTCCTCCCGCCCGGCCGCGCCCCGCCGGCGGGGACCCGTACCCGCCGTT
CGCCCC*CCATGGGCGGGC*ACCACCACCACCCGCCGCAGATCGGCCACTTCCACCACCACCC
CGCCGCGCGCCCGCTCGGCCACTACGGCTCCGGCCCGGGCGCCGGCTTCGACCACGGGTT
CCTCAGCCGGGCCGTCGCCGGAGGCGGCCCGCCCGTCGGCCCACCGGGGATGCACCACCG
CATGGTCGGCCCCGCCGCCGGCATGGCGATGATGGCGCCGTCCCCCTTCGCCGAAGAGCT
GGAGCTCGGATCCCGAGGAGGCGGCGGCGGCGGGCGCCGCGAGCTTACTCTGTTCCC
GACGACCGGCGACCACTGAGGCAAGCAGACAGACAGACC

MREEEEPSWFARWEEQLPAPDELMPLSQSLITPDLAVAFDIPTHGGGGGGVGGGVVGGD
GVGGGGGGGGGGGVGAGEMNGGASSAAGSSGGGGGGGGDEPARTLKRPRLVWTPQLH
KRFVDAVAHLGIKNAVPKTIMQLMSVDGLTRENVASHLQKYRLYLKRMQGVGNGGGGGGG
GGAGAGGSHSSGSGTDAATEHLFATGPVPFLPPGRAPAGGDPYPPFAPMGGHHHHPPQIG
HFHHHPAARPLGHYGSGPGAGFDHGFLSRAVAGGGPPVGPPGMHHRMVGPAAGMAMMAPS
PFAEELELGSRGGGGGGGRRELTLFPTTGDH

FIG. 22B

Brassica napus MTF ortholog sequences:

*CACCTTTCAAA*ATGAGAGAGGAAACTCCGAACTGGCTCGTCAGATGGGAGGAGGAGCTTC
CTTCGCCGGAAGAGCTCATACCCATCTCTCAAACCTTAATCACTCCTCACCTAGCTCTTG
CCTTCCAAATAGGAAGCCACAACAATCACTCCTCACCTAAGAGAACCGTCGCCATGTACC
ACCAGAAGCTCCAACCCGCCGCCACTCCATCTCCAACTATGATGAATACTGACTTCGGCG
GAGACTCATCGACTGATCTCGGCTCAGGAGGAGGAGGAGGAGGAGGAGACGAGCCAGCGA
GGACGCTGAAACGGCCGCGTTTAGTATGGACGCCGCAGCTGCACAAGCGTTTCGTGGACG
CGGTTGGTCACTTAGGGATCAAGAACGCAGTTCCTAAGACGATAATGCAGCTGATGAGCG
TTGAAGGGTTAACGAGAGAGAACGTTGCGAGTCATCTCCAGAAATACCGTCTCTACCTCA
GGAGAATGCAAGGCGGGAACGGTAACGGAGTCTCCGGAGGACACGTCATCGTCTCGGACT
CGGCCACTGACCGGCTCTTCGCGAGCTCGCCGGTTCCTGCGCATTTATTGAGCCATGAGT
ACTTGATGCCGTCTCCGTTGATGAACCCTTATTTAGGGAAACATGTGGTTACGCAGCAGA
ACCATGTGGTTCGTAATTTGAGGTATGAAGGTTCAGAGTATGGTAATGGAGATGGTGGTA
GGAAGGTTCTTAAGCTCTTCCCTGCTGGAAATTAATAATGAGATTTG

MREETSNWLIRCEEELPSPEELIPISQTLITPHLALAFQIGSHNNHSSPKRTVAMYHQKL
QPAATPTPTMMNSDFAVDSSTDLGSGGGGGGEEPARTLKRPRLVWTPQLHKRFVDAVGH
LGIKNAVPKTIMQLMSVEGLTRENVASHLQKYRLYLRRMQGGNDNGVSGGHVIVSDSATD
RLFASSPVPAHLLSHEYLMPSPLMNPYLGKHVVTQQNHVVRNLRYEGSEYGNGDGGRKVL
KLFPAGN

FIG. 22C

*Brassica rapa* MTF ortholog sequences:

CACCTTTCAAA<u>ATG</u>AGAGAGGAAACTCCGAACCGGCTCGTCAGATGGGAGGAGGAGCTTC
CTTCGCCGGAAGAGCTCATACCCATCTCTCAAACCTTAATCACCCCTCACCTAGCTCTTG
CCTTCCAAATAGGAAGCCACAACAATCACTCCTCACCTAAGAGAACCGTCGCCATGTACC
ACCAGAAGCTCCAGCCCGCCGCCACTCCAACTCCAACTATGATGAATTCTGACTTCGCGG
TAGACTCATCAACTGATCTCGGCTCAGGAGGAGGAGGAGGAGGAGGAGAAGAGCCAGCGA
GGACGCTGAAACGGCCGCGTTAGTATGGACGCCGCAGCTGCACAAGCGTTTCGTGGACG
CGGTTGGTCACTTAGGGATCAAGAACGCAGTTCCTAAGACGATAATGCAGCTTATGAGCG
TTGAAGGGTTAACGTGAGAGAACGTAGCGAGTCATCTCCAGAAATATCGTCTCTACCTAA
GGAGAATGCAAGGCGGGAACGGTAACGGAGTCTCCGGAGGACACGTCATCGTCTCAGACT
CGGCCACTGACCGGCTCTTCGCGAGTTCGCCGGTTCCGGCGCATTTATTGAGCCATGAGT
ACTTGATGCCGTCTCCGTTGATGAACCCTTATTTAGGGAAACATGTGGTTACGCAGCAGA
ACCATGTGGTTCGTAATTTGAGGTATGAAGGTTCAGAGTATGGTAATGGAGATGGTGGTA
GGAAGGTTCTTAAGCTCTTCCCTGCTGGAAAT<u>TAA</u>TAATGAGATTTG

<u>M</u>REETPNWLVRWEEELPSPEELIPISQTLITPHLALAFQIGSHNNHSSPKRTVAMYHQKL
QPAATPTPTMMNSDFAVDSSTDLGSGGGGGGEEPARTLKRPRLVWTPQLHKRFVDAVGH
LGIKNAVPKTIMQLMSVEGLTRENVASHLQKYRLYLRRMQGGNGNGVSGGHVIVSDSATD
RLFASSPVPAHLLSHEYLMPSPLMNPYLGKHVVTQQNHVVRNLRYEGSEYGNG

FIG. 22D

*Brassica oleracea* MTF ortholog sequences:

CACCTTTCAAA<u>ATG</u>AGAGAGGAAACTCCAAACTGGCTCATCAGATGTGAGGAGGAGCTTC
CTTCGCCGGAAGAGCTCATACCTATCTCTCAAACCTTAATCACTCCTCACCTAGCTCTTG
CTTTCCAAATAGGAAGCCACAACAATATTCACTCCTCGCCGAAGAGAACCGCCGCCATGT
ACCACCAGAAGCTCCAACCCGCCGCCACTCCATCTCCAACTATGATGAATCTGACTTCG
GCGGAGACTCATCGACTGATCTCGGCTCAGGAGGAGGAGGAGGAGGAGGAGACGAGCCAG
CGAGGACGCTGAAACGGCCGCGTTAGTATGGACGCCGCAGCTGCACAAGCGTTTCGTGG
ACGCGGTTGGTCACTTAGGGATCAAGAACGCAGTTCCTAAGACGATAATGCAGCTGATGA
GCGTTGAAGGGTTAACGAGAGAGAACGTTGCGAGTCATCTCCAGAAATACCGTCTCTACC
TCAGGAGAATGCAAGGCGGCAACGGTAACGGAGTCTCCGGAGGACACGTCATCGTCTCGG
ACTCGGCTACTGACCGGCTCTTCGCGAGCTCGCCGGTTCCGGCGCATTTATTGAGCCATG
AGTACTTGATGCCGTCACCGTTGATGAATCCTTATTTAGGGAAACATGTGGTAACACAGC
AGAACCATGTGGTTCGTAATTTGAGGTATGAAGATTCGGAGTATGGTAATGGAGATGGTG
GTAGGAAGGTTCTTAAGCTCTTTCCTGCTGGAAAT<u>TAA</u>TAATGAGATTTG

MREETPNWLIRCEEELPSPEELIPISQTLITPHLALAFQIGSHNNIHSSPKRTAAMYHQK
LQPAATPSPTMMNTDFGGDSSTDLGSGGGGGGGDEPARTLKRPRLVWTPQLHKRFVDAVG
HLGIKNAVPKTIMQLMSVEGLTRENVASHLQKYRLYLRRMQGGNGNGVSGGHVIVSDSAT
DRLFASSPVPAHLLSHEYLMPSPLMNPYLGKHVVTQQNHVVRNLRYEDSEYGNGDGGRKV
LKLFPAGN

FIG. 22E

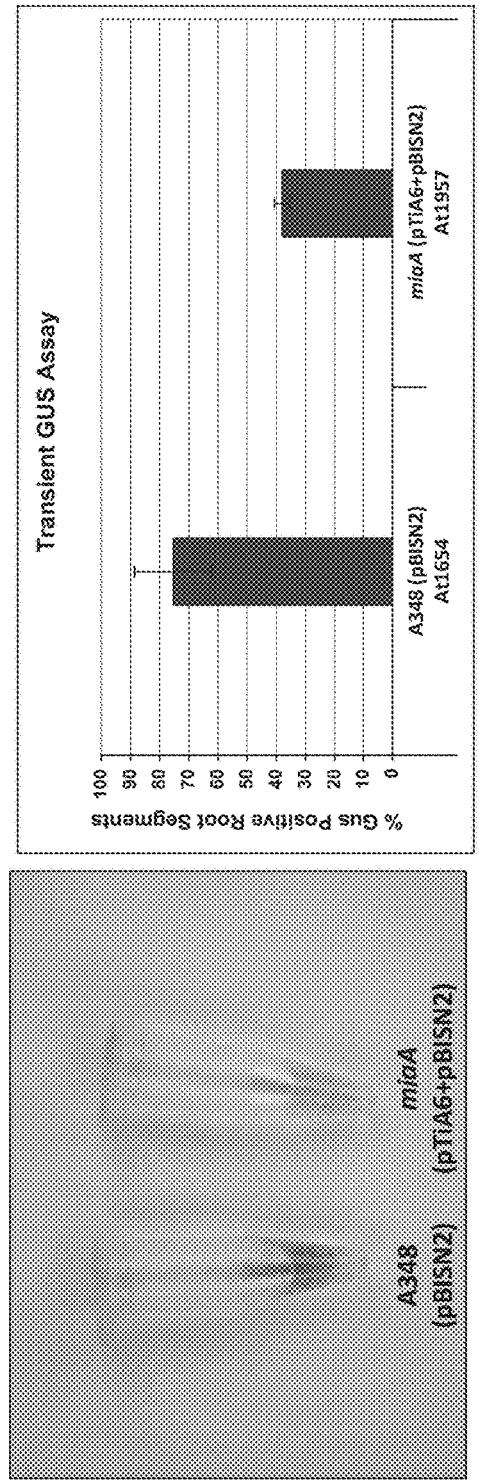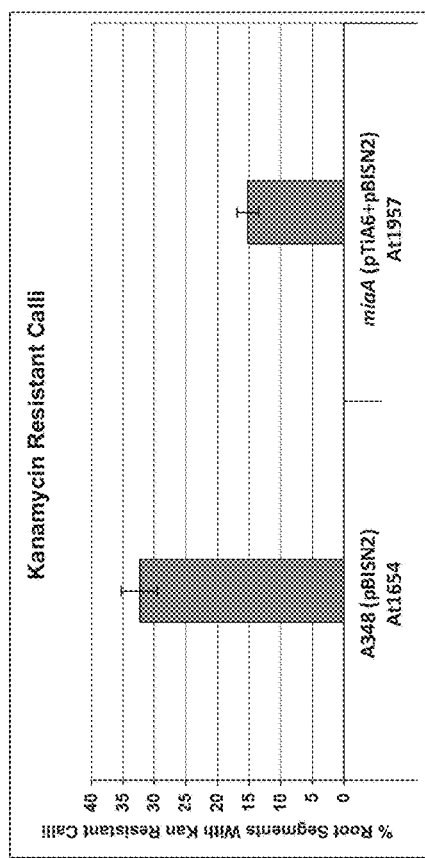
FIG. 30A
FIG. 30B
FIG. 30C

SEQUENCE LISTING

<160> NUMBER OF SEQ ID NOS: 83

<210> SEQ ID NO 1
<211> LENGTH: 7
<212> TYPE: PRT
<213> ORGANISM: Arabidopsis sp.

<400> SEQUENCE: 1

Ser His Ala Gln Lys Tyr Phe

```
<210> SEQ ID NO 2
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
ctaagctctc aagatcaaag gctta                                          25

<210> SEQ ID NO 3
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
actaaaacgc aaaacgaaag cggtt                                          25

<210> SEQ ID NO 4
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
gaagtacagt gtctggatcg gtggtt                                         26

<210> SEQ ID NO 5
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
attcctggac ctgcctcatc atactc                                         26

<210> SEQ ID NO 6
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
tgtggtttgg gttgctttca gctc                                           24

<210> SEQ ID NO 7
<211> LENGTH: 24
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic primer"

<400> SEQUENCE: 7
tcagtctcat tgccttcacg gctt                                            24

<210> SEQ ID NO 8
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
atggcaaaga ccctcaattc catctg                                          26

<210> SEQ ID NO 9
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
tatttcaacg accgtagcag tggc                                            24

<210> SEQ ID NO 10
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
tcctcaacat agtcgctatc ctccca                                          26

<210> SEQ ID NO 11
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
gagaagggaa acacactgta accgaac                                         27

<210> SEQ ID NO 12
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
ttgctgtggc ggtttctagt ggcttt                                          26

<210> SEQ ID NO 13

```
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
acatgccctc tggtgattag agaagc                                            26

<210> SEQ ID NO 14
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
ctggttccgg tttaatcgaa tgtccg                                            26

<210> SEQ ID NO 15
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
gatcgatgcc ggttcaagag actgaa                                            26

<210> SEQ ID NO 16
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
agctggtacc atggacacag cattgacc                                          28

<210> SEQ ID NO 17
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
ccgggagctc ttaccggttc tgcatg                                            26

<210> SEQ ID NO 18
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
```

```
cctcctcctt cctctactcc tcatgatt                                          28
```

<210> SEQ ID NO 19
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19

```
ttatgtatgt acggacggtt cgcaacgc                                          28
```

<210> SEQ ID NO 20
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20

```
tgagaagatg atgagaaaag ggaagctttc                                        30
```

<210> SEQ ID NO 21
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21

```
tgttagaatt tacaaccaca acagaggaag                                        30
```

<210> SEQ ID NO 22
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22

```
cagtgaagat agggtgtgct agggtt                                            26
```

<210> SEQ ID NO 23
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23

```
atcagtaagg gtactctccg acccaa                                            26
```

<210> SEQ ID NO 24
<211> LENGTH: 26
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic primer"

<400> SEQUENCE: 24
atctccacca cgtgccttac acttac                                       26

<210> SEQ ID NO 25
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
ttaaggaaag ccggacgaga acagag                                       26

<210> SEQ ID NO 26
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
tgggttcatg aggatgagtt tgagc                                        25

<210> SEQ ID NO 27
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
gactgttgat gtattagtgt ttgatcagc                                    29

<210> SEQ ID NO 28
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
cgaccaagga tataatatga agaagacgag                                   30

<210> SEQ ID NO 29
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
gtcaattagt gacgattacg cacgcc                                       26

-continued

```
<210> SEQ ID NO 30
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
tttagtcctt aggatgtctg agaaaccc                                         28

<210> SEQ ID NO 31
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
ggttagacca tcgatgcttg aggt                                             24

<210> SEQ ID NO 32
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
gcccacaatc cctaacattc cacaga                                           26

<210> SEQ ID NO 33
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
agtgtgtgat ccaaagctgt ctcagg                                           26

<210> SEQ ID NO 34
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
ggtttggtaa tgggcacaaa gaagag                                           26

<210> SEQ ID NO 35
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 35
cttgcacgta cccaccaaac tgatct                                        26

<210> SEQ ID NO 36
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
cggagatccg tttgattatt ctccac                                        26

<210> SEQ ID NO 37
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
tggaccgttg gattaactga aactcc                                        26

<210> SEQ ID NO 38
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
gtgattgtta tgagccgttg aatgcgg                                       27

<210> SEQ ID NO 39
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
tcacatagaa tcgatgcttc caaagtca                                      28

<210> SEQ ID NO 40
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
gtgagaagtg ctctgtgcaa gattgt                                        26

<210> SEQ ID NO 41
<211> LENGTH: 26
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 41
cggcgaaatc ttccaaatcc tcaagc                                        26

<210> SEQ ID NO 42
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
cgatggaagt aaagacggaa gaatcg                                        26

<210> SEQ ID NO 43
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
ggtgcggaga caacagtatt aacagac                                       27

<210> SEQ ID NO 44
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
aggtggtggc tttagcagca gta                                           23

<210> SEQ ID NO 45
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
acaccttcct cgattacacg atgtt                                         25

<210> SEQ ID NO 46
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
ttgatgtcga gggagatgat gacgtg                                        26
```

```
<210> SEQ ID NO 47
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
accatttaca ttcgtttctc acaaccaa                                           28

<210> SEQ ID NO 48
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
ccttcgcaga tcagatccga tactatt                                            27

<210> SEQ ID NO 49
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
actcctcatg aaacctacct accgga                                             26

<210> SEQ ID NO 50
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
gaagaagtgt tggcagagta acctcag                                            27

<210> SEQ ID NO 51
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
tctgtgcacg gactagcgga gaa                                                23

<210> SEQ ID NO 52
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<220> FEATURE:
<221> NAME/KEY: modified_base
<222> LOCATION: (1)..(1)
<223> OTHER INFORMATION: a, c, t, g, unknown or other

<400> SEQUENCE: 52
ntcastwtwt sgwgtt                                                         16

<210> SEQ ID NO 53
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 53
ngtcgaswga nawgaa                                                         16

<210> SEQ ID NO 54
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 54
wgtgnagwan canaga                                                         16

<210> SEQ ID NO 55
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
tggattgatg tgatatctag atccg                                               25

<210> SEQ ID NO 56
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 56
cccccaccca cgaggaacat cgtgg                                          25

<210> SEQ ID NO 57
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
ggaagatggc ttctacaaat gccat                                          25

<210> SEQ ID NO 58
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
ctcatcccta tctctcaaac c                                              21

<210> SEQ ID NO 59
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
ttccggcagg gaagagctta agcatctt                                       28

<210> SEQ ID NO 60
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
tggttcacgt agtgggccat cg                                             22

<210> SEQ ID NO 61
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
acggctcgag atgagagaag ataatcca                                       28

<210> SEQ ID NO 62
<211> LENGTH: 29

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
aaccactagt ttaatttccg gcagggaag                                    29

<210> SEQ ID NO 63
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
ctcatcccta tctctcaaac c                                            21

<210> SEQ ID NO 64
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
tctgaagatg actcgcaacg t                                            21

<210> SEQ ID NO 65
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
tcgcggccga gataagagac tc                                           22

<210> SEQ ID NO 66
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
tccggagaga ttcttcaacg acatcc                                       26

<210> SEQ ID NO 67
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67

```
acactagtgg cgcgccttta ccttaggaga atgc                            34
```

<210> SEQ ID NO 68
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68

```
acggatccat ttaaatttga tcctgacgac aaat                            34
```

<210> SEQ ID NO 69
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69

```
ccccaccggt atactacaaa atacctaaaa caaaatgt                        38
```

<210> SEQ ID NO 70
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70

```
ccaaggatcc gagatggaag ctcttcttc                                  29
```

<210> SEQ ID NO 71
<211> LENGTH: 247
<212> TYPE: PRT
<213> ORGANISM: Brassica napus
<400> SEQUENCE: 71

```
Met Arg Glu Glu Thr Ser Asn Trp Leu Ile Arg Cys Glu Glu Leu
1               5                   10                  15

Pro Ser Pro Glu Glu Leu Ile Pro Ile Ser Gln Thr Leu Ile Thr Pro
                20                  25                  30

His Leu Ala Leu Ala Phe Gln Ile Gly Ser His Asn His Ser Ser
                35                  40                  45

Pro Lys Arg Thr Val Ala Met Tyr His Gln Lys Leu Gln Pro Ala Ala
    50                  55                  60

Thr Pro Thr Pro Thr Met Met Asn Ser Asp Phe Ala Val Asp Ser Ser
65                  70                  75                  80

Thr Asp Leu Gly Ser Gly Gly Gly Gly Gly Gly Glu Glu Pro Ala
                85                  90                  95

Arg Thr Leu Lys Arg Pro Arg Leu Val Trp Thr Pro Gln Leu His Lys
                100                 105                 110

Arg Phe Val Asp Ala Val Gly His Leu Gly Ile Lys Asn Ala Val Pro
                115                 120                 125

Lys Thr Ile Met Gln Leu Met Ser Val Glu Gly Leu Thr Arg Glu Asn
        130                 135                 140
```

```
Val Ala Ser His Leu Gln Lys Tyr Arg Leu Tyr Leu Arg Arg Met Gln
145                 150                 155                 160

Gly Gly Asn Asp Asn Gly Val Ser Gly Gly His Val Ile Val Ser Asp
                165                 170                 175

Ser Ala Thr Asp Arg Leu Phe Ala Ser Ser Pro Val Pro Ala His Leu
            180                 185                 190

Leu Ser His Glu Tyr Leu Met Pro Ser Pro Leu Met Asn Pro Tyr Leu
        195                 200                 205

Gly Lys His Val Val Thr Gln Gln Asn His Val Val Arg Asn Leu Arg
    210                 215                 220

Tyr Glu Gly Ser Glu Tyr Gly Asn Gly Asp Gly Gly Arg Lys Val Leu
225                 230                 235                 240

Lys Leu Phe Pro Ala Gly Asn
            245

<210> SEQ ID NO 72
<211> LENGTH: 247
<212> TYPE: PRT
<213> ORGANISM: Brassica rapa

<400> SEQUENCE: 72

Met Arg Glu Glu Thr Pro Asn Trp Leu Val Arg Trp Glu Glu Leu
1               5                   10                  15

Pro Ser Pro Glu Glu Leu Ile Pro Ile Ser Gln Thr Leu Ile Thr Pro
            20                  25                  30

His Leu Ala Leu Ala Phe Gln Ile Gly Ser His Asn Asn His Ser Ser
        35                  40                  45

Pro Lys Arg Thr Val Ala Met Tyr His Gln Lys Leu Gln Pro Ala Ala
    50                  55                  60

Thr Pro Thr Pro Thr Met Met Asn Ser Asp Phe Ala Val Asp Ser Ser
65                  70                  75                  80

Thr Asp Leu Gly Ser Gly Gly Gly Gly Gly Glu Glu Pro Ala
                85                  90                  95

Arg Thr Leu Lys Arg Pro Arg Leu Val Trp Thr Pro Gln Leu His Lys
            100                 105                 110

Arg Phe Val Asp Ala Val Gly His Leu Gly Ile Lys Asn Ala Val Pro
        115                 120                 125

Lys Thr Ile Met Gln Leu Met Ser Val Glu Gly Leu Thr Arg Glu Asn
    130                 135                 140

Val Ala Ser His Leu Gln Lys Tyr Arg Leu Tyr Leu Arg Arg Met Gln
145                 150                 155                 160

Gly Gly Asn Gly Asn Gly Val Ser Gly Gly His Val Ile Val Ser Asp
                165                 170                 175

Ser Ala Thr Asp Arg Leu Phe Ala Ser Ser Pro Val Pro Ala His Leu
            180                 185                 190

Leu Ser His Glu Tyr Leu Met Pro Ser Pro Leu Met Asn Pro Tyr Leu
        195                 200                 205

Gly Lys His Val Val Thr Gln Gln Asn His Val Val Arg Asn Leu Arg
    210                 215                 220

Tyr Glu Gly Ser Glu Tyr Gly Asn Gly Asp Gly Gly Arg Lys Val Leu
225                 230                 235                 240

Lys Leu Phe Pro Ala Gly Asn
            245

<210> SEQ ID NO 73
```

```
<211> LENGTH: 248
<212> TYPE: PRT
<213> ORGANISM: Brassica oleracea

<400> SEQUENCE: 73
```

Met Arg Glu Glu Thr Pro Asn Trp Leu Ile Arg Cys Glu Glu Glu Leu
1               5                   10                  15

Pro Ser Pro Glu Glu Leu Ile Pro Ile Ser Gln Thr Leu Ile Thr Pro
                20                  25                  30

His Leu Ala Leu Ala Phe Gln Ile Gly Ser His Asn Ile His Ser
            35                  40                  45

Ser Pro Lys Arg Thr Ala Ala Met Tyr His Gln Lys Leu Gln Pro Ala
    50                  55                  60

Ala Thr Pro Ser Pro Thr Met Met Asn Thr Asp Phe Gly Gly Asp Ser
65                  70                  75                  80

Ser Thr Asp Leu Gly Ser Gly Gly Gly Gly Gly Gly Asp Glu Pro
                85                  90                  95

Ala Arg Thr Leu Lys Arg Pro Arg Leu Val Trp Thr Pro Gln Leu His
                100                 105                 110

Lys Arg Phe Val Asp Ala Val Gly His Leu Gly Ile Lys Asn Ala Val
            115                 120                 125

Pro Lys Thr Ile Met Gln Leu Met Ser Val Glu Gly Leu Thr Arg Glu
130                 135                 140

Asn Val Ala Ser His Leu Gln Lys Tyr Arg Leu Tyr Leu Arg Arg Met
145                 150                 155                 160

Gln Gly Gly Asn Gly Asn Gly Val Ser Gly Gly His Val Ile Val Ser
                165                 170                 175

Asp Ser Ala Thr Asp Arg Leu Phe Ala Ser Ser Pro Val Pro Ala His
            180                 185                 190

Leu Leu Ser His Glu Tyr Leu Met Pro Ser Pro Leu Met Asn Pro Tyr
        195                 200                 205

Leu Gly Lys His Val Val Thr Gln Gln Asn His Val Val Arg Asn Leu
    210                 215                 220

Arg Tyr Glu Asp Ser Glu Tyr Gly Asn Gly Asp Gly Gly Arg Lys Val
225                 230                 235                 240

Leu Lys Leu Phe Pro Ala Gly Asn
                245

```
<210> SEQ ID NO 74
<211> LENGTH: 248
<212> TYPE: PRT
<213> ORGANISM: Arabidopsis thaliana

<400> SEQUENCE: 74
```

Met Arg Glu Asp Asn Pro Asn Trp Phe Leu Arg Trp Glu Glu Glu Leu
1               5                   10                  15

Pro Ser Pro Glu Glu Leu Ile Pro Ile Ser Gln Thr Leu Ile Thr Pro
                20                  25                  30

His Leu Ala Leu Ala Phe Gln Ile Gly Ser Pro Asn His His Leu Gly
            35                  40                  45

Ser Lys Arg Thr Thr Ala Ile Tyr His Gln Lys Leu Gln Ser Ser Thr
    50                  55                  60

Thr Pro Thr Thr Pro Thr Pro Thr Pro Pro Met Met Met Asn Ser
65                  70                  75                  80

Asp Phe Gly Gly Gly Asp Ser Thr Asp Leu Gly Ser Gly Ser Ile Gly
                85                  90                  95

Gly Glu Pro Ala Arg Thr Leu Lys Arg Pro Arg Leu Val Trp Thr Pro
            100                 105                 110
Gln Leu His Lys Arg Phe Val Asp Ala Val Gly His Leu Gly Ile Lys
        115                 120                 125
Asn Ala Val Pro Lys Thr Ile Met Gln Leu Met Ser Val Glu Gly Leu
130                 135                 140
Thr Arg Glu Asn Val Ala Ser His Leu Gln Lys Tyr Arg Leu Tyr Leu
145                 150                 155                 160
Arg Arg Met Gln Gly Gly Asn Gly Asn Gly Ile Thr Gly Gly His Val
                165                 170                 175
Ile Val Ser Asp Ser Ala Thr Asp Arg Leu Phe Ala Ser Ser Pro Val
            180                 185                 190
Pro Ala His Phe Leu Ser Pro Asp Tyr Leu Met Pro Pro Leu Glu His
        195                 200                 205
Ser Tyr Met Gly Lys His Val Ile Thr Gln Gln Asn Gln Val Val Arg
210                 215                 220
Asn Leu Arg Tyr Glu Asp Ser Glu Tyr Gly His Gly Ser Met Lys Met
225                 230                 235                 240
Leu Lys Leu Phe Pro Ala Gly Asn
                245

<210> SEQ ID NO 75
<211> LENGTH: 331
<212> TYPE: PRT
<213> ORGANISM: Oryza sativa

<400> SEQUENCE: 75

Met Arg Glu Glu Glu Pro Ser Trp Phe Ala Arg Trp Glu Glu Gln
1               5                   10                  15
Leu Pro Ala Pro Asp Glu Leu Met Pro Leu Ser Gln Ser Leu Ile Thr
            20                  25                  30
Pro Asp Leu Ala Val Ala Phe Asp Ile Pro Thr His Gly Gly Gly Gly
        35                  40                  45
Gly Gly Gly Val Gly Gly Val Val Gly Gly Asp Gly Val Gly Gly
50                  55                  60
Gly Gly Gly Gly Gly Gly Gly Gly Gly Val Gly Ala Gly Glu
65                  70                  75                  80
Met Asn Gly Gly Ala Ser Ser Ala Ala Gly Ser Ser Gly Gly Gly Gly
                85                  90                  95
Gly Gly Gly Gly Gly Asp Glu Pro Ala Arg Thr Leu Lys Arg Pro Arg
            100                 105                 110
Leu Val Trp Thr Pro Gln Leu His Lys Arg Phe Val Asp Ala Val Ala
        115                 120                 125
His Leu Gly Ile Lys Asn Ala Val Pro Lys Thr Ile Met Gln Leu Met
130                 135                 140
Ser Val Asp Gly Leu Thr Arg Glu Asn Val Ala Ser His Leu Gln Lys
145                 150                 155                 160
Tyr Arg Leu Tyr Leu Lys Arg Met Gln Gly Val Gly Asn Gly Gly
                165                 170                 175
Gly Gly Gly Gly Gly Gly Ala Gly Ala Gly Ser His Ser Ser Gly
            180                 185                 190
Ser Gly Thr Asp Ala Ala Thr Glu His Leu Phe Ala Thr Gly Pro Val
        195                 200                 205
Pro Phe Leu Pro Pro Gly Arg Ala Pro Ala Gly Gly Asp Pro Tyr Pro

| | 210 | | | 215 | | | | 220 | | | |
|---|---|---|---|---|---|---|---|---|---|---|---|
| Pro | Phe | Ala | Pro | Met | Gly | Gly | His | His | His | Pro | Pro | Gln | Ile | Gly |
| 225 | | | | 230 | | | | 235 | | | | 240 |

His Phe His His His Pro Ala Ala Arg Pro Leu Gly His Tyr Gly Ser
                  245                 250               255

Gly Pro Gly Ala Gly Phe Asp His Gly Phe Leu Ser Arg Ala Val Ala
            260                 265                 270

Gly Gly Gly Pro Pro Val Gly Pro Pro Gly Met His His Arg Met Val
      275                 280                 285

Gly Pro Ala Ala Gly Met Ala Met Met Ala Pro Ser Pro Phe Ala Glu
     290                295                 300

Glu Leu Glu Leu Gly Ser Arg Gly Gly Gly Gly Gly Gly Arg Arg
305                 310                 315               320

Glu Leu Thr Leu Phe Pro Thr Thr Gly Asp His
            325                 330

```
<210> SEQ ID NO 76
<211> LENGTH: 747
<212> TYPE: DNA
<213> ORGANISM: Arabidopsis thaliana

<400> SEQUENCE: 76
atgagagaag ataatccaaa ttggttcctt agatgggaag aagagcttcc atctccagaa      60
gaactcatcc ctatctctca aaccttaatc actcctcatc tagctctcgc tttccaaatc     120
ggaagtccta atcatcatct cggatcaaag agaaccaccg cgatttatca ccagaagctt     180
caatcctcca ccactccaac aactccaact ccaactcctc accgatgatg atgaattct     240 gatttcggcg gtggcgattc cacggatctt ggttcaggat caataggagg agagccagca     300
agaacgttga acggccgcg tctagtgtgg acgcctcagc tacacaaacg tttcgtggat     360
gcggttggac acttagggat caaaaacgca gttccaaaga ctataatgca gcttatgagc     420
gttgaaggat tgactagaga aacgttgcg agtcatcttc agaaatatcg tctttacctt     480
aggagaatgc aaggcgggaa cggtaacgga atcactggag acacgtcat cgtctctgat     540 tcggctactg atcggctatt tgctagctca ccggttccag ctcatttctt gagcccggat     600
tacttgatgc cgccattaga gcattcgtat atggggaaac atgtgattac gcagcaaaac     660
caagtggttc gtaatctgag gtatgaagat tcggaatatg tcatggtag tatgaagatg     720 cttaagctct ccctgccgg aaattaa                                         747

<210> SEQ ID NO 77
<211> LENGTH: 1059
<212> TYPE: DNA
<213> ORGANISM: Oryza sativa

<400> SEQUENCE: 77
tggtttggtg ggaagaagaa ttggtgcgtg tgtgtgtgtg aggatgaggg aggaggagga      60
accgagctgg ttcgcgcggt gggaggagca gctgccggcg ccggacgagc tgatgccgct     120
gtcgcagtcg ctcatcacgc ccgatctcgc ggtggccttc gacatcccga cgcatggggg     180
tggtggtggt ggtggggtgg gcggggtgt tgtcggggt gatggggtgg gaggtggagg     240
tggtggtggt ggtggtggtg gcggtggcgt gggggcaggg gagatgaacg gcggggcgtc     300
gtcggcggcc gggtcgagcg gcggcggcgg cggcggggga ggtggcgacg agccggcgcg     360
gacgctcaag aggccccggc tcgtgtggac gccgcagctg cacaagcggt tcgtcgacgc     420
```

-continued

| | |
|---|---|
| ggtggcgcac ctcggcatca agaacgccgt ccccaagacg ataatgcagc tgatgagcgt | 480 |
| cgatggcctc acgcgcgaga acgttgcgtc gcacctccag aagtaccgcc tctacctcaa | 540 |
| gcgcatgcag ggggtcggca acggcggcgg cggcggagga gggggcggcg ccggcgccgg | 600 |
| cgggagccac tcctccggct ccggcacgga cgccgccacg gagcacctct tcgccaccgg | 660 |
| gccggtcccc ttcctcccgc ccggccgcgc ccccgccggc ggggacccgt accgccgtt | 720 |
| cgccccccatg ggcgggcacc accaccaccc gccgcagatc ggccacttcc accaccaccc | 780 |
| cgccgcgcgc ccgctcggcc actacggctc cggcccgggc gccggcttcg accacgggtt | 840 |
| cctcagccgg gccgtcgccg gaggcggccc gccgtcggc caccggggga tgcaccaccg | 900 |
| catggtcggc cccgccgccg gcatggcgat gatggcgccg tcccccttcg ccgaagagct | 960 |
| ggagctcgga tcccgaggag gcggcggcgg cggcgggcgc cgcgagctta ctctgttccc | 1020 |
| gacgaccggc gaccactgag gcaagcagac agacagacc | 1059 |

<210> SEQ ID NO 78
<211> LENGTH: 767
<212> TYPE: DNA
<213> ORGANISM: Brassica napus

<400> SEQUENCE: 78

| | |
|---|---|
| cacctttcaa aatgagagag gaaactccga actggctcgt cagatgggag gaggagcttc | 60 |
| cttcgccgga agagctcata cccatctctc aaacccttaat cactcctcac ctagctcttg | 120 |
| ccttccaaat aggaagccac aacaatcact cctcacctaa gagaaccgtc gccatgtacc | 180 |
| accagaaagct ccaacccgcc gccactccat ctccaactat gatgaatact gacttcggcg | 240 |
| gagactcatc gactgatctc ggctcaggag gaggaggagg aggaggagac gagccagcga | 300 |
| ggacgctgaa acgccgcgt ttagtatgga cgccgcagct gcacaagcgt ttcgtggacg | 360 |
| cggttggtca cttagggatc aagaacgcag ttcctaagac gataatgcag ctgatgagcg | 420 |
| ttgaagggtt aacgagagag aacgttgcga gtcatctcca gaaataccgt ctctacctca | 480 |
| ggagaatgca aggcgggaac ggtaacggag tctccggagg acacgtcatc gtctcggact | 540 |
| cggccactga ccggctcttc gcgagctcgc cggttcctgc gcatttattg agccatgagt | 600 |
| acttgatgcc gtctccgttg atgaacccctt atttagggaa acatgtggtt acgcagcaga | 660 |
| accatgtggt tcgtaatttg aggtatgaag gttcagagta tggtaatgga gatggtggta | 720 |
| ggaaggttct taagctcttc cctgctggaa attaataatg agatttg | 767 |

<210> SEQ ID NO 79
<211> LENGTH: 767
<212> TYPE: DNA
<213> ORGANISM: Brassica rapa

<400> SEQUENCE: 79

| | |
|---|---|
| cacctttcaa aatgagagag gaaactccga accggctcgt cagatgggag gaggagcttc | 60 |
| cttcgccgga agagctcata cccatctctc aaacccttaat caccccctcac ctagctcttg | 120 |
| ccttccaaat aggaagccac aacaatcact cctcacctaa gagaaccgtc gccatgtacc | 180 |
| accagaaagct ccagcccgcc gccactccaa ctccaactat gatgaattct gacttcgcgg | 240 |
| tagactcatc aactgatctc ggctcaggag gaggaggagg aggaggagaa gagccagcga | 300 |
| ggacgctgaa acgccgcgcgt ttagtatgga cgccgcagct gcacaagcgt ttcgtggacg | 360 |
| cggttggtca cttagggatc aagaacgcag ttcctaagac gataatgcag cttatgagcg | 420 |
| ttgaagggtt aacgtgagag aacgtagcga gtcatctcca gaaatatcgt ctctacctaa | 480 |

```
ggagaatgca aggcgggaac ggtaacggag tctccggagg acacgtcatc gtctcagact    540
cggccactga ccggctcttc gcgagttcgc cggttccggc gcatttattg agccatgagt    600
acttgatgcc gtctccgttg atgaaccctt atttagggaa acatgtggtt acgcagcaga    660
accatgtggt tcgtaatttg aggtatgaag gttcagagta tggtaatgga gatggtggta    720
ggaaggttct taagctcttc cctgctggaa attaataatg agatttg                 767
```

<210> SEQ ID NO 80
<211> LENGTH: 770
<212> TYPE: DNA
<213> ORGANISM: Brassica oleracea

<400> SEQUENCE: 80

```
cacctttcaa aatgagagag gaaactccaa actggctcat cagatgtgag gaggagcttc     60
cttcgccgga agagctcata cctatctctc aaaccttaat cactcctcac ctagctcttg    120 cttttccaaat aggaagccac aacaatattc actcctcgcc gaagagaacc gccgccatgt    180
accaccagaa gctccaaccc gccgccactc catctccaac tatgatgaat actgacttcg    240
gcggagactc atcgactgat ctcggctcag gaggaggagg aggaggagga acgagccag    300 cgaggacgct gaaacggccg cgtttagtat ggacgccgca gctgcacaag cgtttcgtgg    360
acgcggttgg tcacttaggg atcaagaacg cagttcctaa gacgataatg cagctgatga    420
gcgttgaagg gttaacgaga gagaacgttg cgagtcatct ccagaaatac cgtctctacc    480
tcaggagaat gcaaggcggc aacggtaacg gagtctccgg aggacacgtc atcgtctcgg    540
actcggctac tgaccggctc ttcgcgagct cgccggttcc ggcgcattta ttgagccatg    600
agtacttgat gccgtcaccg ttgatgaatc cttatttagg gaaacatgtg gtaacacagc    660
agaaccatgt ggttcgtaat ttgaggtatg aagattcgga gtatggtaat ggagatggtg    720
gtaggaaggt tcttaagctc tttcctgctg gaaattaata atgagatttg               770
```

<210> SEQ ID NO 81
<211> LENGTH: 385
<212> TYPE: PRT
<213> ORGANISM: Arabidopsis sp.

<400> SEQUENCE: 81

```
Met Val Leu Ser Lys Glu Asn Met Leu Lys Tyr Ser Ala His Leu Arg
1               5                   10                  15

Ala Tyr Asn Ser Ala Cys Gly Asp His Pro Glu Leu Lys Ser Phe Asp
            20                  25                  30

Ser Glu Leu Gln Gln Lys Thr Ser Asn Leu Ile Asn Ser Phe Thr Ser
        35                  40                  45

Asp Ala Lys Thr Gly Leu Val Pro Leu Pro Gln His Ala Ala Tyr Lys
    50                  55                  60

Glu Phe Thr Lys His Leu Ala Glu Val Asn Gln Gln Val Ser Asp Tyr
65                  70                  75                  80

Ile Ile Gly Tyr Gly Glu Val Val Trp Glu Asn Ser Thr Leu Arg Ser
                85                  90                  95

Leu Val Glu Thr Tyr Phe Glu Ser Ala Lys Lys Thr Leu Asp Ile Ala
            100                 105                 110

Glu Asn Val Thr Glu Tyr Val Asp Glu Ala Lys Arg Gly Glu Arg Tyr
        115                 120                 125

Ile Val Ala Ala Val Ala Gln Phe Glu Lys Asp Lys Glu Asn Asp Val
    130                 135                 140
```

Gly Lys Lys Thr Lys Arg Tyr Glu Asn Thr Leu Arg Glu Leu Lys Lys
145                 150                 155                 160

Phe Glu Ala Met Gly Asn Pro Phe Asp Gly Asp Lys Phe Thr Thr Leu
                165                 170                 175

Phe Lys Leu Met His Lys Glu Gln Ser Leu Leu Glu Arg Val Arg
            180                 185                 190

Glu Thr Lys Glu Lys Leu Asp Glu Leu Lys Asn Ile Glu Met Glu
        195                 200                 205

Ile Ser Ser Arg Lys Lys Trp Ser Ile Ile Ser Asn Val Leu Phe Ile
210                 215                 220

Gly Ala Phe Val Ala Val Ala Val Gly Ser Met Val Leu Val Cys Thr
225                 230                 235                 240

Gly Val Gly Ala Gly Val Gly Val Ala Gly Leu Leu Ser Leu Pro Leu
                245                 250                 255

Ile Ala Ile Gly Trp Val Gly Val His Thr Ile Leu Glu Asn Lys Ile
                260                 265                 270

Gln Ala Arg Glu Lys Gln Glu Ala Leu Lys Lys Ala His Arg Ile
            275                 280                 285

Ala Asn Glu Met Asp Lys Gly Met Glu Thr Asp Lys Val Asp Met Asn
290                 295                 300

Ser Ile Ser Gly Lys Val His Ala Leu Lys Ser Lys Ile Thr Ser Met
305                 310                 315                 320

Leu Asn Ala Val Lys Asp Ala Thr Glu Asp Gly Ala Asn Glu Val Asp
                325                 330                 335

Thr Lys Gln Val Met Glu Thr Leu Thr Gly Asp Val Val Glu Leu Thr
                340                 345                 350

Glu Asp Ile Lys Ala Val Gly Asp Asp Val Ala Lys Tyr Ser Lys Met
            355                 360                 365

Ile Glu Glu Thr Ser Tyr His Val Leu Gln Lys Ile Thr Gly Ser Gly
            370                 375                 380

Lys
385

<210> SEQ ID NO 82
<211> LENGTH: 280
<212> TYPE: PRT
<213> ORGANISM: Arabidopsis sp.

<400> SEQUENCE: 82

Met Glu Thr Leu Lys Ile Phe Glu Thr Val Thr Gln Cys Val His Glu
1               5                   10                  15

Ala Lys Arg Gly Gln Arg Tyr Ile Lys Ala Ala Val Ala Gln Phe Lys
                20                  25                  30

Lys Asp Ser Glu Glu Lys Asp Val Gly Val Lys Lys Arg Tyr Gly
            35                  40                  45

Lys Thr Leu Glu Glu Leu Met Lys Phe Lys Ala Met Gly Asn Pro Phe
        50                  55                  60

Asp Asp Gly Leu Leu Lys Thr Gln Phe Glu Leu Met Asn Lys Gln Gln
65                  70                  75                  80

Glu Ser Leu Phe Asp Arg Val Thr Glu Thr Lys Glu Arg Ile Ala Lys
                85                  90                  95

Glu Ile Glu Glu Val Gln Lys Arg Ile Ser Asn Val Asn Thr Ala Thr
            100                 105                 110

Ile Val Ser His Val Val Phe Gly Ala Ala Ala Phe Gly Tyr Ala Ala

```
            115                 120                 125
Gly Cys Ile Ala Leu Met Cys Thr Gly Val Gly Ala Pro Leu Gly Ala
        130                 135                 140

Gly Met Val Thr Leu Leu Pro Val Ile Val Val Gln Trp Val Gly Val
145                 150                 155                 160

Asn Tyr Val Leu Asn Asn Ser Leu Glu Ala Leu Gln Lys Gln Leu Lys
                165                 170                 175

Ala Leu Asn Lys Val Lys Pro Ile Pro Glu Arg Ile Thr Glu Gly Met
            180                 185                 190

Glu Ala Asp Lys Glu Gly Met Lys Ser Val Pro Glu Gln Val Asp Glu
        195                 200                 205

Leu Lys Asp Gln Ile Ser Ser Leu Leu Gln Thr Val Asp Asp Ala Ile
    210                 215                 220

Gly Ser Glu Gly Asp Glu Val Asp Val Lys Leu Asp Met Glu Ser Leu
225                 230                 235                 240

Glu Asp Asp Val Lys Thr Leu Thr Thr Lys Ile Thr Glu Val Gly Glu
                245                 250                 255

Thr Val Ala Lys Tyr Ser Lys Ile Ile Lys Glu Ala Arg Leu His Val
            260                 265                 270

Leu Glu Lys Ile Thr Gly Thr Gly
        275                 280

<210> SEQ ID NO 83
<211> LENGTH: 374
<212> TYPE: PRT
<213> ORGANISM: Arabidopsis sp.

<400> SEQUENCE: 83

Met Ala Leu Ser Lys Asp Leu Met Leu Lys Cys Ser Glu Asp Met Met
1               5                   10                  15

Ser Ala Cys Lys Ser Ala Cys Glu Glu His Pro Lys Leu Lys Ser Phe
            20                  25                  30

Asp Ala Ser Leu Gln Gln Arg Thr Asn Lys Met Ile Asp Ser Leu Thr
        35                  40                  45

Val Glu Asp Lys Asn Gly Ser Ser Ser Pro His Asp Ala His Met Glu
    50                  55                  60

Leu Ser Lys His Leu Val Glu Val Thr Gln Gly Val Ala Asp Phe Ile
65                  70                  75                  80

Thr Glu Ile Glu Asp Asp Val Trp Asp Asn Gln Ala Leu Lys Tyr Leu
                85                  90                  95

Val Leu Ala Tyr Phe Glu Asn Thr Lys Lys Thr Leu Glu Ile Phe Lys
            100                 105                 110

Thr Ile Glu Asn Cys Val Glu Asn Ala Glu Met Gly Gln Leu Leu Ile
        115                 120                 125

Arg Glu Ala Leu Ala Glu Phe Glu Lys Glu Ser Ala Glu Lys Asp Val
    130                 135                 140

Gly Gly Lys Lys Lys Tyr Glu Lys Thr Leu Glu Asp Leu Lys Ser
145                 150                 155                 160

Phe Lys Glu Met Gly Asp Pro Phe Asp Gly Lys Val Leu Thr Thr Gln
                165                 170                 175

Phe Glu Arg Ile Lys Lys Gln Gln Glu Ser Leu Leu Glu Glu Val Ser
            180                 185                 190

Glu Thr Arg Lys Lys Ile Gln Asp Glu Ile Ser Asn Leu Glu Lys Lys
        195                 200                 205
```

```
Thr Leu Ile Thr Asn Val Val Phe Gly Ala Ala Phe Ala Ile Val Ala
    210                 215                 220

Val Ala Ser Ile Ala Leu Ile Ala Thr Gly Val Gly Ala Ala Ala Gly
225             230                 235                     240

Phe Gly Ala Leu Ala Ala Pro Leu Leu Ala Ala Gly Trp Ala Gly Val
            245                 250                 255

Tyr Thr Thr Leu Asp Lys Lys Asp Ala Leu Asn Lys Gln Leu Glu
            260             265             270

Gly Leu Lys Lys Val Glu Glu Ile Glu Glu Ser Val Glu Lys Gly Ile
        275             280                 285

Lys Thr Asn Glu Glu Ala Thr Glu Thr Val Ser Ile Leu Val Asp Gly
    290                 295                 300

Leu Glu Asp Arg Ile Lys Asn Met Leu Lys Leu Val Asp Asn Ala Ile
305             310             315                     320

Asp His Glu Asp Asn Glu Ala Ala Thr Arg Ile Val Leu Thr Gln Ile
                325                 330                 335

Ser Lys Lys Val Glu Lys Leu Thr Lys Lys Ile Thr Glu Val Gly Glu
            340             345                 350

Ser Val Glu Asp His Ser Lys Leu Ile Ala Lys Ala Arg Leu Gln Val
        355             360                 365

Leu Gln Lys Ile Asn Arg
    370
```

METHODS AND COMPOSITIONS TO REGULATE PLANT TRANSFORMATION SUSCEPTIBILITY

CROSS REFERENCE TO RELATED APPLICATIONS

This application is a Divisional of co-pending U.S. application Ser. No. 13/884,480, filed May 9, 2013, which is a U.S. nationalization under 35 U.S.C. § 371 of International Application No. PCT/US2011/059944, filed Nov. 9, 2011, which claims the benefit of priority under 35 U.S.C. § 119(e) to U.S. provisional application No. 61/412,684, filed Nov. 11, 2010, and 61/552,127, filed Oct. 27, 2011. The disclosures of the referenced applications are incorporated herein by reference in their entireties.

This invention was made with government support under Grant No. 13-CPBR-3-0149 awarded by the United States Department of Agriculture. The United States Government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 14, 2016, is named 246654_SEQ_ST25.txt and is 44,505 bytes in size.

BACKGROUND

A myb transcription factor designated MTF is disclosed that negatively regulates plant transformation susceptibility. An integrin domain-like protein (which is under negative regulation by MTF) is involved in *Agrobacterium* attachment to plant cells and, thus, is a positive mediator of transformation: plants over-expressing the integrin domain-like protein are more susceptible to transformation, whereas plants mutant for the integrin domain-like protein are less susceptible. Manipulation of these elements allows improved control of Agrobacterial transformation of plants, including in crops.

*Agrobacterium*-mediated plant transformation forms the basis for the modern agricultural biotechnology industry.

*Agrobacterium tumefaciens* causes the disease crown gall and genetically transforms numerous plant, fungal and animal species. Virulent Agrobacteria harbor a tumor-inducing (Ti) plasmid containing virulence (vir) genes required by the pathogen for transport of transferred (T-) DNA and virulence effector proteins to host cells. Induction of vir genes, processing of T-DNA from the Ti-plasmid, attachment of the bacteria to plants, and subsequent transfer of T-DNA and Vir proteins to host cells are complex processes. Numerous studies have elucidated the events governing these processes in the bacterium, but relatively little is known about the plant contribution to transformation.

Although *Agrobacterium* has a broad host range, many economically important plants remain recalcitrant to transformation. Scientists have used a variety of techniques to identify plant genes that are involved in *Agrobacterium*-mediated transformation. Among these, forward and reverse genetic screens revealed more than 125 *Arabidopsis* and tobacco genes involved in transformation. Collectively these lines, designated "rat" (resistant to *Agrobacterium* transformation), reflected their attenuated response to transformation. The genes identified represent steps necessary for successful transformation, including bacterial attachment/biofilm formation, T-DNA and Vir protein transfer, cytoplasmic trafficking and nuclear targeting of the Vir protein/T-DNA complex (T-complex), Vir protein removal, T-DNA integration, and transgene expression. However, none of these mutants identify genes globally affecting plant transformation susceptibility.

SUMMARY

A myb transcription factor designated MTF is disclosed that negatively regulates plant transformation susceptibility. An integrin domain-like protein (which is under negative regulation by MTF) is involved in *Agrobacterium* attachment to plant cells and, thus, is a positive mediator of transformation: plants over-expressing the integrin domain-like protein are more susceptible to transformation, whereas plants mutant for the integrin domain-like protein are less susceptible. Manipulation of these elements allows improved control of Agrobacterial transformation of plants, including crops.

*Agrobacterium*-mediated transformation is the most widely used technique for generating transgenic plants. However, transformation remains a major limitation to enhancement of major crops through biotechnology. The first known regulator of plant transformation susceptibility is described herein. An *Arabidopsis* myb transcription factor (MTF) negatively regulates plant transformation susceptibility. DNA insertions in the mtf gene made *Arabidopsis* lines hyper-susceptible to transformation by several *Agrobacterium* strains. In addition, RNAi targeting of MTF in the transformation-recalcitrant *Arabidopsis* ecotype Bl-1 resulted in increased transformation susceptibility accompanied by increased bacterial attachment to roots.

Transcriptional profiling of wild-type and mtf mutant plants revealed down-regulation of the WRKY48 transcription factor gene in the mtf mutants. Mutation of WRKY48 resulted in hyper-susceptibility to transformation, as did over-expression of two genes that were up-regulated in the mtf mutants [At1g50060 or At5g15725]. *Arabidopsis* roots inoculated with Agrobacteria expressing a trans-zeatin secretion (TZS) gene showed decreased expression of MTF and a corresponding increase in transformation susceptibility.

When the *Arabidopsis* myb gene is overexpressed in *Arabidopsis*, the plants grow much larger, the roots are longer, and the leaves are darker green. This may be a useful agronomic trait if this is confirmed for crop plants grown in the field.

An integrin domain-like protein (which is under negative regulation by MTF) is involved in *Agrobacterium* attachment to plant cells and, thus, is a positive mediator of transformation: plants over-expressing the integrin domain-like protein are more susceptible to transformation, whereas plants mutant for the integrin domain-like protein are less susceptible. Over-expression of the At14a gene produces an integrin domain-like protein in the *Arabidopsis* ecotype Bl-1 increased bacterial binding to roots, and also increases root transformation. This ecotype is highly recalcitrant to *Agrobacterium*-mediated transformation, and binds bacteria poorly to roots.

Increasing *Agrobacterium*-mediated transformation of recalcitrant species, and tissues of these species, is achieved by over-expressing of the At14a gene. In particular, some tissues that are easy to regenerate but difficult to transform may not bind *Agrobacterium* well, and over-expressing At14a may improve binding and transformation.

Myb transcription factors and integrin-like proteins, alone or in combination are useful, to achieve a desired effect on transformation by manipulating Agrobacterial transformation in a plant. For example, the integrin-like protein is designated At14a, and the myb transcription factor is MTF.

BRIEF DESCRIPTION OF THE DRAWINGS

FIGS. 1A-1I. Expression of MTF influences plant susceptibility to *Agrobacterium*-mediated transformation. 1A Percentage of root segments developing tumors in plants inoculated with *A. tumefaciens* A208. 1B Representative plates showing increased transformation susceptibility of mutants. 1C Map of T-DNA insertion positions in MTF. Numbers indicate nucleotide positions; +1 indicates translation start site 1D Relative MTF transcript levels in wild-type, hat3, and mtf1-4 (previously mtf2) roots 1E Transformation susceptibility of root segments from wild-type, mtf1-4, and mtf1-4 plants complemented with a MTF cDNA. Numbers indicate individual T2 generation lines 1F Relative MTF transcript levels in roots of wild-type, mtf1-4 (previously mtf2), and complemented mtf1-4 (previously mtf2) lines 1, 2, 3, and 5 as in 1E 1G-1I, Down-regulation of MTF by RNAi in roots of ecotype Bl-1 increases transformation susceptibility 1G and attachment of Agrobacteria to roots 1I. Numbers indicate individual T2 generation MTF-RNAi lines and empty vector (EV) line. 1H Relative MTF transcript levels in roots of Bl-1 and lines 2, 9, 10, and EV. 1I Attachment of GFP-tagged *A. tumefaciens* A208 to root segments of Col-0, Bl-1 and MTF-RNAi lines 2, 8, 9, 10, and EV. Error bars in all figures indicate s.e.m. from 3 (for relative transcript levels) or 5 (for percentage of roots developing tumors) replicates.

FIGS. 2A-2C. Phytohormone pre-treatment of *Arabidopsis* roots increases susceptibility to *Agrobacterium*-mediated transformation. 2A Representative plates showing tumors on root segments from *Arabidopsis* ecotypes following 0, 1, and 3 days of phytohormone pre-treatment before infection with *A. tumefaciens* A208. 2B Percentage of root segments developing tumors. 2C Transient transformation after 3 d phytohormone pre-treatment of root segments followed by infection with *A. tumefaciens* At849.

Figure 16:
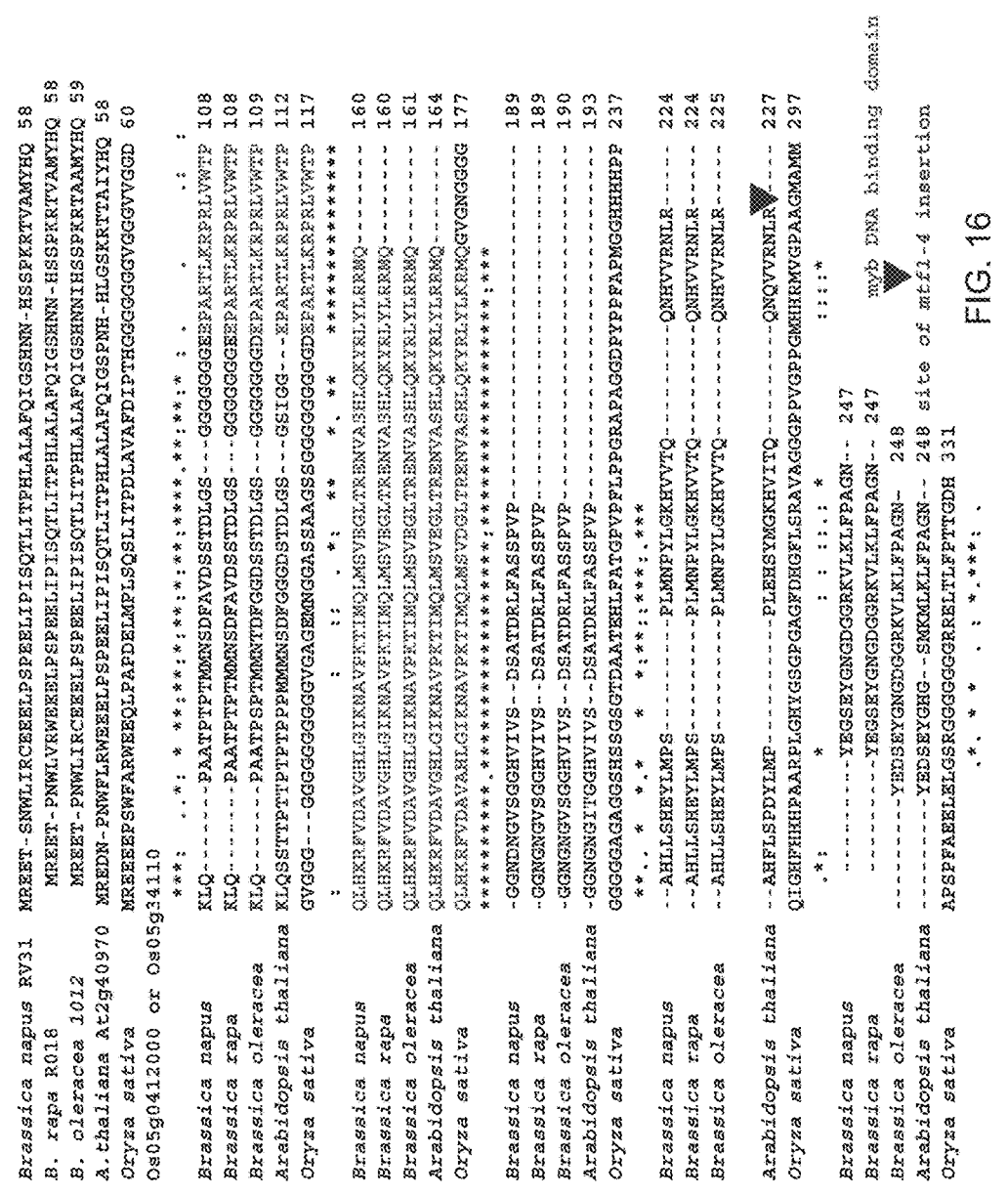

FIG. 16. *Arabidopsis* and crop myb transcription factors are highly homologous. FIG. 16 discloses SEQ ID NOS 71-75, respectively, in order of appearance.

FIGS. 22A-22E. MTF Sequences: Double underlined nucleotides indicate start codons; single underlined nucleotides indicate stop codons; italic bold nucleotides indicate part of the 5'- and 3' untranslated sequences on the cDNA clones: 22A *Arabidopsis* MTF and MTF (SEQ ID NOS 76 and 74, respectively, in order of appearance); 22B-22E orthology sequences [Rice, *Brassica napus*, *Brassica rapa*, *Brassica oleracea*] (SEQ ID NOS 77, 75; 78, 71; 79, residues 1-233 of SEQ ID NO: 72; 80 and 73, respectively, in order of appearance).

FIGS. 30A-30C. *Arabidopsis* plants infected with an *A. tumefaciens* miaA mutant show decreased transformation susceptibility. 30A binding; 30B shows a transient GUS assay; 30C shows kanamycin resistant calli.

DETAILED DESCRIPTION

A genetic screen for *Arabidopsis* mutants displaying a hyper-susceptible to *Agrobacterium* transformation (hat) phenotype was performed. The gene disrupted in the hat3 mutant encodes a putative myb-family transcription factor (MTF) that negatively regulates susceptibility to *Agrobacterium*-mediated transformation.

Identification and Characterization of Mtf Mutants

Figure 1A:
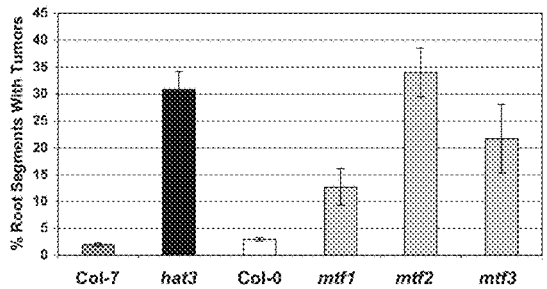
Figure 1B:
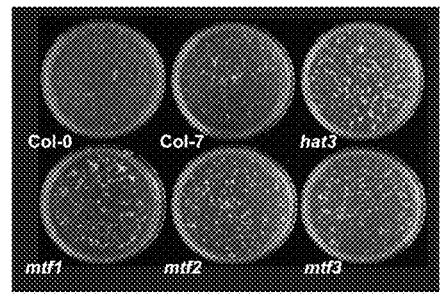
Figure 1C:
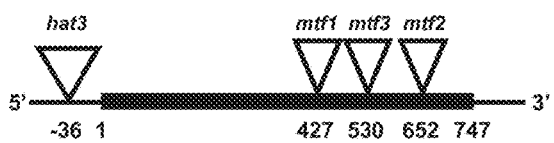

To identify mutants with increased susceptibility to *Agrobacterium*-mediated transformation, ~4000 mutagenized plants were screened from an *Arabidopsis* T-DNA activation-tagged library (Weigel, 2000). The mutant hat3 displayed a ~10-fold increase in transformation susceptibility (FIG. 1A, 1B). TAIL-PCR (Liu et al., 1995) was used to identify the T-DNA/plant junction in hat3, and it was discovered that the T-DNA had inserted into the 5' untranslated region of a putative myb transcription factor (MTF) gene, At2g40970, 36 bp upstream of the start codon (FIG. 1C). MTF has a single Myb DNA-binding domain of the SHAQKYF (SEQ ID NO: 1) type that is unique to plants, and is a member of a five-gene family (Hazen et al., 2005). The DNA-binding domain is similar to those found in proteins associated with two-component signal transduction systems (Hwang et al., 2002), the B-type *Arabidopsis* response regulators (ARRs), GOLDEN2-LIKE (GLK), and PRR2 (Hazen et al, 2005).

Figure 1D:
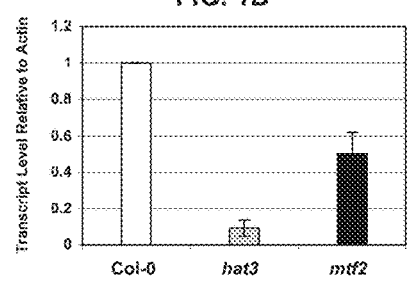

Homozygous mutant plants were not recoverable from self-fertilized progeny of hat3, suggesting that complete disruption of MTF may be lethal. Self-fertilization of three additional T-DNA MTF insertion mutants, SALK_072082 (mtf1), SALK_072083 (mtf1-4), and SALK_102624 (mtf3), resulted in a homozygous mutant only for mtf1-4 (previously mtf2). The insertion in mtf1-4 (previously mtf2) permitted expression of ~85% of the MTF open reading frame, indicating that the majority of MTF protein is essential for *Arabidopsis* viability. Homozygous mtf1-4 (previously mtf2) plants showed an ~11-fold increase in transformation susceptibility. Heterozygous mtf1 and mtf3 mutants displayed 4-7-fold increased transformation susceptibility (FIG. 1A, 1B). Thus, all four mtf mutant lines displayed a hat phenotype, highlighting the importance of MTF in transformation. Quantitative real-time RT-PCR assays revealed that MTF transcript levels decreased 2-fold in mtf1-4 (previously mtf2) and >12-fold in hat3 (FIG. 1D), demonstrating that transformation susceptibility negatively correlates with MTF transcript levels.

Figure 7:
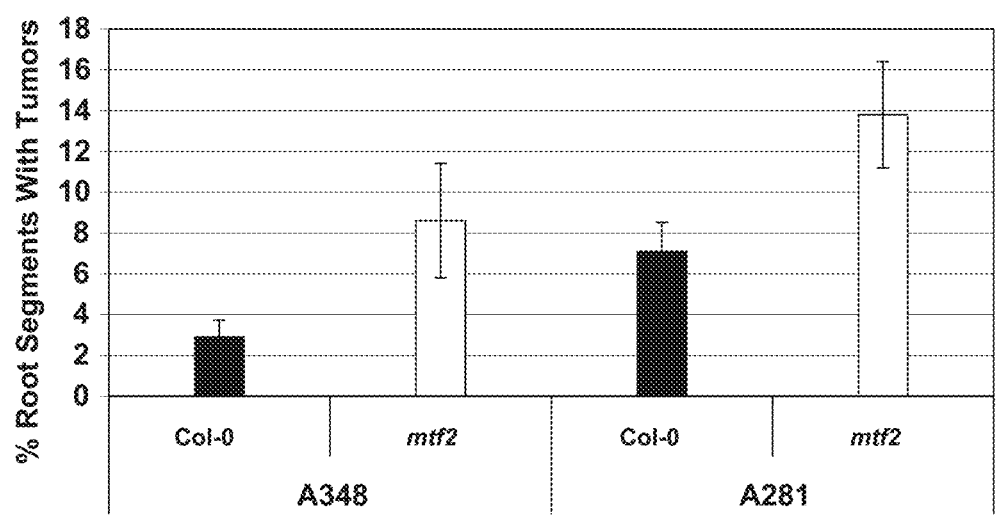
FIG. 7. Mutation of MTF increases root transformation susceptibility to multiple *Agrobacterium* strains. Root segments from wild-type or homozygous mtf1-4 (previously mtf2) mutant plants were inoculated with *A. tumefaciens* A348 or A281. The percentage of root segments that developed tumors was calculated. Error bars indicate s.e.m. from five replicates.

The transformation experiments described herein were carried out using *A. tumefaciens* A208 that contains a nopaline-type of Ti plasmid. Commonly used *Agrobacterium* strains were, for example A208, A348, A281 (Zhu et al., 2003; and Nam et al., 1999). To assess whether mtf1-4 (previously mtf2) shows increased susceptibility to other *A. tumefaciens* strains, root transformation assays were conducted using the octopine-type strain A348 and the succinamopine-type strain A281. The mtf1-4 (previously mtf2) mutant displayed 2-3-fold increased transformation susceptibility to these strains (FIG. 7). Thus, MTF plays an important role in plant susceptibility to different *Agrobacterium* strains.

Figure 1E:
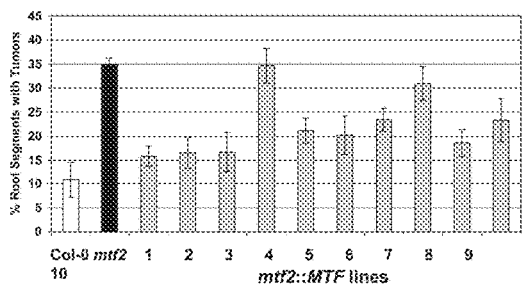
Figure 1F:
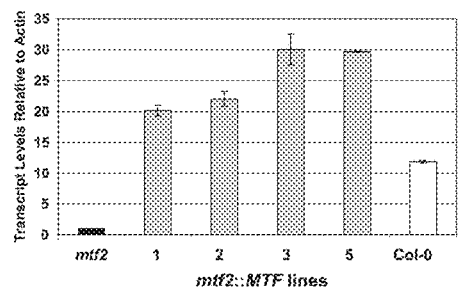

Further studies used homozygous mtf1-4 (previously mtf2) plants. Ectopic expression of the MTF cDNA in mtf1-4 (previously mtf2) resulted in several transgenic lines with restored levels of wild-type susceptibility to *Agrobacterium*-mediated transformation (FIG. 1E). These transgenic lines individually expressed various levels of MTF mRNA (FIG. 1F). Complementation experiments confirm that disruption of the MTF gene is responsible for increased transformation susceptibility.

The mtf1-4 (previously mtf2) mutant is hyper-susceptible to different strains of *A. tumefaciens* carrying nopaline-, octopine-, and succinomanopine-type Ti plasmids, indicating that MTF is a negative regulator of *Agrobacterium*-mediated transformation. Transformation recalcitrance of some *Arabidopsis* ecotypes results from decreased binding of *Agrobacterium* to roots. Other ecotypes are debilitated in T-DNA integration, a late stage of transformation (Nam et al., 1997). Reducing MTF expression in Bl-1, a highly recalcitrant ecotype, increased transformation susceptibility and bacterial attachment, highlighting the potential to increase transformation susceptibility of recalcitrant plant species by down-regulating expression of MTF orthologs.

The importance of phytohormones in increasing transformation prompted investigation of the role of cytokinins in transformation. *Agrobacterium* strains containing nopaline-type Ti plasmids secrete trans-zeatin, mediated by the vir region-localized gene TZS. *A. tumefaciens* tzs mutants are less virulent than are TZS$^+$ strains. The presence of TZS on the bacterial surface (Aly et al, 2008) may mean that metabolites from wounded plant cells may be converted into trans-zeatin at infection sites, resulting in down-regulation of MTF and consequent increased transformation susceptibility. Indeed, exogenous application of kinetin during infection increased the susceptibility of *Arabidopsis* roots infected with an *Agrobacterium* tzs mutant (Hwang et al., 2010). Down-regulation of MTF expression by cytokinins provides a molecular explanation for the importance of TZS to *Agrobacterium*-mediated transformation (Zhan et al, 1990). Although influential, cytokinin signaling is not essential for *Agrobacterium*-mediated transformation because many virulent *Agrobacterium* strains do not secrete cytokinins.

Regulation of gene expression by MTF is highly specific. Fewer than 40 genes are significantly up- or down-regulated ≥1.5-fold in the mtf mutants. One of the up-regulated genes, At1g50060 encoding a basic PR1-like protein, increased transformation susceptibility when over-expressed in *Arabidopsis*. Unlike its acidic counterpart, PR-1, At1g50060 is not salicylic acid (SA)-responsive, pathogen-induced, nor is its expression correlated with the establishment of systemic acquired resistance (Niki et al., 1998). However, At1g50060 transcripts are negatively regulated by a variety of biotic and abiotic stresses (Zimmerman et al., 2004). Thus, At1g50060 does not encode a defense-related protein. Increased transformation susceptibility of the wrky48 mutant suggests that *Agrobacterium* manipulates host defense responses to its advantage. Previously Veena et al. (2003) showed that infection of plant cells by transfer-competent *Agrobacterium* strains suppresses host defense gene expression 30-36 h after infection, although these genes are induced as early as 3-12 h after infection (Veena et al., 2003). MTF is a specific regulator of plant susceptibility to *Agrobacterium* as evidenced by lack of increased susceptibility to *A. brassicicola* and *P. syringae*. Increased resistance of the mtf mutant to *Botrytis* is likely due to downstream responses to decreased MTF expression.

In conclusion, MTF was identified as the first known regulator of plant susceptibility to *Agrobacterium*-mediated transformation. MTF regulates at least three genes independently capable of increasing transformation susceptibility. MTF also affects *Agrobacterium* binding to roots and integrates cytokinin secretion by *Agrobacterium* with transformation susceptibility. These findings pave the way for identifying orthologs of MTF in transformation-recalcitrant plant species and manipulating these genes to increase transformation efficiency of economically important crops.

EXAMPLES

Examples are provided for illustrative purposes and are not intended to limit the scope of the disclosure.

Figure 1G:
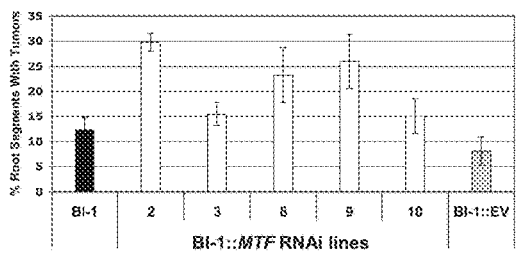
Figure 1H:
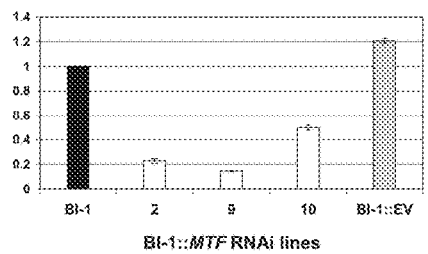
Figure 1H:
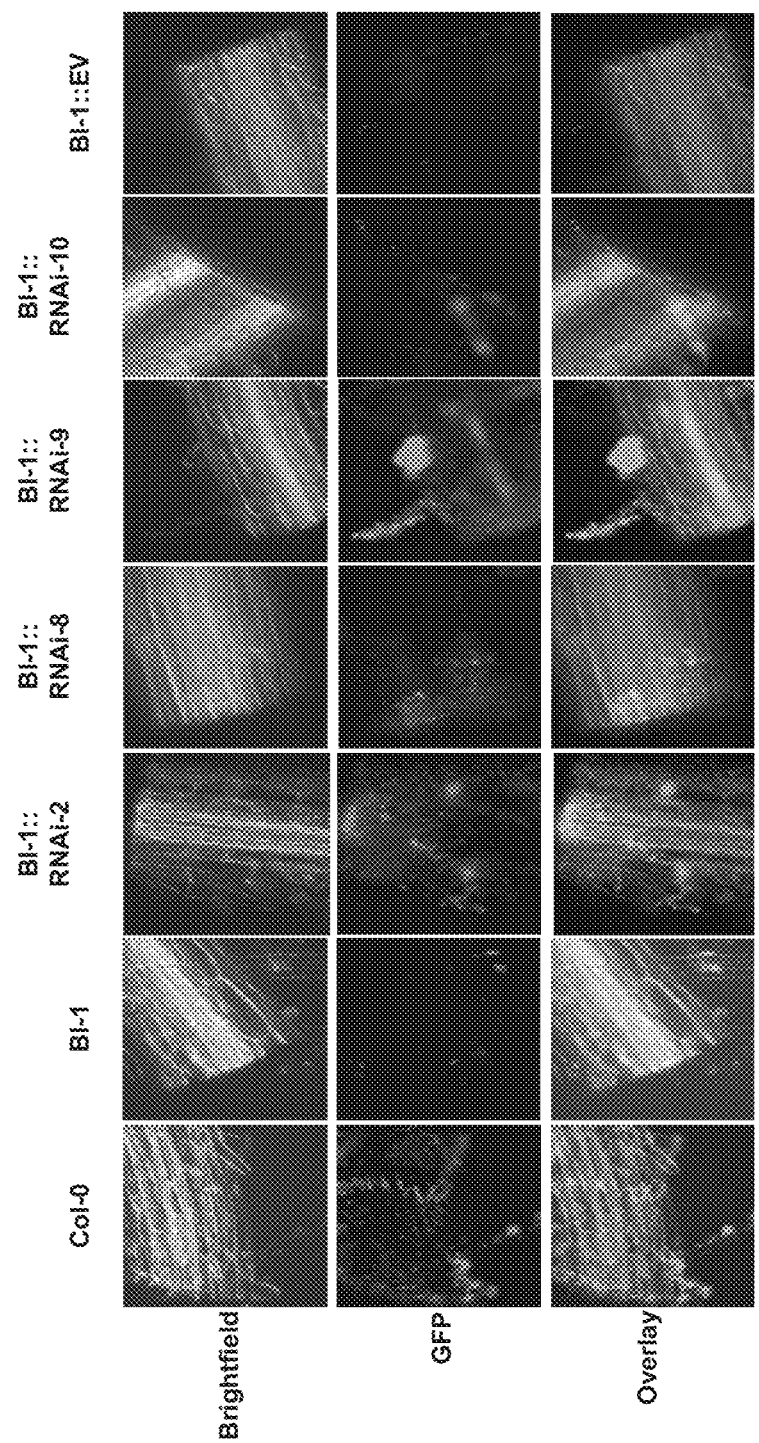
Figure 8:
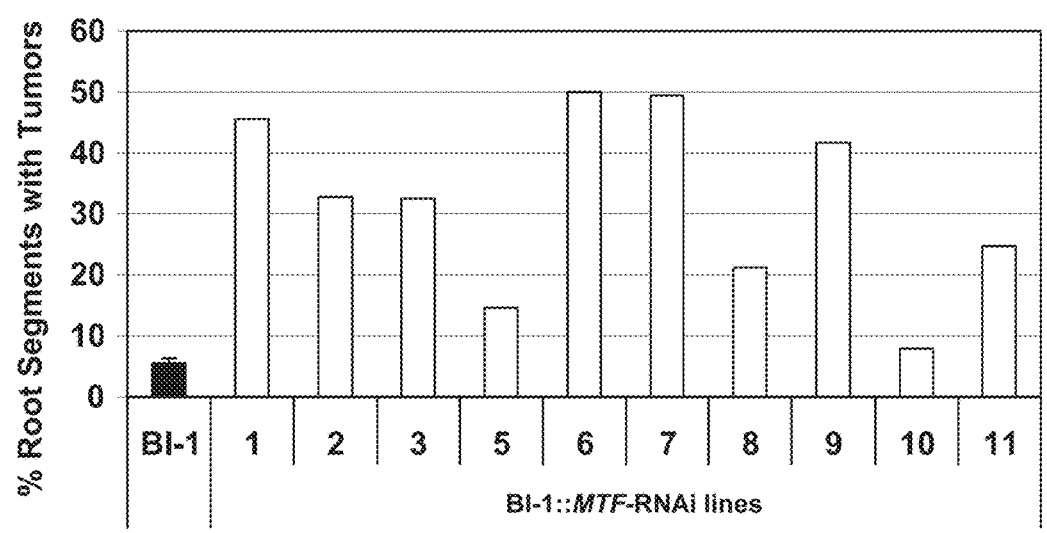
FIG. 8. Decreasing MTF expression increases transformation susceptibility of *Arabidopsis* ecotype Bl-1. Transgenic T1 generation *Arabidopsis* ecotype Bl-1 plants expressing a RNAi construction which targets MTF were inoculated with *A. tumefaciens* A208. The percentage of root segments that developed tumors was calculated. Numbers below the bars indicate individual Bl-1::MTF-RNAi lines. Error bar indicates s.e.m. from five replicates.

Example 1: Decreased MTF Expression in *Arabidopsis* Ecotypes Increases Transformation Susceptibility The hat3 and mtf1-4 (previously mtf2) mutants are in the Columbia background, an ecotype relatively amenable to root transformation. *Arabidopsis* ecotype Bl-1 is highly recalcitrant to root transformation (Nam et al., 1997), but can be transformed using a floral dip method (Mysore et al., 2000). MTF genes of ecotypes Columbia and Bl-1 are identical. An RNAi expression construction targeting MTF transcripts was introduced into ecotype Bl-1 and the derived transgenic lines were screened for root transformation susceptibility. Eight of the 10 tested T1 generation transgenic plants exhibited increased susceptibility (FIG. 8). 25 T2 generation plants from each of five MTF-RNAi lines were tested, along with a RNAi empty vector line. Three of these transgenic lines continued to show higher transformation susceptibility (FIG. 1G). RNAi lines 2 and 9, that had increased transformation susceptibility, showed 4.6- and 7-fold decreases in MTF transcripts, respectively, whereas line 10, that did not have altered susceptibility, showed only a 2-fold decrease in MTF transcript levels (FIG. 1H). A transgenic line containing an empty RNAi vector did not display altered transformation susceptibility or altered MTF transcript levels. These results indicate that transformation susceptibility of Bl-1 plants is dependent on the level of MTF transcripts.

Earlier studies indicated that roots of ecotype Bl-1 do not bind Agrobacteria well. *A. tumefaciens* expressing GFP showed increased bacterial attachment in the high-transforming transgenic Bl-1 RNAi lines 2 and 9 compared to that of the low-transforming line 10, the empty RNAi vector line, and wild-type Bl-1 (FIG. 1I), suggesting that decreased MTF transcripts in Bl-1 increase susceptibility during the early attachment stage of the transformation process.

Example 2: Phytohormone Treatment Increases Transformation Susceptibility

Chateau et al. (2000) reported that phytohormone preincubation of *Arabidopsis* petioles increases transformation susceptibility, and hormone pre-treatment is part of the protocol to generate transgenic *Arabidopsis* plants from roots (Valvekens et al., 1988). Because phytohormone pre-treatment of *Arabidopsis* root segments may enhance transformation susceptibility, which may be important in light of the fact that nopaline-type *Agrobacterium* strains express a trans-zeatin secretion (TZS) gene, and thus secrete cytokinins into the medium.

Root segments from five transformation-recalcitrant *Arabidopsis* ecotypes (Bl-1, Bla-2, Cal-0, Dijon-G, and Petergof) and a transformation-susceptible ecotype (Ws-2) were incubated on callus inducing medium (CIM) containing phytohormones prior to infection by *Agrobacterium* and scored for transformation susceptibility. All ecotypes displayed increased transformation susceptibility after one day of phytohormone pre-treatment (FIG. 2A, 2B). There was a further increase in transformation frequency after three days of phytohormone pre-treatment.

Whether phytohormone pre-treatment of *Arabidopsis* roots enhances the frequency of transient transformation was investigated, a process that does not require T-DNA integration into the plant genome. β-glucuronidase (GUS) activity, resulting from the transfer of a gusA-intron gene from *Agrobacterium* to plants, is a standard assay for transient transformation (Narasimhulu et al., 1996). Hormone pretreatment of roots also increased transient transformation (FIG. 2C). Petiole explants of *Arabidopsis* treated with phytohormones before *Agrobacterium* infection showed actively dividing and dedifferentiated cells, and increased transformation efficiency. Increased DNA duplication and cell division of phytohormone treated *Petunia hybrida* cells correlated with increased *Agrobacterium*-mediated transformation (Villemont et al., 1997). Thus, phytohormone treatment sensitizes roots to *Agrobacterium*-mediated transformation at an early step (prior to T-DNA integration) of the transformation process.

Example 3: MTF Expression is Repressed by Cytokinins from *Agrobacterium*

Ti-plasmids of some nopaline-type *Agrobacterium* strains carry a TZS gene that directs synthesis and secretion of cytokinins (Regier et al., 1982; Beaty et al., 1986; and Powell et al., 1988). TZS promotes transformation both by nopaline-type *A. tumefaciens* strains and, when transferred to strain 1855, *A. rhizogenes* strains. *A. tumefaciens* strains harboring nopaline-type Ti plasmids secrete trans-zeatin or trans-zeatin ribosides into the medium in amounts >1 µg/L (Claeys et al., 1978; McCloskey et al, 1980).

Figure 3A:
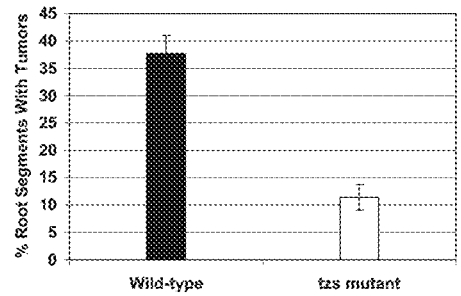
FIGS. 3A-3D. *A. tumefaciens* tzs mutant is less virulent than the wild-type strain. 3A Percentage of root segments developing tumors after inoculation with tzs mutant and wild-type *A. tumefaciens*. 3B Relative MTF transcript levels in roots infected with tzs mutant and wild-type *A. tumefaciens*. 3C MTF promoter-EYFP construction expresses constitutively in transgenic *Arabidopsis*. 3D Inoculation of MTF promoter-EYFP transgenic roots with TZS$^+$ and tzs mutant *A. tumefaciens*.
Figure 3B:
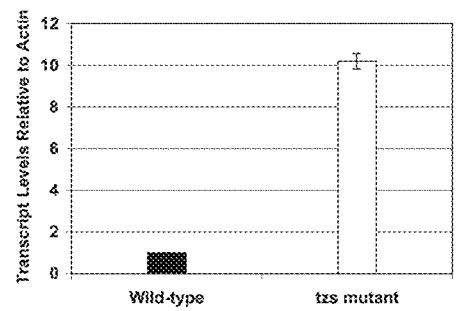

Tumorigenesis assays were conducted on *Arabidopsis* roots infected with the TZS$^+$ strain *A. tumefaciens* NT1RE (pJK270) and the tzs frameshift mutant NT1RE(pJK270tzs-fs). *Arabidopsis* root segments infected with the tzs mutant developed fewer tumors than did roots infected with the wild-type strain (FIG. 3A). Root segments infected with wild-type bacteria had 10-fold fewer MTF transcripts than did roots infected with tzs-mutant bacteria (FIG. 3B). These results indicate that MTF is down-regulated by trans-zeatin produced by *A. tumefaciens*, leading to altered transformation susceptibility.

Example 4: TZS-Expressing Agrobacteria Repress Expression of MTF

Figure 3C:
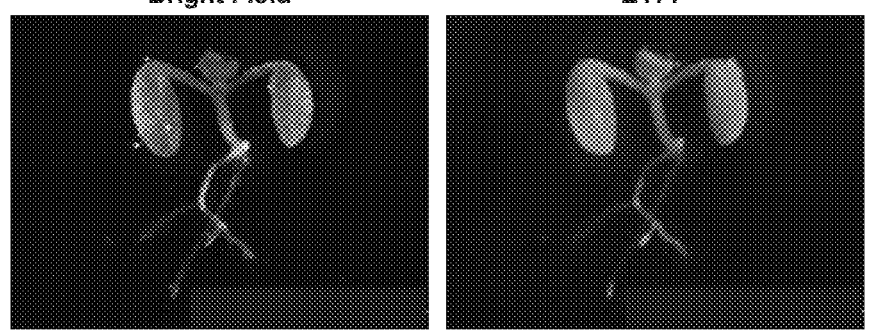
Figure 3D:
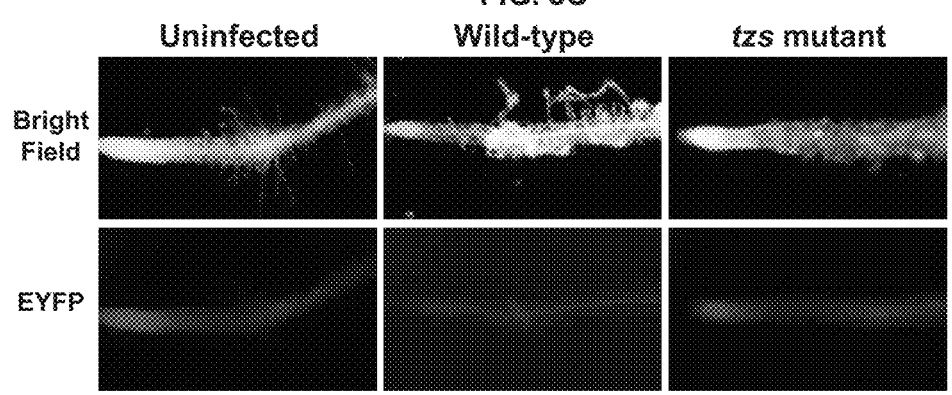

Decreased MTF transcript levels in roots co-cultivated with TZS$^+$ *A. tumefaciens* suggests an early involvement of trans-zeatin and MTF in transformation. To determine in which root tissues this decrease in MTF expression was most pronounced, transgenic *Arabidopsis* lines expressing EYFP under control of the MTF promoter were generated. MTF promoter activity was constitutive in all examined plant tissues (FIG. 3C). The highly-expressing line Col7-$P_{MTF}$-EYFP4 was used to assess whether root tissues exhibited altered MTF expression when infected with a TZS$^+$ *A. tumefaciens* strain. Fluorescence decreased in roots by 48 h of co-cultivation, most noticeably in the epidermal and cortical cells of the elongation zone, the region most susceptible to transformation (FIG. 3D). This decrease in fluorescence was not observed in roots incubated with the tzs frameshift mutant. These results are consistent with the decreased MTF transcript levels observed in roots co-cultivated with TZS$^+$ bacteria.

Figure 29:
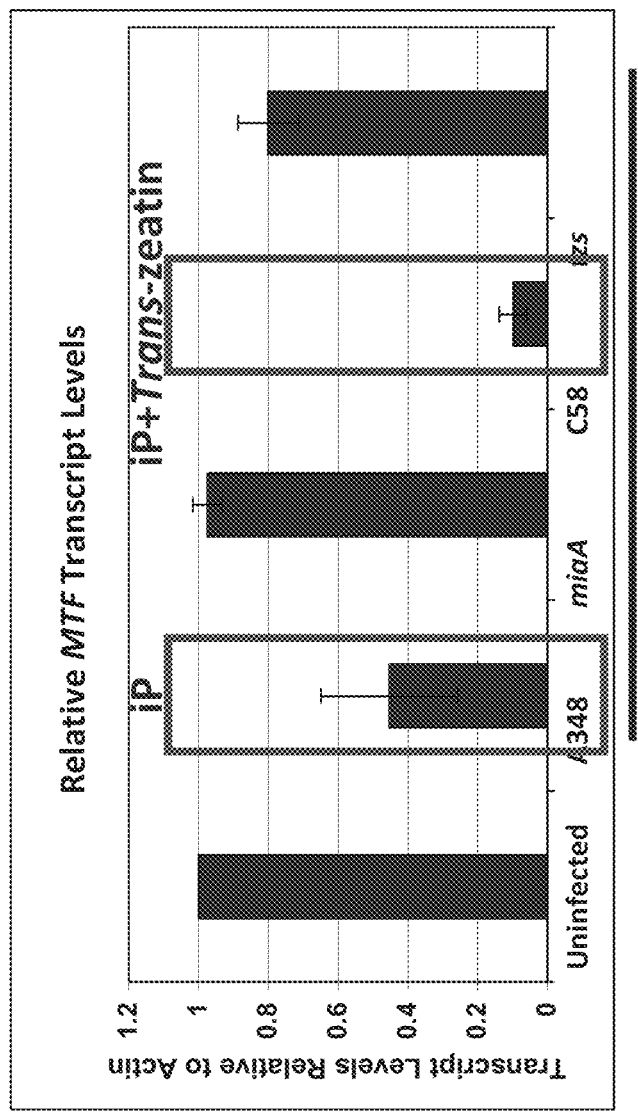
FIG. 29. *Arabidopsis* plants infected with TZS and/or iP-producing *A. tumefaciens* strains show lower amounts of MTF transcripts.

Example 5: MiaA-Expressing Agrobacteria Repress Expression of MTF and are More Susceptible to Transformation MiaA encodes an tRNA-isopentenyltransferase that isopentenylates adenine residues in tRNAs. Breakdown of tRNAs can release isopentenyladenine, a cytokinin. When *Arabidopsis* root segments are inoculated with Agrobacteria that contain a wild-type MIAA gene, the accumulation of MTF transcripts is repressed (FIG. 29). miaA mutant bacteria are less virulent than are wild-type bacteria (FIG. 30).

Figure 4A:
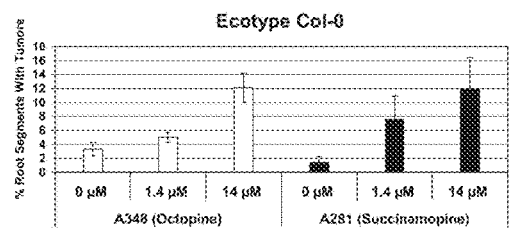
FIGS. 4A-4E. Trans-zeatin treatment increases susceptibility to *Agrobacterium*-mediated transformation by strains lacking TZS. 4A-4B Percentage of root segments developing tumors in Col-0 4A and Bl-1 4B inoculated with *A. tumefaciens* A348 and A281 in the absence or presence of trans-zeatin. Relative MTF transcript levels in root segments of Col-0 4C and Bl-1 4D treated for two days with trans-zeatin. 4E Attachment of GFP-tagged *A. tumefaciens* A281 to root segments of Col-0 and Bl-1 treated for 24 h with 0 or 1.4 µM trans-zeatin.
Figure 4B:
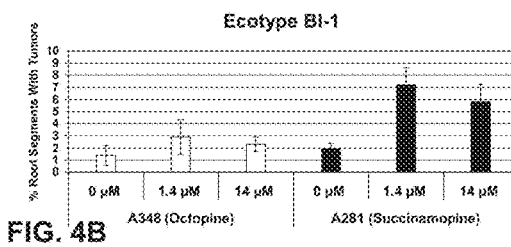
Figure 4C:
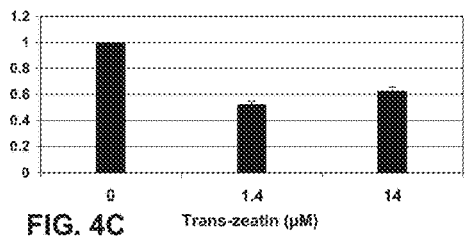
Figure 4D:
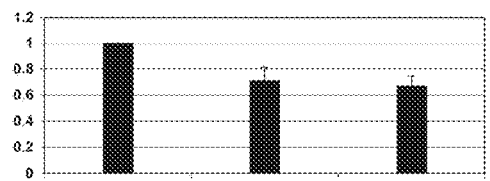
Figure 4E:
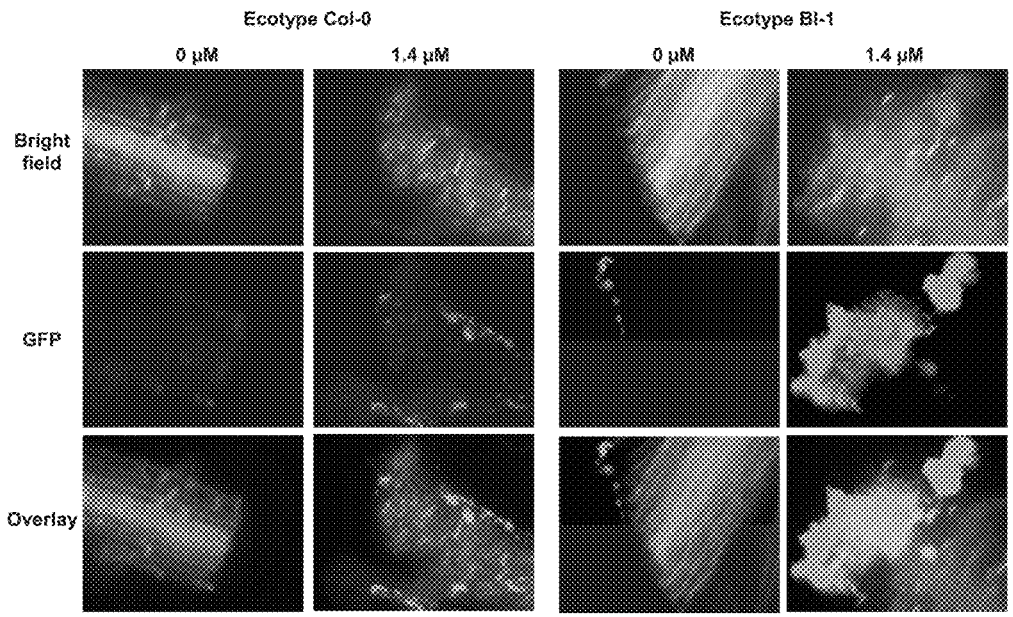

Example 6: Cytokinin Enhances Attachment of TZS-Lacking *A. tumefaciens* Strains To determine whether exogenous application of trans-zeatin to roots could influence transformation susceptibility, *Arabidopsis* roots were incubated on medium containing trans-zeatin and they were infected with *A. tumefaciens* A348 or A281. Neither of these strains harbors TZS. Trans-zeatin concentrations representing the range secreted by nopaline-type *A. tumefaciens* strains were used. Trans-zeatin treatment of Col-0 roots resulted in a 4-8-fold increase in transformation efficiency by these *A. tumefaciens* strains. Ecotype Bl-1 roots infected with these strains showed a 2-3-fold increase in susceptibility (FIG. 4A, 4B). Incubation of roots on trans-zeatin decreased MTF transcript levels by 30-60% and also increased attachment of *A. tumefaciens* A281 (FIG. 4C, 4D, 4E).

Figure 5B:
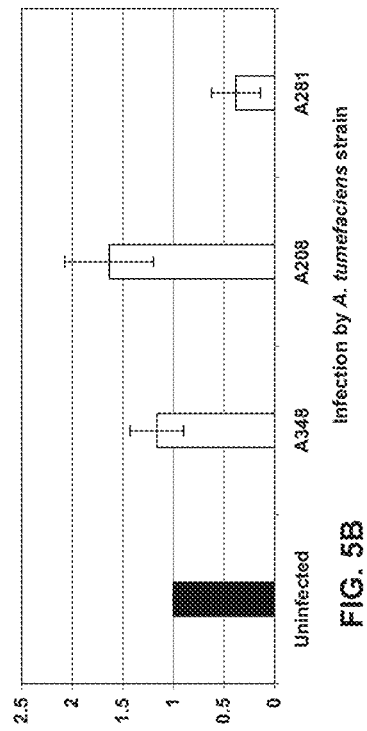
FIGS. 5A-5D. Manipulation of *Arabidopsis* genes that are regulated by MTF increases susceptibility to *Agrobacterium*-mediated transformation. 5A Percentage of root segments developing tumors in transgenic plants over-expressing At1g50060 or At5g15725 cDNAs inoculated with *A. tumefaciens* A208. Numbers indicate individual T2 generation lines. Relative transcript levels of At1g50060 5B and At5g15725 5C after inoculation with *A. tumefaciens* A208 (TZS$^+$), A348 (TZS$^-$), or A281 (TZS$^-$). 5D Percentage of root segments developing tumors in T-DNA-disruption mutants of genes down-regulated in mtf plants.
Figure 5D:
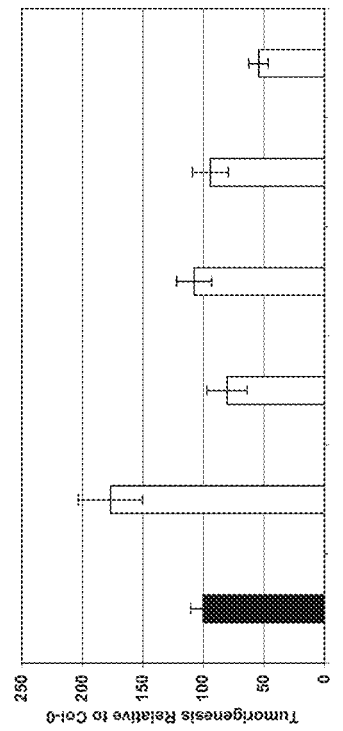
Figure 5A:
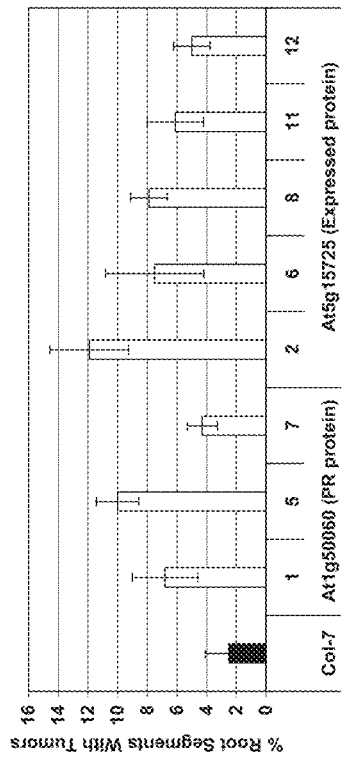
Figure 9:
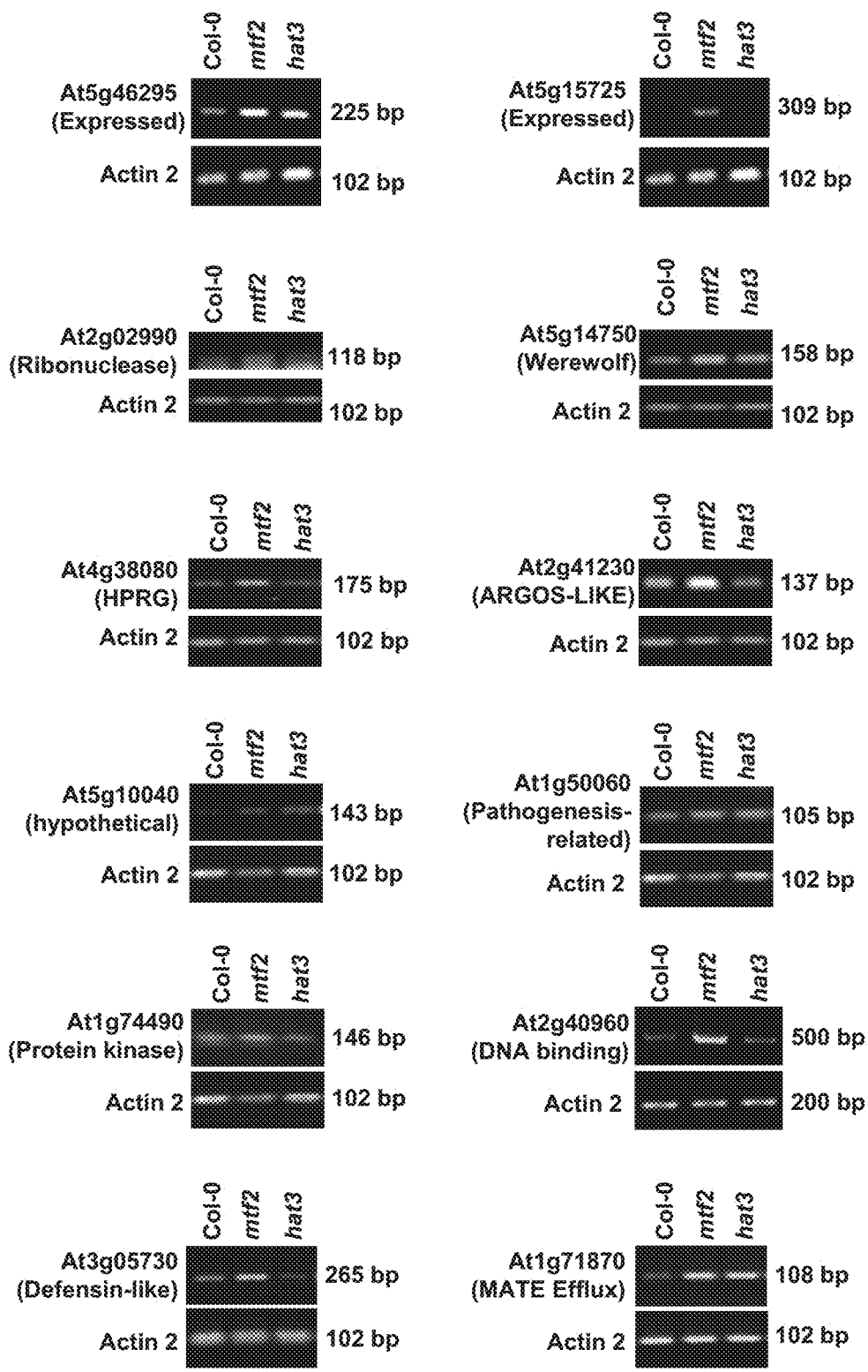
FIG. 9. RT-PCR analysis of transcripts of genes up-regulated in hat3 and homozygous mtf1-4 (previously mtf2) roots. Amplified fragments were fractionated by electrophoresis through agarose gels, stained with ethidium bromide, and photographed. The ACT2 gene was used as a normalization control.
Figure 10:
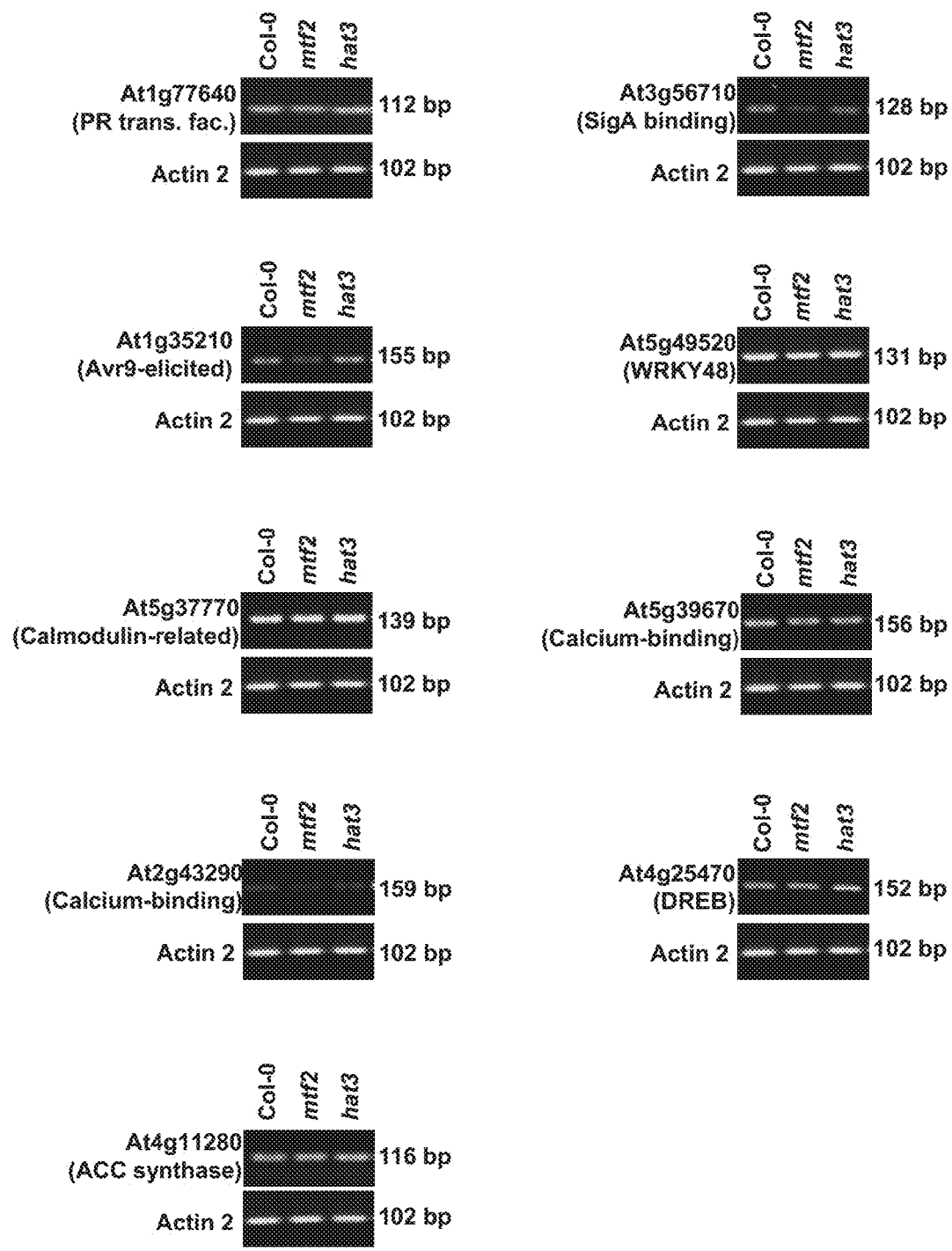
FIG. 10. RT-PCR analysis of transcripts of genes down-regulated in hat3 and homozygous mtf1-4 (previously mtf2) roots. Amplified fragments were fractionated by electrophoresis through agarose gels, stained with ethidium bromide, and photographed. The ACT2 gene was used as a normalization control.
Figure 11:
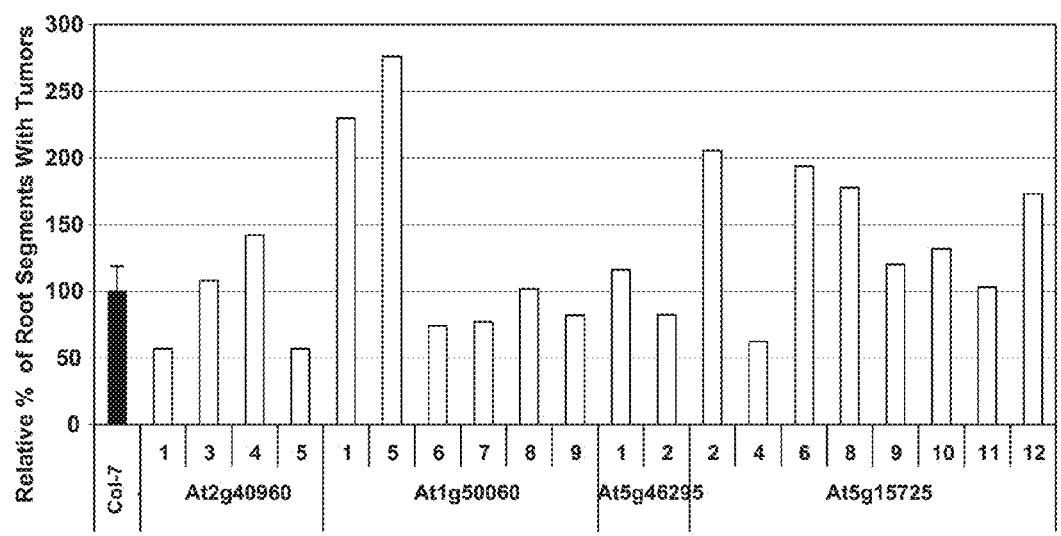
FIG. 11. Over-expression of several *Arabidopsis* genes that are regulated by MTF increases plant susceptibility to *Agrobacterium*-mediated transformation. Root segments from T1 generation transgenic plants over-expressing At2g40960, At1g50060, At5g46295, or At5g15725 cDNAs were inoculated with *A. tumefaciens* A208. The percentage of root segments that developed tumors was calculated. Numbers indicate individual transgenic lines. Error bar indicates s.e.m. from five replicates.

Example 7: Decreased MTF Expression Alters Expression of Genes Important for *Agrobacterium*-Mediated Transformation The *Arabidopsis* ATH1 Genome Arrays were used to identify genes whose expression is altered in wild-type, heterozygous hat3, and homozygous mtf1-4 (previously mtf2) *Arabidopsis* roots. A total of 39 genes exhibited statistically significant differential expression between both mtf mutants and the wild-type, and had a difference greater than 1.5-fold (Table 1). Of these, 23 genes were commonly up-regulated and 16 genes were commonly down-regulated in both mtf mutants compared to the wild-type. These results were validated using RT-PCR (FIGS. 9 and 10). cDNAs of four genes At2g40960, At1g50060, At5g46295, At5g15725 that were up-regulated in both mtf mutants were overexpressed. Transgenic T1 lines over-expressing At2g40960 and At5g46295 did not exhibit a hat phenotype (FIG. 11). However, several T1 lines over-expressing At1g50060 and At5g15725 showed increased transformation susceptibility that carried over to the T2 generation (FIG. 5A). At1g50060 is a putative pathogenesis-related 1 (PR-1)-like protein proposed to be a serine protease involved in various signaling processes (Fernandez et al, 1997; Milne et al., 2003). At1g50060 transcript levels in root segments infected with *A. tumefaciens* A208 (TZS$^+$) and strains A348 and A281 were assessed (TZS$^-$) and observed increased transcript levels only in A208-infected roots (FIG. 5B). Presumably, cytokinins produced by *A. tumefaciens* A208 regulate expression of MTF in the roots, which in turn regulate expression of At1g50060.

Figure 5C:
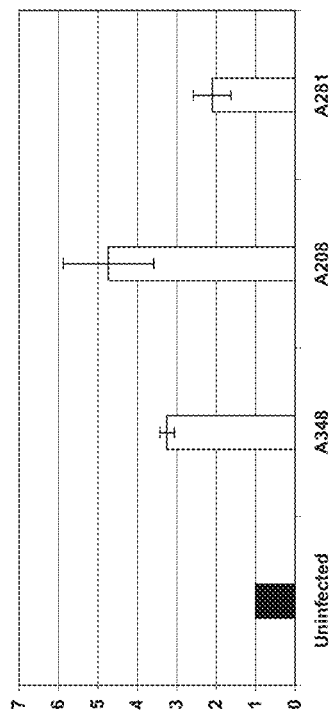

At5g15725 is annotated as an unknown protein (Tair; http://www.*arabidopsis*.org/). *Arabidopsis* root segments were infected with *A. tumefaciens* strains A348, A208, or A281. Expression of At5g15725 was up-regulated by all three strains; however, the highest transcript levels were found after infection by the TZS-producing strain A208 (FIG. 5C) which may be related to trans-zeatin production.

To assess the effect of genes down-regulated by MTF, roots of independent T-DNA insertion mutants in At5g49520 (wrky48), At3g56710 (sigA), At4g25470 (dreb1c), At5g39670 (cbp1) and At2g43290 (mss3) were assayed. The wrky48 mutant exhibited a mild hat phenotype (FIG. 5D).

None of the other tested mutants displayed increased transformation susceptibility. WRKY48 is a transcriptional activator that represses plant basal defenses (Xing et al., 2008). Results indicate that defense genes regulated by WRKY48 do not play a major role in protecting the host from *Agrobacterium* infection, or that *Agrobacterium* somehow targets and/or recruits host defenses to its advantage.

Example 8: Effect of the MTF Mutation on Infection by Other Phytopathogens

Figure 6A:
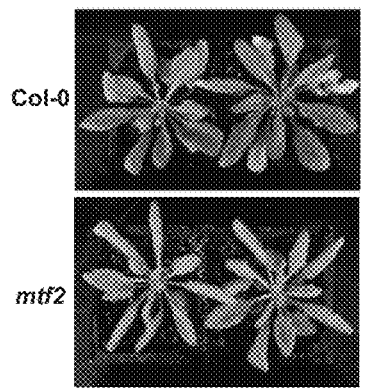
FIGS. 6A-6D. *Arabidopsis* mtf mutants are resistant to *Botrytis cinerea*. Col-0 and mtf1-4 (previously mtf2) plants were spray 6A or drop-inoculated 6B with *B. cinerea* spores. Average lesion diameter 6C was calculated from drop-inoculated leaves 4 days post-inoculation. 6D Relative ORA59 transcript levels in Col-0 and mtf1-4 (previously mtf2) leaves 0, 24, and 48 h post-inoculation.
Figure 6B:
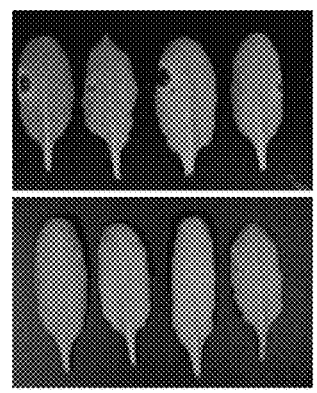
Figure 6C:
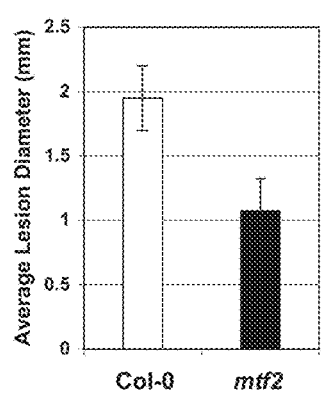
Figure 6D:
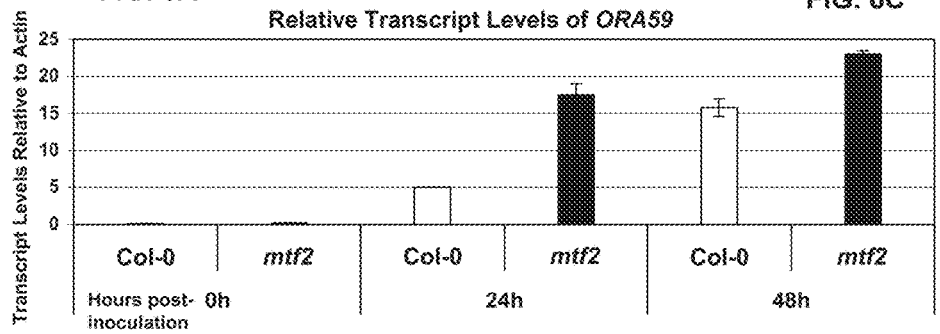
Figure 12A:
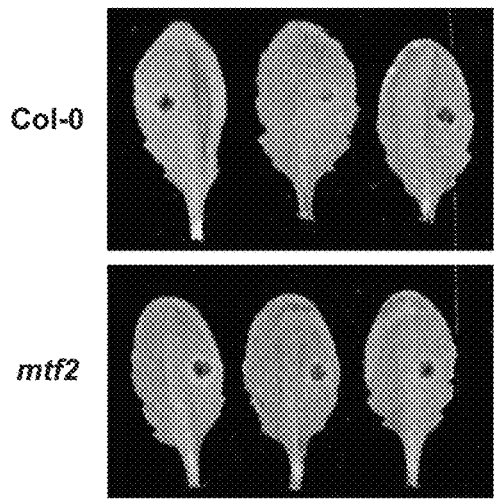
FIGS. 12A-12B. Homozygous mtf1-4 (previously mtf-2) plants show no alteration in susceptibility to *Alternaia brassicicola* or *Pseudomonas syringae* DC3000. 12A Leaves of wild-type and homozygous mtf1-4 (previously mtf2) mutant plants were inoculated with 5 µL of a 500,000 spores/mL *A. brassicicola* spore suspension. The leaves were photographed 5 d after inoculation. 12B Leaves of wild-type and homozygous mtf1-4 (previously mtf2) mutant plants were inoculated with wild-type and hrcC mutant *Pseudomonas syringae* pv. tomato. After 0 and 3 d, leaf sections were ground and the bacteria plated.
Figure 12B:
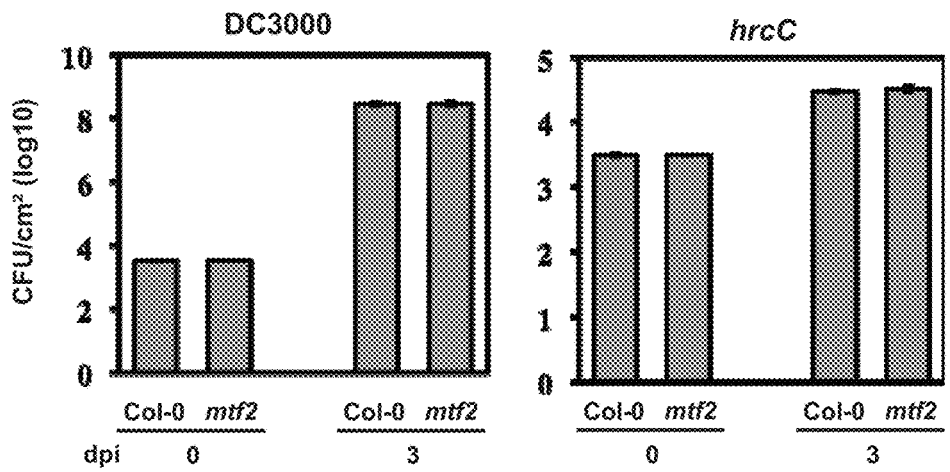
Figure 13:
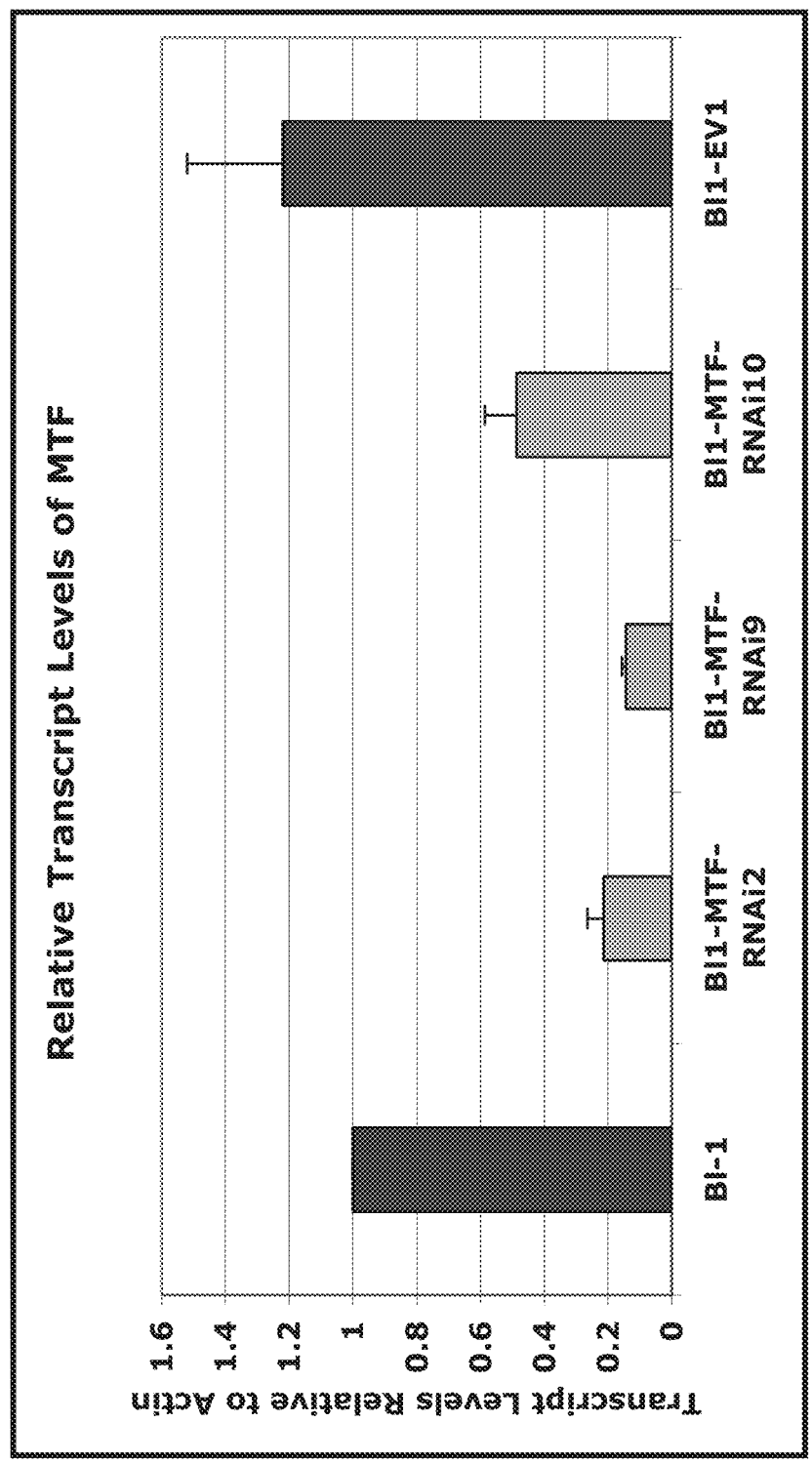
FIG. 13. MTF-RNAi lines in *Arabidopsis* ecotype Bl-1 show varying levels of MTF transcripts.
Figure 14:
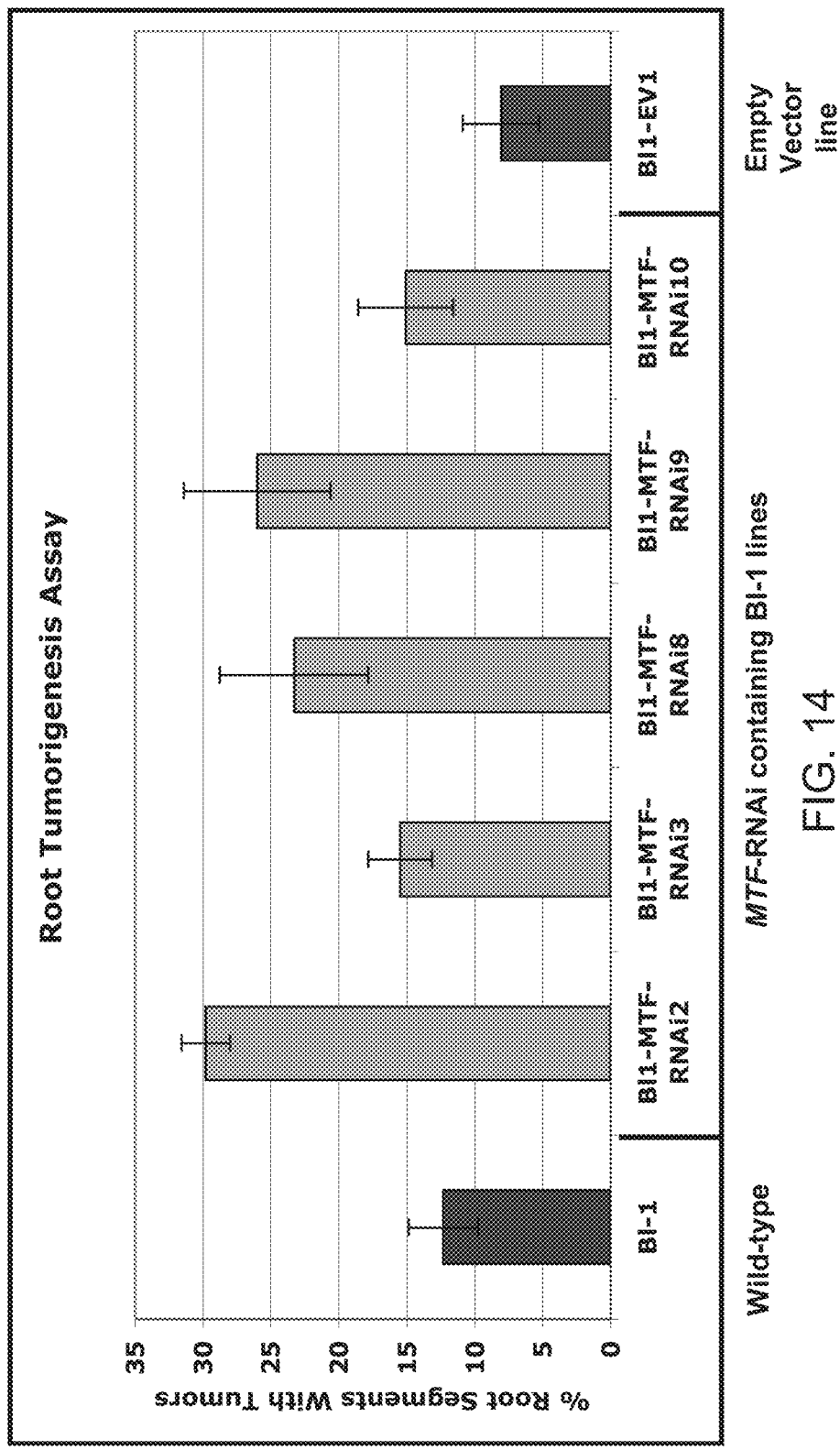
FIG. 14. Decreasing MTF transcripts in the transformation-recalcitrant *Arabidopsis* ecotype Bl-1 increases susceptibility to *Agrobacterium*. Bacterial concentration ($10^8$ cfu/mL).
Figure 15:
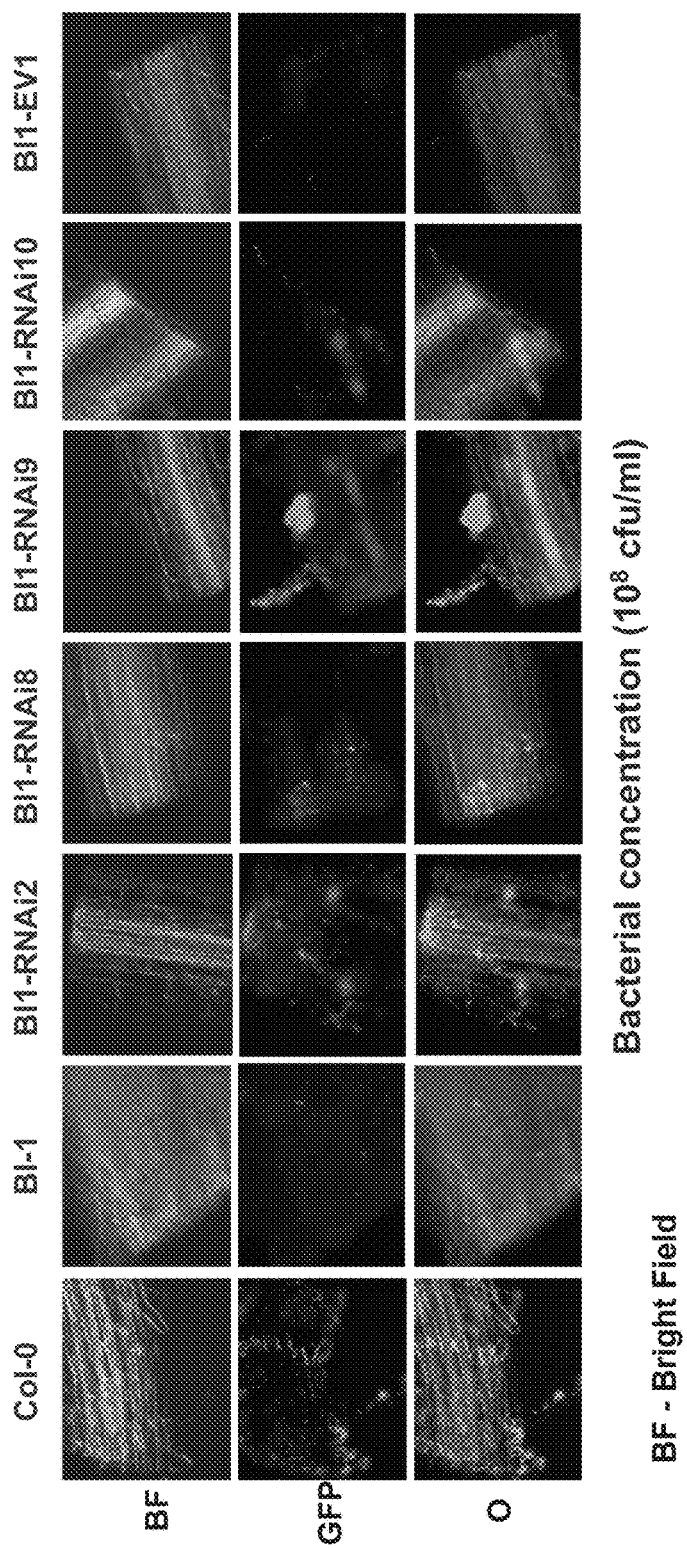
FIG. 15. MTF-RNAi lines show increased attachment of GFP-labeled Agrobacteria.
Figure 17:
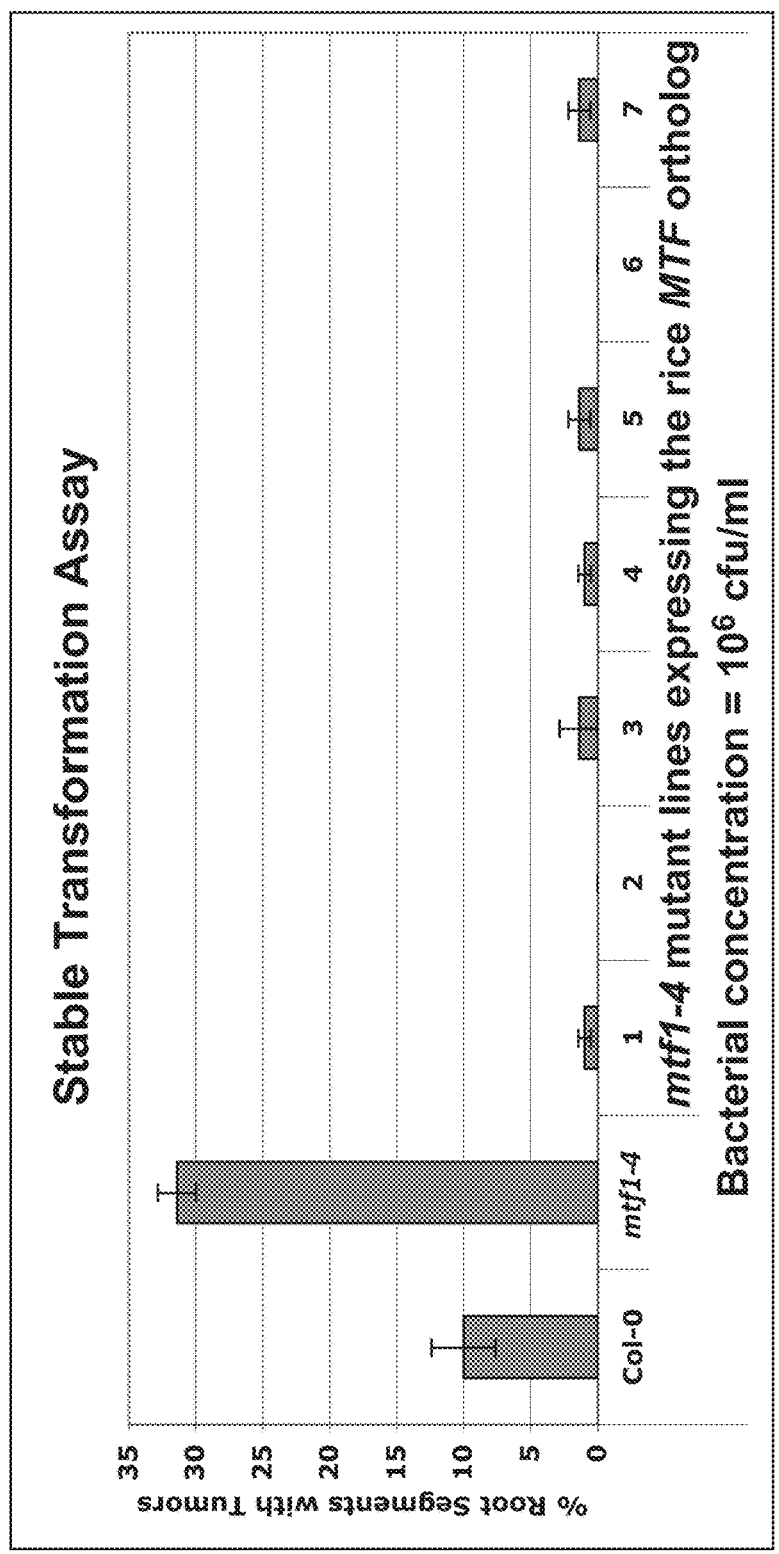
FIG. 17. Expression of the rice MTF ortholog in the *Arabidopsis* mtf1-4 (previously mtf2) mutant results in lower transformation susceptibility.
Figure 18:
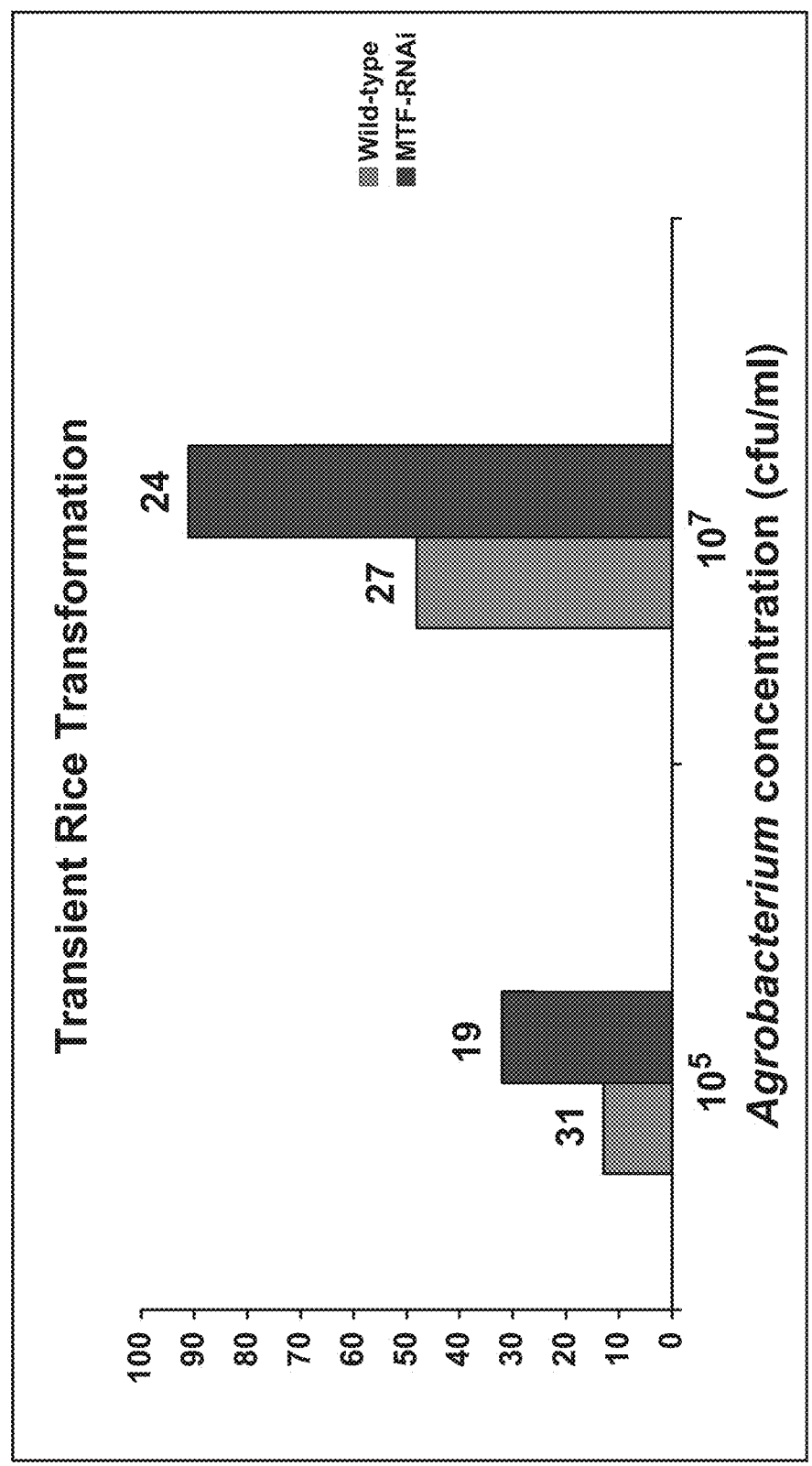
FIG. 18. A rice MTF-RNAi line shows increased transient transformation.
Figures 19A, 19B:
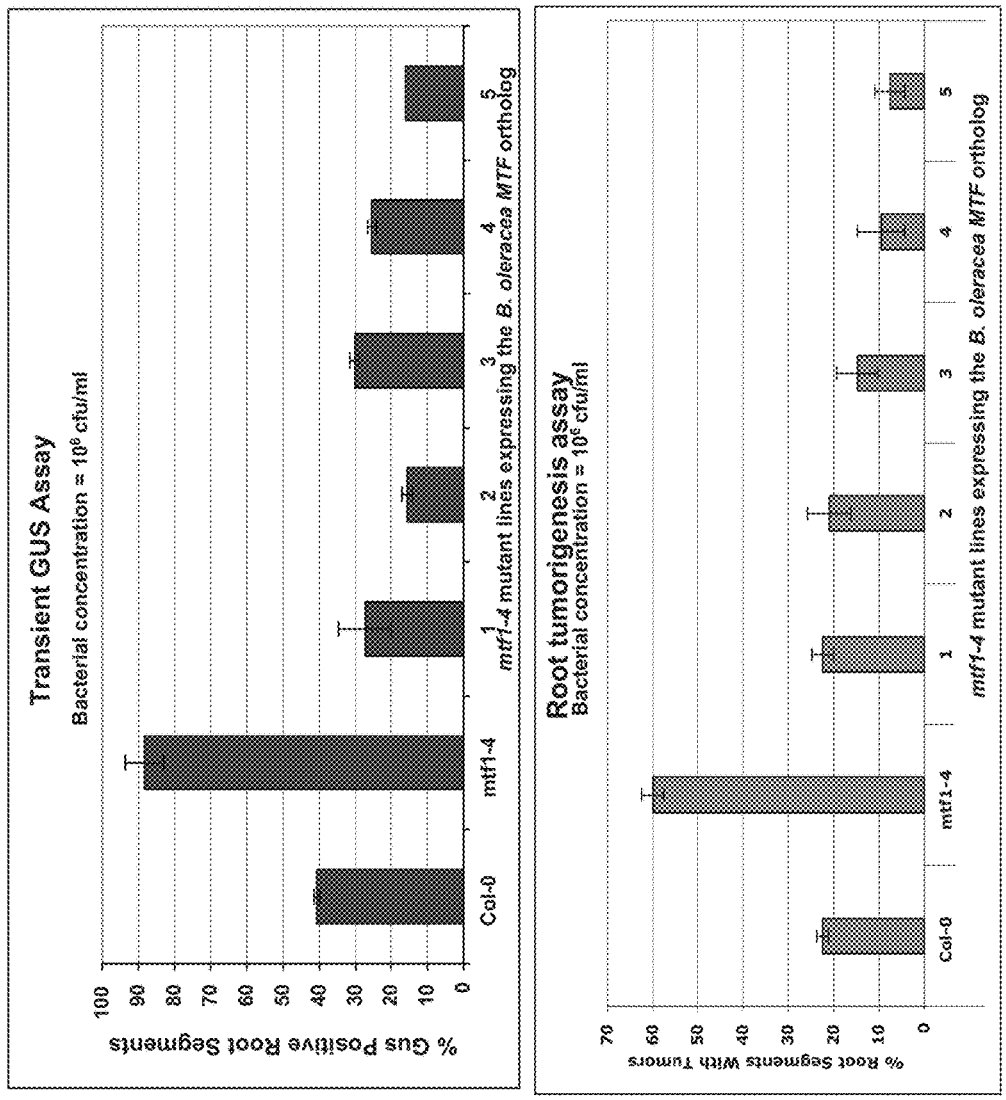
FIGS. 19A-19B. Expression of the *Brassica oleracea* MTF ortholog in the *Arabidopsis* mtf1-4 (previously mtf2) mutant results in lower transformation susceptibility. 19A shows results of a transient GUS assay; 19B a root tumorigenesis assay.
Figures 20A, 20B:
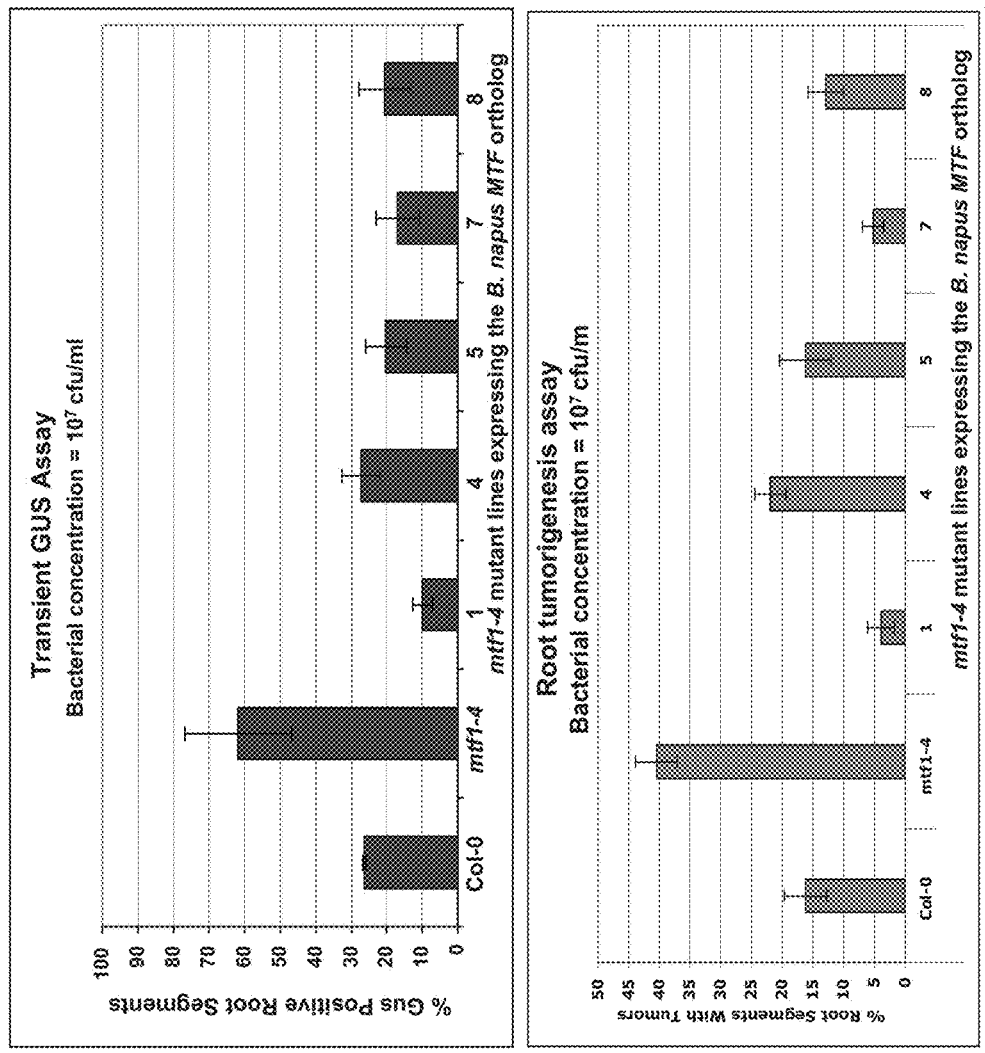
FIGS. 20A-20B. Expression of the *Brassica napus* MTF ortholog in the *Arabidopsis* mtf1-4 (previously mtf2) mutant results in lower transformation susceptibility. 20A shows results of a transient GUS assay; 20B a root tumorigenesis assay.
Figure 21:
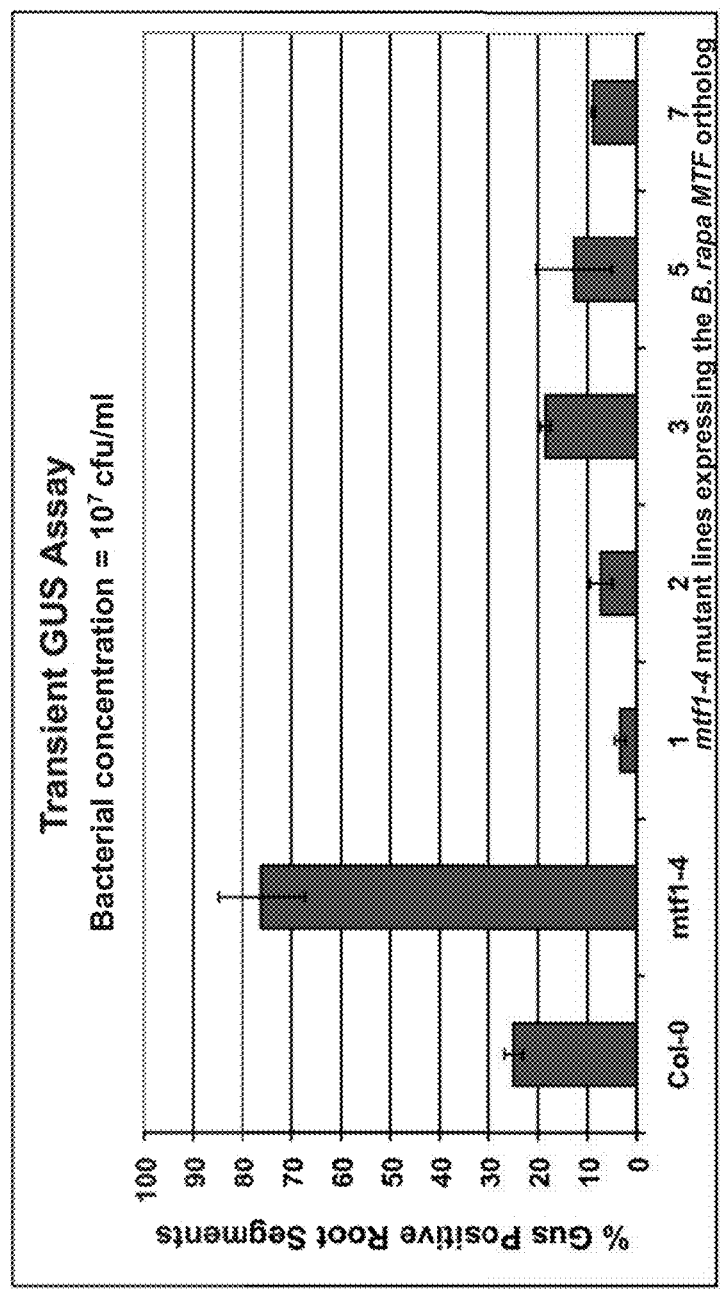
FIG. 21. Expression of the *Brassica rapa* MTF ortholog in the *Arabidopsis* mtf1-4 (previously mtf2) mutant results in lower transformation susceptibility. (Transient GUS assay).
Figure 23:
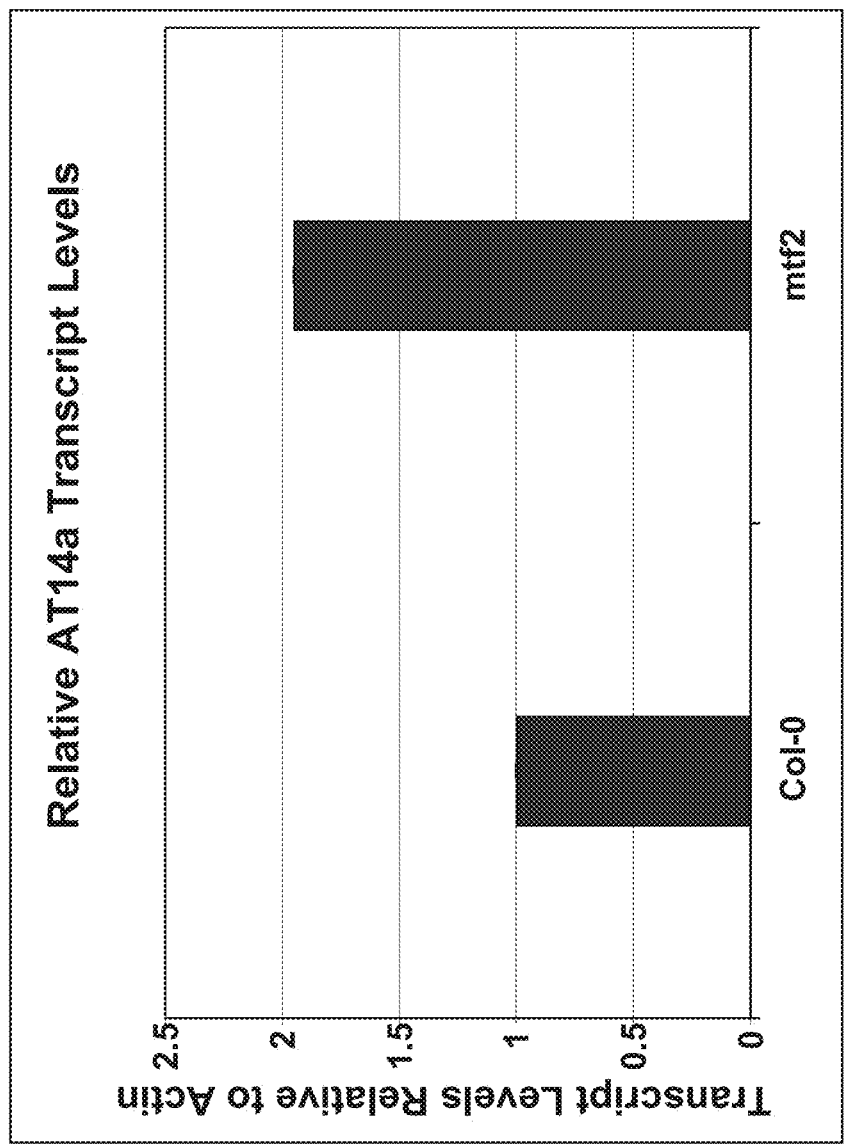
FIG. 23. At14a: The mtf1-4 (previously mtf2) mutant shows increased At14a transcript levels; At14a was of interest because its expression is up-regulated in the *Arabidopsis* mtf myb transcription factor mutant; this mutant is hyper-susceptible to *Agrobacterium*-mediated transformation.
Figure 24:
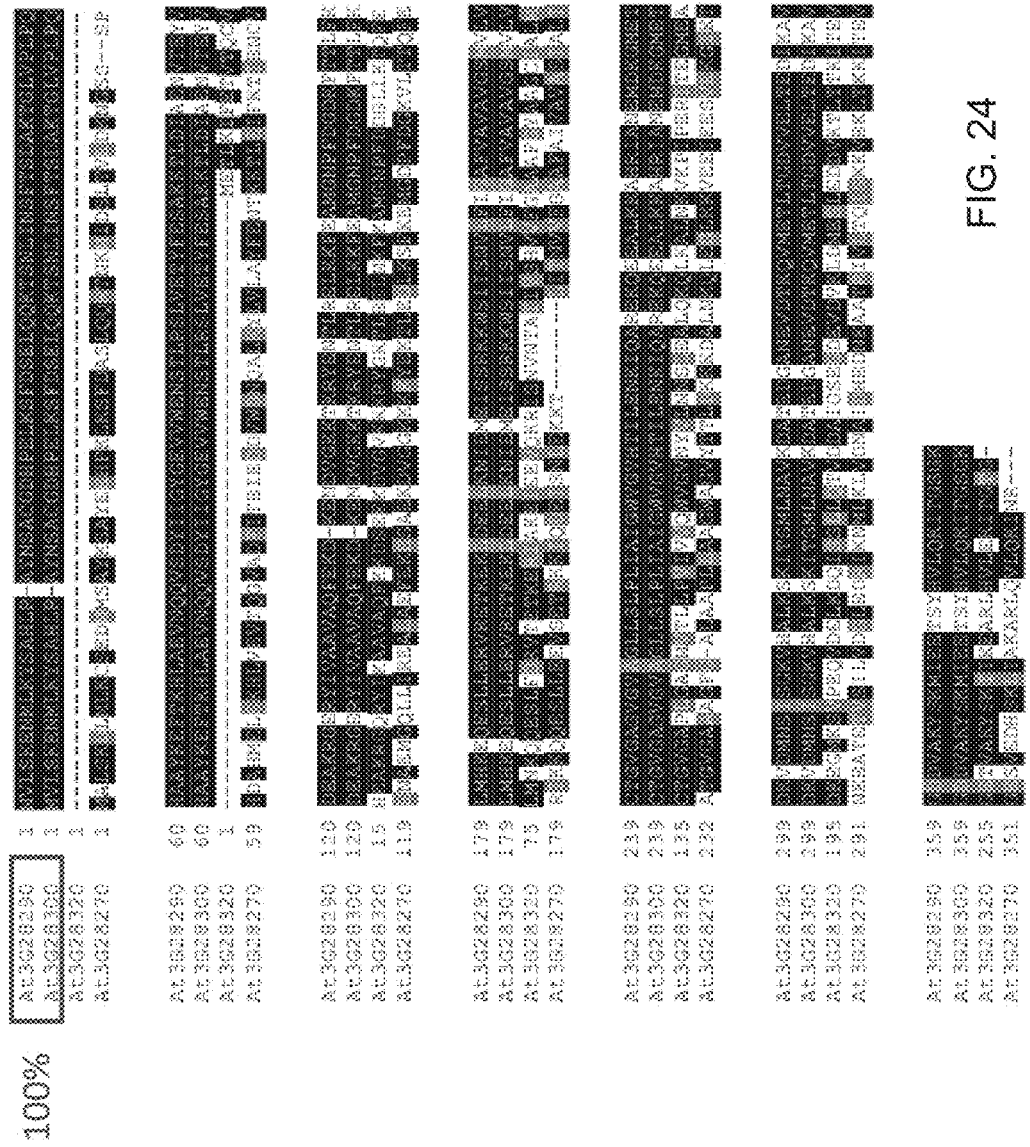
FIG. 24. At14a Sequences: The *Arabidopsis* data bases indicate that there are two identical At14a gene sequences ("At3G28290" and "At3G28300" both disclosed as SEQ ID NO: 81), plus two related sequences (SEQ ID NOS 82-83, respectively, in order of appearance).
Figure 25A:
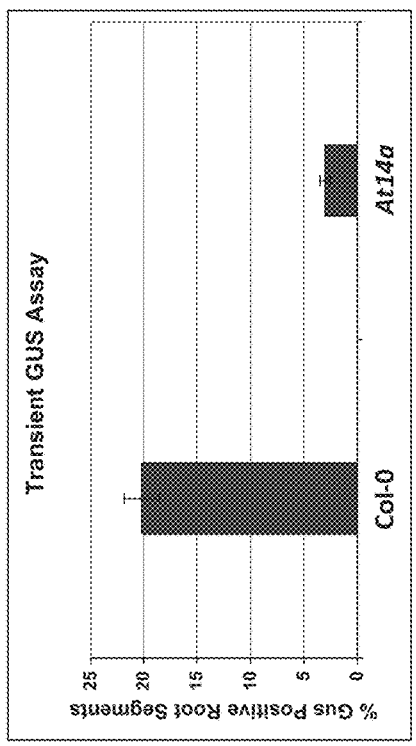
FIGS. 25A-25B. At14a Transformation: The transformation susceptibility of the *Arabidopsis* At14a mutant is lower than that of wild-type Col-0 plants. 25A shows a transient GUS assay; 25B antibiotic resistant calli.
Figure 25B:
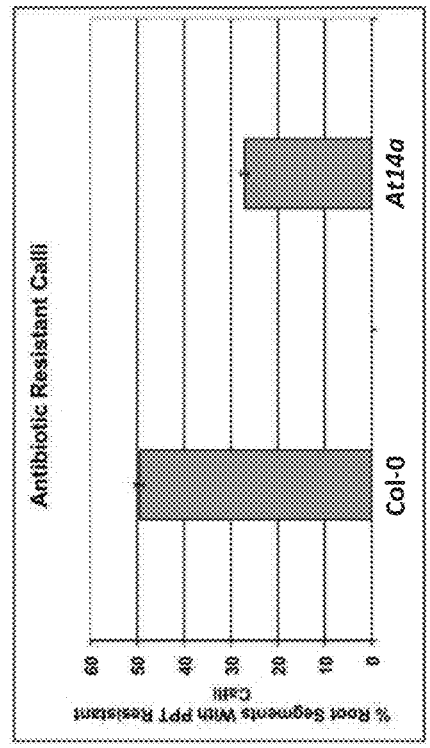
Figure 26:
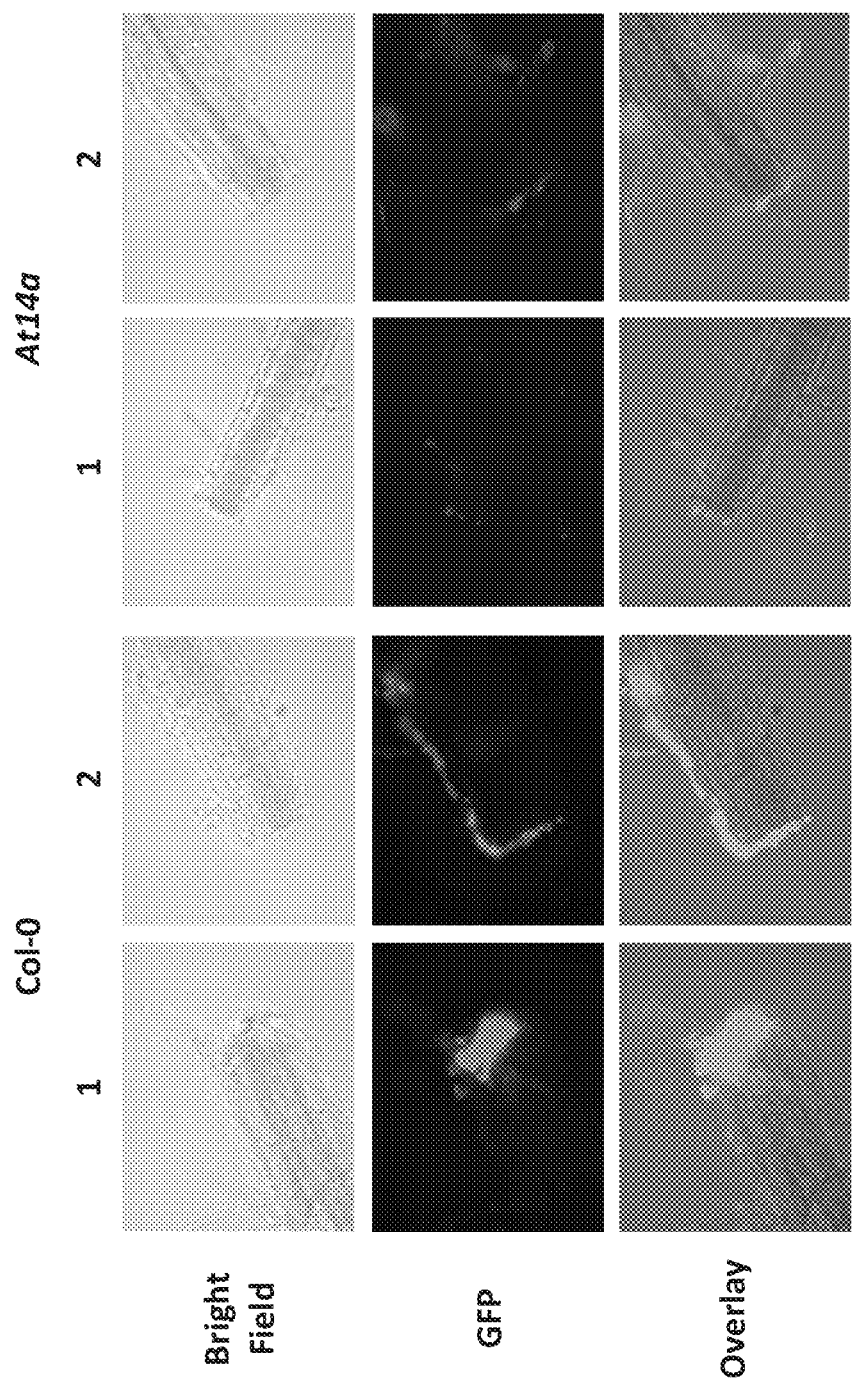
FIG. 26. At14a Binding: *Arabidopsis* At14a shows decreased binding of GFP-labeled *A. tumefaciens* A348.
Figure 27:
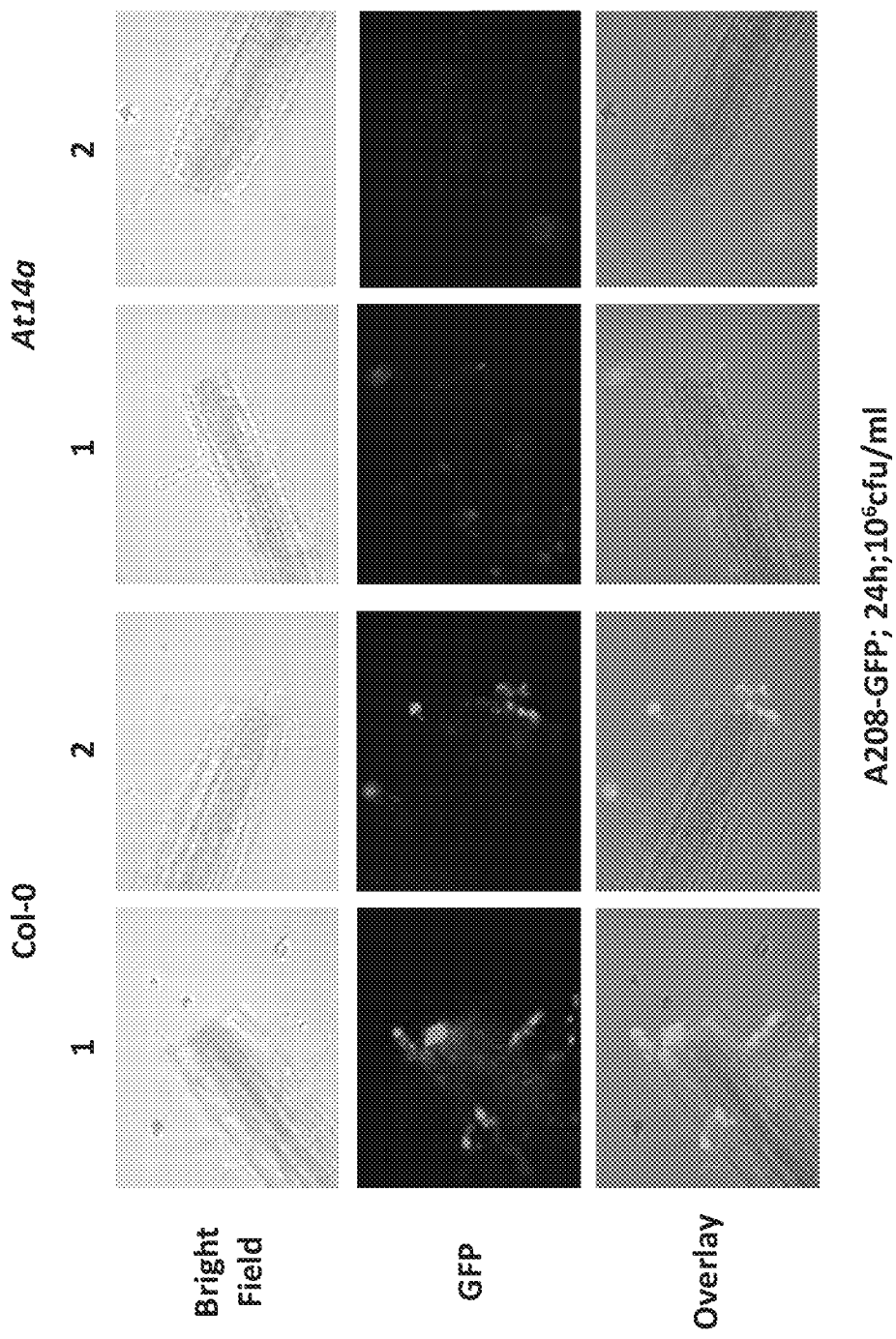
FIG. 27. At14a Binding: *Arabidopsis* At14a mutant shows decreased binding of GFP-labeled *A. tumefaciens* A208.
Figure 28:
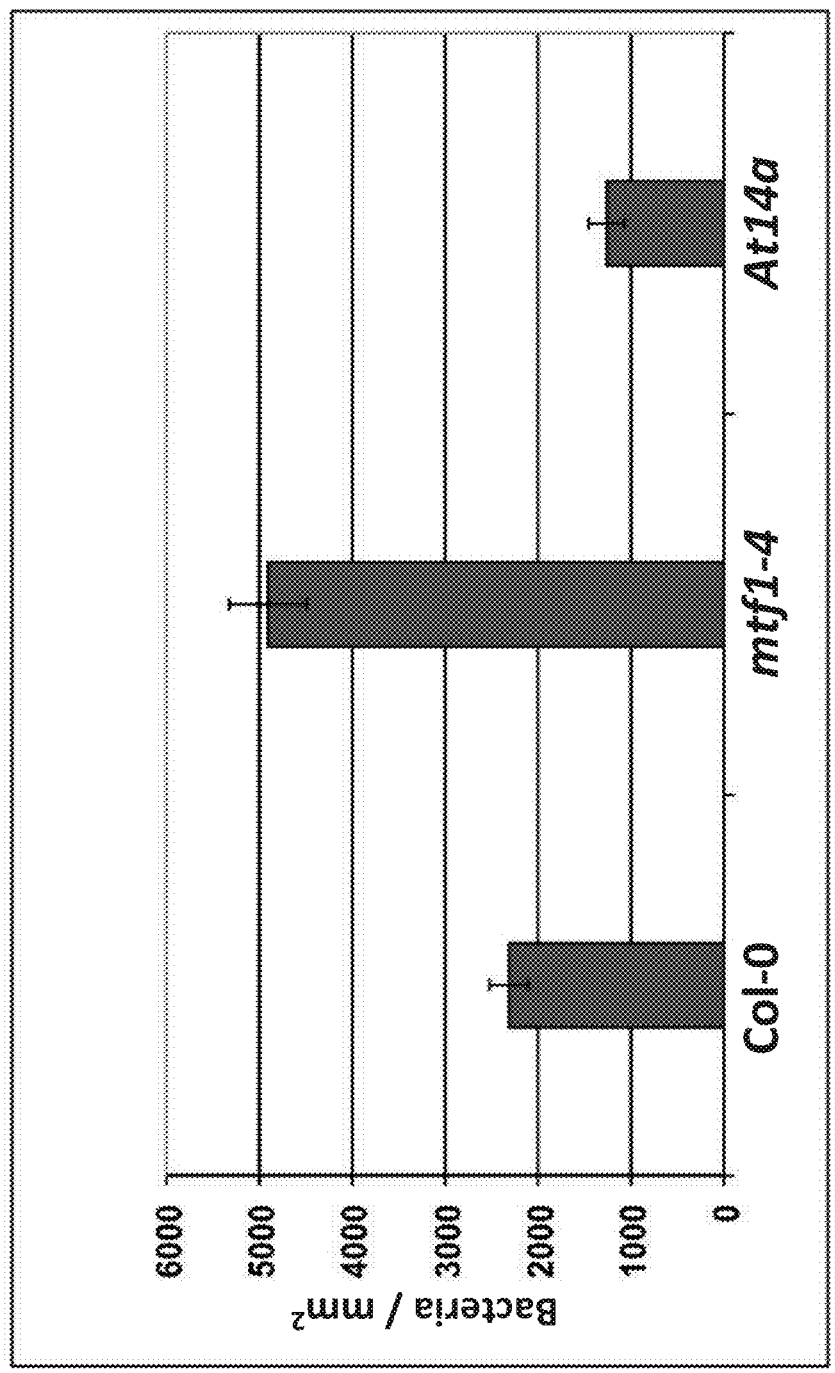
FIG. 28. At14a and mtf1-4: The At14a mutant shows decreased binding, and the mtf1-4 (previously mtf2) shows increased binding, of *A. tumefaciens* compared to *Arabidopsis* Col-0 (using scanning electron microscopy of unlabeled Agrobacteria).

A question was whether mtf1-4 (previously mtf2) plants showed altered susceptibility to other pathogens. Col-0 and mtf1-4 (previously mtf2) plants showed similar symptoms when infected with the necrotrophic fungus *Alternaria brassicicola*, and the virulent DC3000 or the non-pathogenic hrcC⁻ mutant strain of *Pseudomonas syringae* pv. tomato (FIG. 12). However, mtf1-4 (previously mtf2) plants showed increased resistance to infection by *Botrytis cinerea* (FIG. 6A). Leaves of mtf1-4 (previously mtf2) drop-inoculated with *B. cinerea* displayed smaller lesions than did wild-type plants (FIGS. 6B, 6C). Resistance to necrotrophic pathogens is mediated through jasmonic acid (JA) and ethylene. Microarray data revealed that At1g06160 (ORA59), encoding an octadecanoid-responsive *Arabidopsis* AP2/ERF transcription factor, is significantly up-regulated (1.6-fold; p<0.0001) in the mtf1-4 (previously mtf2) mutant. Because *B. cinerea* infection down-regulates MTF[35], ORA59 transcript levels were quantified in leaves of mtf1-4 (previously mtf2) and wild-type plants 0, 24, and 48 hours post-inoculation (hpi) with *B. cinerea* spores. By 24 hpi, more than a 3-fold increase in ORA59 transcript levels was seen in mtf1-4 (previously mtf2) compared to infected wild-type plants (FIG. 6D). Constitutive over-expression of ERF1 induces the expression of the defense-response genes PDF1.2 and ChiB (PR-3), and confers resistance to *B. cinerea* (Berrocal-Lobo et al., 2002). Thus, the modestly higher levels of ChiB (1.3-fold; p=0.004), and *B. cinerea*-induced up-regulation of ORA59 in mtf1-4 (previously mtf2), likely contribute to increased resistance to *B. cinerea*.

Example 9: Manipulation of Myb Transcription Factors to Improve Crop Transformation An *Arabidopsis* myb transcription factor (MTF) was identified which is a negative regulator of plant susceptibility to *Agrobacterium*-mediated transformation. Decreased expression of MTF results in a 10- to 15-fold increase in transformation frequency of the *Arabidopsis* ecotype Columbia (Col). Increased transformation susceptibility correlates with an increase in binding of Agrobacteria to the plant surface. This binding is mediated by an integrin-like protein. MTF expression is negatively regulated by cytokinins secreted by *Agrobacterium* cells, mediated by miaA and/or tzs.

mtf RNAi plants were generated in the transformation-recalcitrant ecotype BI-1 and transformation susceptibility was determined.

MTF orthologs were identified from crop species.

Using a bioinformatic approach i.e. "masking" the central myb DNA binding domain of MTF, and searching for proteins homologous to the N- and C-terminal regions of MTF, the correct myb orthology was verified by introducing the cDNA of an ortholog into the *Arabidopsis* mtf1-4 (previously mtf2) mutant and assaying for decreased transformation susceptibility.

MTF ortholog expression is identified in crop species using RNAi (or TILLING (Targeting Induced Local Lesion in Genomes)) and testing transformation susceptibility.

Results showed the following:
1. Decreased expression of MTF in *A. thaliana* ecotype BI-1 results in increased *Agrobacterium* attachment and transformation susceptibility.
2. MTF orthologs were identified from rice and three *Brassica* species. The identity of these orthologs was confirmed by functional complementation of the *Arabidopsis* mtf1-4 (previously mtf2) mutant.
3. Decreased expression of the rice MTF ortholog by RNAi results in increased rice transformation susceptibility.

Expression of the *Brassica* MTF orthologs are determined in their native species and the resulting plants are assayed for increased transformation susceptibility.

Expression of the rice MTF ortholog is decreased in transformation-recalcitrant *japonica* and *indicia* lines and the resulting plants are assayed for increased transformation susceptibility.

A transient RNAi system, delivered by *Agrobacterium*, silences crop MTF orthologs while simultaneously delivering genes of interest to these species.

MTF orthologs from soybean and wheat were identified and are silenced. Putative orthologs were identified using bioinformatics. (using BLAST® (Basic Local Alignment Search Tool))

Example 10: Involvement of the Integrin Domain-Like Protein At14a in *Agrobacterium*-Mediated Transformation. (See FIGS. 23, 24, 25A, 25B, 26, 27, 28)

Over-expression of the At14a gene in the *Arabidopsis* ecotype BI-1 increased bacterial binding to roots, and also increases root transformation. This ecotype is highly recalcitrant to *Agrobacterium*-mediated transformation, and binds bacteria poorly to roots.

Increasing *Agrobacterium*-mediated transformation of recalcitrant species, and tissues of these species, is achieved by over-expressing of the At14a gene. In particular, some tissues that are easy to regenerate but difficult to transform may not bind *Agrobacterium* well, and over-expressing At14a may improve binding and transformation.

MATERIALS AND METHODS

*A. tumefaciens* was cultured in Yeast Extract-Peptone medium (Lichtenstein et al., 1986) containing the appropriate antibiotics. Root transformation assays were carried out as previously described by Nam et al. with minor modifications (Tenea et al., 2009). MS basal medium lacking phytohormones was used to select for tumors. GUS activity assays were carried out after infection of root segments with *A. tumefaciens* At849 (Narasimhulu et al., 1996) for 4-6 d, using X-gluc (Jefferson et al., 1987). Detailed procedures for identifying and screening *Arabidopsis* mutants, generating transgenic plants, quantitative real-time RT-PCR, bacterial attachment assays, phytohormone treatment of plant roots, microarray experiments, and infection of plants with pathogenic microbes are available in the Methods.

Agrobacterium Culture, Plant Growth Conditions and Transformation Assays

*A. tumefaciens* was cultured in Yeast Extract-Peptone medium containing appropriate antibiotics. Root transformation assays were carried out as previously described with minor modifications. MS basal medium lacking phytohormones was used to select for tumors. GUS activity assays were carried out after infection of root segments with *A. tumefaciens* At849 for 4-6 d, using X-gluc.

Arabidopsis Mutants

~4000 mutagenized plants from an activation-tagged library were screened at low *Agrobacterium* inoculation densities ($10^5$ and $10^6$ cfu/mL) for increased root transformation. TAIL-PCR was utilized to identify the T-DNA/plant junction from hat3. Primers for TAIL-PCR are listed in Table 2.

Seeds of the T-DNA insertion MTF mutants SALK_072082 (mtf1), SALK_072083 (mtf1-4) (previously mtf2), and SALK_102624 (mtf3) (Alonso et al., 2003) were obtained from the *Arabidopsis* Biological Resource Center (Columbus, Ohio). The mutants were genotyped using primers listed in Table 2.

Generation of Transgenic MTF-Complemented Plants

MTF cDNA was synthesized from 1-2 µg RNA using oligo(dT) and the SuperscriptIII First Strand Synthesis System for RT-PCR™ (Invitrogen, Carlsbad, Calif.), following the manufacturer's protocol. Primer sequences are listed in Table 2. The polymerase chain reaction (PCR) was conducted using PfuTurbo DNA polymerase (Stratagene, La Jolla, Calif.) and 200 ng of *Arabidopsis* Columbia root cDNA. PCR products were cloned into the SmaI site of pBluescript II SK+ (Stratagene). MTF cDNA was excised using XhoI and SpeI and cloned into the binary vector pE1775 (Lee et al., 2007). The resulting construction, pE3263, was introduced into *A. tumefaciens* GV3101 by electroporation and used for floral dip transformation (Clough and Bent, 1998) of the mutant mtf1-4. Transgenic plants were selected on B5 medium containing 20 µg/mL hygromycin.

Quantitative Real-Time RT-PCR Analysis

Real-time RT-PCR was carried out using total RNA isolated in triplicate from roots of plants grown in liquid B5 medium. PCR was performed in triplicate on an ABI Prism 7500 Sequence Detection System (Applied Biosystems, Foster City, Calif.). Expression levels were calculated by the relative standard curve method (Applied Biosystems) for all transcripts except ORA59, where the comparative cycle threshold method (Applied Biosystems) was used, and normalized to Actin2 transcript levels. Transcript levels of genes identified in microarray experiments were validated by RT-PCR. The list of primers is given in Table 2.

Generation of MTF-RNAi Lines

MTF-RNAi lines were generated using pFGC1008 (GenBank Accession AY310333). The RNAi construct (pE3387) contained a ~400 bp cDNA fragment of MTF amplified using primers listed in Table 2. The MTF fragment was oriented as an inverted repeat with each repeat separated by a fragment from the gusA gene. RNAi lines, in ecotype Bl-1, were produced by floral-dip transformation using *A. tumefaciens* GV3101. Transgenic plants were selected on B5 medium containing hygromycin.

Bacterial Attachment Assays

Root segments of *Arabidopsis* Bl-1 and MTF-RNAi lines were incubated with *A. tumefaciens* A208 containing pJZ383 ($P_{tac}$::GFP). Root segments were co-cultivated with $10^5$ cfu/mL (ecotype Columbia) or $10^8$ cfu/mL (ecotype Bl-1) for 24 h in B5 minimal medium. Root segments were rinsed and visualized by epifluorescence microscopy.

Generation of MTF Promoter-EYFP Transgenic Plants

~1.2 kb of the MTF promoter was amplified using a forward primer incorporating an AgeI restriction site at the 5' end and a reverse primer incorporating the sequence for the first ten amino acids of MTF and a BamHI restriction site. Primers are listed in Table 2. The amplification product was cloned into the SmaI site of pBluescriptII SK+. The MTF promoter was excised using AgeI and BamHI and cloned into these sites of pSAT6-EYFP-N1[46] as a translational fusion with EYFP. The expression cassette was cloned as a PI-PspI fragment into pPZP-RCS2 (Tzfira et al., 2005). The resulting plasmid was transformed into *A. tumefaciens* GV3101 and used for floral-dip transformation of *Arabidopsis* Col-0. Transgenic plants were selected on B5 medium supplemented with hygromycin.

Phytohormone Treatment of Plant Roots

Plants of *Arabidopsis* ecotypes Ws-2, Bl-1, Bla-2, Cal-0, Dijon-G, and Petergof were grown as described by Nam et al. and roots were excised and incubated on CIM for 0, 1, or 3 days prior to cutting into segments and infection with *A. tumefaciens* A208 for tumorigenesis assays or strain At849 for transient GUS expression assays.

For assessing the effect of cytokinins on MTF transcript levels and transformation, root segments from *Arabidopsis* Col-0 or Bl-1 were incubated on MS medium supplemented with 0, 1.4 or 14 µM trans-zeatin, and co-cultivated with either *A. tumefaciens* A348 or A281 for 48 h. Roots were infected with bacteria at $10^6$ cfu/mL (Col-0) or $10^8$ cfu/mL (Bl-1). Following infection, root segments were either transferred to MS basal medium containing 100 µg/mL Timentin and incubated for 4-5 weeks before recording the percentage of root segments developing tumors, or used for RNA isolation.

*Agrobacterium* attachment assays were conducted as described herein. Col-0 and Bl-1 root segments were co-cultivated with A281 at $10^6$ or $10^8$ cfu/mL, respectively, for 24 h in the presence or absence of 1.4 µM trans-zeatin.

Microarray Analysis

Surface-sterilized seeds of wild-type, hat3, and mtf1-4 (previously mtf2) were germinated in B5 medium and seedlings grown for 2-weeks at 23° C. under a 16 h light/8 h dark photoperiod. Three biological replicates, each consisting of twenty seedlings of each line transferred to liquid B5 medium, were grown for 12 days. Roots were frozen in liquid $N_2$. RNA was isolated using Trizol reagent (Invitrogen). Microarray experiments were performed according to the Affymetrix GeneChip Expression Analysis Manual (http://www.affymetrix.com) using *Arabidopsis* ATH1 Genome Arrays (Affymetrix) at the Purdue University Genomics Center. GeneChip operating software was used to produce CEL files containing raw probe intensities for the arrays. Data from these files were read with "Biobase" and "affy" packages in R/Bioconductor (Gentleman et al., 2004) for analysis of genomic data. A background correction was performed on the perfect match intensities to make signals from different chips comparable. A robust local regression was employed to normalize background corrected data. An analysis of variance (ANOVA) method was employed as previously described by Chu et al., 2002, to detect probe sets which are differentially expressed between two lines using the natural log of the background corrected, normalized data as the gene expression level. To determine whether there was a statistically significant difference between two lines, it was sufficient to test whether the line effect was different from zero. This ANOVA model was performed for Col vs hat3, Col vs mtf1-4 (previously mtf2), and mtf1-4 vs hat3. Both the false discovery rate (FDR) approach (Benjamini et al., 1995) and Holm's sequential Bonferroni correction procedure (Holm, 1979) were used to adjust for multiple testing, with a significance level a of 0.05.

Generation of Transgenic *Arabidopsis* Lines Over-Expressing Genes Up-Regulated in mtf Mutants cDNAs of At2g40960, At1g50060, At5g46295, and At5g15725 were amplified using primers containing KpnI and SacI sites, and cloned into the SmaI site of pBluescriptII SK+. The primers used for amplification are listed in Table 2. DNA was digested with KpnI and SacI and cloned into pE1775 (Lee et al., 2007). The resulting constructs were introduced into *A. tumefaciens* GV3101 by electroporation and used for floral-dip transformation of *Arabidopsis* Col-0. Transgenic plants were selected on B5 medium supplemented with hygromycin.

Disease Assays on Col-0 and Mtf1-4 (Previously Mtf2)

Fungal and bacterial cultures were maintained and disease assays performed as previously described by Mengiste et al., 2003. *Botrytis cinerea* strain B05-10 spores were harvested 10 days after initiating culture and re-suspended in 1% Sabouraud Maltose Broth (SMB) media (DIFCO, Sparks, Md.) at a concentration of $2.5 \times 10^5$ spores/mL for spray- and drop-inoculation of whole plants. *Alternaria brassicicola* spores were harvested and re-suspended in distilled water at a concentration of $5 \times 10^5$ spores/ml for drop-inoculation of detached leaves. Disease assays with *Pseudomonas syringae* pv. tomato DC3000 and hrcC were done as described.

TABLE 1

Fold-change of significantly differentially regulated genes in two MTF mutants compared to the wild-type, identified by microarray analyses

| | | Fold change | |
|---|---|---|---|
| Gene | Annotation | hat3 | mtf1-4 |
| Up-regulated genes | | | |
| At1g71870 | MATE efflux family protein | 3.9 | 3.3 |
| At3g05730 | defensin-like (DEFL) family protein | 3.0 | 3.1 |
| At2g25510 | unknown protein | 1.6 | 2.6 |
| At3g16670 | phylloplanin precursor (T-phylloplanin) | 2.4 | 2.4 |
| At5g10040 | hypothetical protein | 2.6 | 2.1 |
| At2g02990 | ribonuclease, RNS1 | 2.2 | 2.0 |
| At2g41230 | similar to ARL (ARGOS-LIKE) | 1.4 | 2.0 |

TABLE 1-continued

Fold-change of significantly differentially regulated genes in two MTF mutants compared to the wild-type, identified by microarray analyses

| | | Fold change | |
|---|---|---|---|
| Gene | Annotation | hat3 | mtf1-4 |
| At2g40960 | nucleic acid binding | 1.5 | 1.9 |
| At1g50060 | putative pathogenesis-related protein | 1.3 | 1.8 |
| At5g46295 | expressed protein | 1.8 | 1.7 |
| At5g05900 | UGT 76C3 | 1.3 | 1.7 |
| At3g62760 | glutathione transferase III-like protein | 1.4 | 1.7 |
| At5g14750 | myb transcription factor werewolf (WER)/MYB66 | 1.5 | 1.7 |
| At5g15725 | expressed protein | 1.3 | 1.6 |
| At1g74490 | putative protein kinase | 1.6 | 1.6 |
| At4g38080 | putative hydroxyproline-rich glycoprotein family protein | 1.9 | 1.6 |
| At4g29690 | nucleotide pyrophosphatase-like protein | 1.9 | 1.6 |
| At2g25980 | jacalin lectin family protein | 1.4 | 1.5 |
| At1g74500 | putative DNA-binding bHLH protein | 1.4 | 1.5 |
| At1g23160 | GH3-like auxin-regulated protein | 1.7 | 1.5 |
| At5g44260 | zinc finger (CCCH-type) family protein | 1.3 | 1.5 |
| At2g40010 | 60S acidic ribosomal protein P0 | 1.4 | 1.5 |
| At3g17990 | phosphoethanolamine N-methyltransferase 1 | 1.5 | 1.5 |
| Down-regulated genes | | | |
| At2g40970 | myb family transcription factor | 4.0 | 4.3 |
| At1g35210 | expressed protein | 1.4 | 2.3 |
| At1g77640 | ERF/AP2 transcription factor DREBA5 | 1.7 | 2.2 |
| At3g56710 | SigA binding protein | 1.3 | 1.9 |
| At5g37770 | calmodulin-related protein 2, touch-induced (TCH2) | 1.3 | 1.8 |
| At5g39670 | calcium-binding protein (CBP1) | 1.5 | 1.8 |
| At2g43290 | calmodulin-like protein (MSS3) | 1.3 | 1.8 |
| At4g25470 | DRE CRT-binding protein DREB1C | 1.4 | 1.7 |
| At5g49520 | WRKY48 | 1.3 | 1.7 |
| At4g11280 | ACC synthase (AtACS-6) | 1.3 | 1.6 |
| At1g51920 | expressed protein | 1.4 | 1.6 |
| At1g66160 | U-box domain-containing protein | 1.3 | 1.6 |
| At5g47960 | RAS superfamily GTP-binding protein (SMG1) | 1.3 | 1.6 |
| At1g49230 | RING-H2 finger protein RHA3a | 1.2 | 1.5 |
| At4g20000 | SigA binding protein family | 1.2 | 1.5 |

TABLE 2

Sequences of primers used (SEQ ID NOS 2-70, respectively, in order of appearance)

| Gene | Primer Name | Sequence (5'→3') |
|---|---|---|
| RT-PCR primers: | | |
| At3g18780 | Actin-FP | CTAAGCTCTCAAGATCAAAGGCTTA |
| | Actin-RP | ACTAAAACGCAAAACGAAAGCGGTT |
| | Actin2-F | GAAGTACAGTGTCTGGATCGGTGGTT |
| | Actin2-R | ATTCCTGGACCTGCCTCATCATACTC |
| At1g71870 | At1g71870-F | TGTGGTTTGGGTTGCTTTCAGCTC |
| | At1g71870-R | TCAGTCTCATTGCCTTCACGGCTT |
| At3g05730 | At3g05730-F | ATGGCAAAGACCCTCAATTCCATCTG |
| | At3g05730-R | TATTTCAACGACCGTAGCAGTGGC |
| At3g16670 | At3g16670-F | TCCTCAACATAGTCGCTATCCTCCCA |
| | At3g16670-R | GAGAAGGGAAACACACTGTAACCGAAC |
| At5g10040 | At5g10040-F | TTGCTGTGGCGGTTTCTAGTGGCTTT |
| | At5g10040-R | ACATGCCCTCTGGTGATTAGAAAGC |
| At2g02990 | At2g02990-F | CTGGTTCCGGTTTAATCGAATGTCCG |
| | At2g02990-R | GATCGATGCCGGTTCAAGAGACTGAA |

TABLE 2-continued

Sequences of primers used (SEQ ID NOS 2-70, respectively, in order of appearance)

| Gene | Primer Name | Sequence (5'→3') |
|---|---|---|
| At2g40960 | At2g40960-F | AGCTGGTACCATGGACACAGCATTGACC |
|  | At2g40960-R | CCGGGAGCTCTTACCGGTTCTGCATG |
| At2g41230 | At2g41230-F | CCTCCTCCTTCCTCTACTCCTCATGATT |
|  | At2g41230-R | TTATGTATGTACGGACGGTTCGCAACGC |
| At5g46295 | At5g46295-F | TGAGAAGATGATGAGAAAAGGGAAGCTTTC |
|  | At5g46295-R | TGTTAGAATTTACAACCACAACAGAGGAAG |
| At1g50060 | At1g50060-F | CAGTGAAGATAGGGTGTGCTAGGGTT |
|  | At1g50060-R | ATCAGTAAGGGTACTCTCCGACCCAA |
| At3g62760 | At3g62760-F | ATCTCCACCACGTGCCTTACACTTAC |
|  | At3g62760-R | TTAAGGAAAGCCGGACGAGAACAGAG |
| At5g14750 | At5g14750-F | TGGGTTCATGAGGATGAGTTTGAGC |
|  | At5g14750-R | GACTGTTGATGTATTAGTGTTTGATCAGC |
| At5g15725 | At5g15725-F | CGACCAAGGATATAATATGAAGAAGACGAG |
|  | At5g15725-R | GTCAATTAGTGACGATTACGCACGCC |
| At1g74490 | At1g74490-F | TTTAGTCCTTAGGATGTCTGAGAAACCC |
|  | At1g74490-R | GGTTAGACCATCGATGCTTGAGGT |
| At4g38080 | At4g38080-F | GCCCACAATCCCTAACATTCCACAGA |
|  | At4g38080-R | AGTGTGTGATCCAAAGCTGTCTCAGG |
| At1g35210 | At1g35210-F | GGTTTGGTAATGGGCACAAAGAAGAG |
|  | At1g35210-R | CTTGCACGTACCCACCAAACTGATCT |
| At1g77640 | At1g77640-F | CGGAGATCCGTTTGATTATTCTCCAC |
|  | At1g77640-R | TGGACCGTTGGATTAACTGAAACTCC |
| At3g56710 | At3g56710-F | GTGATTGTTATGAGCCGTTGAATGCGG |
|  | At3g56710-R | TCACATAGAATCGATGCTTCCAAAGTCA |
| At5g37770 | At5g37770-F | GTGAGAAGTGCTCTGTGCAAGATTGT |
|  | At5g37770-R | CGGCGAAATCTTCCAAATCCTCAAGC |
| At5g39670 | At5g39670-F | CGATGGAAGTAAAGACGGAAGAATCG |
|  | At5g39670-R | GGTGCGGAGACAACAGTATTAACAGAC |
| At2g43290 | At2g43290-F | AGGTGGTGGCTTTAGCAGCAGTA |
|  | At2g43290-R | ACACCTTCCTCGATTACACGATGTT |
| At4g25470 | At4g25470-F | TTGATGTCGAGGGAGATGATGACGTG |
|  | At4g25479-R | ACCATTTACATTCGTTTCTCACAACCAA |
| At5g49520 | At5g49520-F | CCTTCGCAGATCAGATCCGATACTATT |
|  | At5g49520-R | ACTCCTCATGAAACCTACCTACCGGA |
| At4g11280 | At4g11280-F | GAAGAAGTGTTGGCAGAGTAACCTCAG |
|  | At4g11280-R | TCTGTGCACGGACTAGCGGAGAA |

TAIL-PCR primers:
Degenerate primers:

| | | |
|---|---|---|
| AD1: | | NTCASTWTWTSGWGTT |
| AD2: | | NGTCGASWGANAWGAA |
| AD3: | | WGTGNAGWANCANAGA | pSKI015-specific primers:

| | | |
|---|---|---|
| ACT-TAIL1: | | TGGATTGATGTGATATCTAGATCCG |
| ACT-TAIL2: | | CCCCCACCCACGAGGAACATCGTGG |
| ACT-TAIL3: | | GGAAGATGGCTTCTACAAATGCCAT |

Primers to genotype MTF mutant plants:

| | | |
|---|---|---|
| MTF-RT forward: | | CTCATCCCTATCTCTCAAACC |
| MTF reverse: | | TTCCGGCAGGGAAGAGCTTAAGCATCTT |
| T-DNA primer LBa1: | | TGGTTCACGTAGTGGGCCATCG |

TABLE 2-continued

Sequences of primers used (SEQ ID NOS 2-70, respectively, in order of appearance)

| Gene | Primer Name | Sequence (5'→3') |
|---|---|---|
| Primers to amplify MTF cDNA: | | |
| | MTF-XhoI-F | ACGGCTCGAGATGAGAGAAGATAATCCA |
| | MTF-SpeI-R | AACCACTAGTTTAATTTCCGGCAGGGAAG |
| Real-time RT-PCR primers: | | |
| | MTF-RT forward | CTCATCCCTATCTCTCAAACC |
| | MTF-RT reverse | TCTGAAGATGACTCGCAACGT |
| | qORA59-F | TCGCGGCCGAGATAAGAGACTC |
| | qORA59-R | TCCGGAGAGATTCTTCAACGACATCC |
| MTF RNAi primers: | | |
| | MTF-RNAi-F | ACACTAGTGGCGCGCCTTTACCTTAGGAGAATGC |
| | MTF-RNAi-R | ACGGATCCATTTAAATTTGATCCTGACGACAAAT |
| MTF promoter primers: | | |
| | MybPro-AgeI: | CCCCACCGGTATACTACAAAATACCTAAAACAAAATGT |
| | MybPro-BamHI: | CCAAGGATCCGAGATGGAAGCTCTTCTTC |

PUBLICATIONS CITED

These publications are incorporated by reference to the extent they relate materials and methods disclosed herein.

Aly, K. A., et al. *J. Bacteriol.* 190, 1595-1604 (2008).
Beaty, J. S. et al. *Mol. Gen. Genet* 203, 274-280 (1986).
Benjamini, Y. & Hochberg, Y. *J. Roy. Statist. Soc. Ser. B (Methodol.)* 57, 289-300 (1995).
Berrocal-Lobo, M., et al. *Plant J.* 29, 23-32 (2002).
Chateau, S., et al. *J. Exp. Bot.* 51, 1961-1968 (2000).
Chu, T.-M., et al. *Mathematical Biosci.* 17, 35-51 (2002).
Claeys, M., et al. *Fresenius Z. Anal. Chem.* 290, 125-126 (1978).
Clough, S. J. & Bent, A. F. *Plant J.* 16, 735-743 (1998).
Fernandez, C. et al. *J. Mol. Biol.* 266, 576-593 (1997).
Gentleman, R. C., et al. *Genome Biol.* 5, R80 (2004).
Hazen, S. P. et al. *Proc. Natl. Acad. Sci.* 102, 10387-10392 (2005).
Holm, S. *Scand. J. Stat.* 6, 65-70 (1979).
Hwang, H.-H. et al. *Mol. Plant Pathol.* 11, 677-690 (2010).
Jefferson, R. A., et al. *EMBO J.* 6, 3901-3907 (1987).
Lacroix, B., et al. *Trends Genet.* 22, 29-37 (2006).
Lee, L.-Y. et al. *Plant Physiol.* 145, 1294-1300 (2007).
Lichtenstein, C. & Draper, J. Genetic engineering of plants. In *DNA Cloning. A Practical Approach* (ed. D. M. Glover), Vol. 2, 67-119 (Washington, D.C., IRL Press, 1986).
Liu, Y.-G., et al. *Plant J.* 8, 457-463 (1995).
McCloskey, J. A., et al. *FEBS Lett.* 111, 181-183 (1980).
McCullen, C. A. & Binns, A. N. *Annu. Rev. Cell Dev. Biol.* 22, 101-127 (2006).
Mengiste, T., et al. *Plant Cell* 15, 2551-2565 (2003).
Milne, T. J., et al. *J. Biol. Chem.* 278, 31105-31110 (2003).
Mysore, K. S., et al. *Plant J.* 21, 9-16 (2000).
Nam, J. et al. *Mol. Gen. Genet.* 261, 429-438 (1999).
Nam, J., et al. *Plant Cell* 9, 317-333 (1997).
Narasimhulu, S. B., et al. *Plant Cell* 8, 873-886 (1996).
Niki, T., et al. *Plant Cell Physiol* 39, 500-507 (1998).
Powell, G. K., et al. *Mol Plant-Microbe Interact.* 1, 235-242 (1988).
Regier, D. A. & Morris, R. O. *Biochem. Biophys. Res. Commun.* 104, 1560-1566 (1982).
Tenea, G. N. et al. *Plant Cell* 21, 3350-3367 (2009).
Tzfira, T. et al. *Plant Mol. Biol.* 57, 503-516 (2005).
Valvekens, D., et al. *Proc. Natl. Acad. Sci. USA* 85: 5536-5540 (1988).
Veena, Jiang, H., et al. *Plant J.* 35, 219-236 (2003).
Villemont, E., et al. *Planta* 201, 160-172 (1997).
Weigel, D. et al. *Plant Physiol.* 122, 1003-1013 (2000).
Xing, D.-H. et al. *Mol. Plant* 1, 459-470 (2008).
Zhan, X., et al. *Plant Mol. Biol.* 14, 785-792 (1990).
Zhu, Y. et al. *Plant Physiol.* 132, 494-505 (2003).
Zimmermann, P., Hirsch-Hoffmann, M., Hennig, L. & Gruissem, W. GENEVESTIGATOR. *Arabidopsis* microarray database and analysis toolbox. *Plant Physiol.* 136, 2621-2632 (2004).

The invention claimed is:

1. A method to increase transformation susceptibility in a plant selected from the group consisting of Brassica, Arabidopsis, and rice, the method comprising:
    (a) down-regulating expression of endogenous genes encoding myb transcription factors in Brassica, Arabidopsis, or rice by using RNAi or trans-zeatin secretion (TZS) expressing bacteria,
    wherein the myb transcription factor in Brassica is selected from the group of amino acid sequences consisting of SEQ ID NO: 71 encoded by SEQ ID NO: 78, SEQ ID NO: 72 encoded by SEQ ID NO: 79, and SEQ ID NO: 73 encoded by SEQ ID NO: 80, and combinations thereof; the myb transcription factor in Arabidopsis is SEQ ID NO: 74 encoded by SEQ ID NO: 76; and the myb transcription factor in rice is SEQ ID NO: 75 encoded by SEQ ID NO: 77, and
    (b) contacting the Brassica, Arabidopsis, or rice plant having the downregulated myb transcription factor with Agrobacteria, thereby increasing transformation susceptibility.

2. A method to increase transformation susceptibility in a plant selected from the group consisting of Brassica, Arabidopsis, and rice, the method comprising:
    (a) decreasing expression of a gene encoding a functional ortholog of a family of myb transcription factors designated MTF in Arabidopsis using RNAi or TZS in Brassica, Arabidopsis, and rice;
    wherein the transcription factors negatively regulate plant transformation susceptibility; and
    wherein the nucleic acid sequence encoding the functional ortholog is selected from the group consisting of SEQ ID NOs: 78, 79, 80 and combinations thereof in Brassica; the nucleic acid sequence encoding the functional ortholog is SEQ ID NO: 76 in Arabidopsis; and the nucleic acid sequence encoding the functional ortholog is SEQ ID NO: 77 in rice; and
    (b) contacting the Brassica, Arabidopsis, or rice plant having the downregulated myb transcription factor with Agrobacteria, thereby increasing transformation susceptibility.

* * * * *